(12) United States Patent
d'Adda di Fagagna et al.

(10) Patent No.: US 10,240,154 B2
(45) Date of Patent: Mar. 26, 2019

(54) RNA PRODUCTS AND USES THEREOF

(71) Applicant: IFOM Fondazione Istituto FIRC di Oncologia Molecolare, Milan (IT)

(72) Inventors: Fabrizio d'Adda di Fagagna, Milan (IT); Sofia Francia, Milan (IT); Flavia Michelini, Milan (IT); Francesca Rossiello, Milan (IT)

(73) Assignee: IFOM Fondazione Istituto FIRC di Oncologia Molecolare, Milan (IT)

( * ) Notice: Subject to any disclaimer, the term of this patent is extended or adjusted under 35 U.S.C. 154(b) by 0 days.

(21) Appl. No.: 15/476,800

(22) Filed: Mar. 31, 2017

(65) Prior Publication Data

US 2018/0066251 A1 Mar. 8, 2018

Related U.S. Application Data

(62) Division of application No. 14/400,131, filed as application No. PCT/EP2013/059753 on May 10, 2013, now Pat. No. 9,708,606.

(60) Provisional application No. 61/645,285, filed on May 10, 2012.

(51) Int. Cl.
| | | |
|---|---|---|
| *C07H 21/02* | (2006.01) | |
| *C07H 21/04* | (2006.01) | |
| *A61K 48/00* | (2006.01) | |
| *C12N 15/113* | (2010.01) | |
| *C12Q 1/6883* | (2018.01) | |

(52) U.S. Cl.
CPC .......... *C12N 15/113* (2013.01); *C12Q 1/6883* (2013.01); *C12N 2310/11* (2013.01); *C12N 2310/14* (2013.01); *C12N 2310/3231* (2013.01); *C12N 2320/11* (2013.01); *C12N 2320/30* (2013.01); *C12N 2320/31* (2013.01); *C12Q 2600/118* (2013.01); *C12Q 2600/136* (2013.01); *C12Q 2600/178* (2013.01)

(58) Field of Classification Search
CPC .. C12N 15/113; C12N 2310/11; A61K 31/713
See application file for complete search history.

(56) References Cited

FOREIGN PATENT DOCUMENTS

WO WO 2012/013821 A1 2/2012

OTHER PUBLICATIONS

Armanios, Syndromes of Telomere Shortening; Annual Review of Genomics and Human Genetics, vol. 10, pp. 45-61; 2009.
Bartkova et al., DNA damage response as a candidate anti-cancer barrier in early human tumorigenesis; Nature Publishing Group, vol. 434, pp. 864-870; Apr. 14, 2005.
Crosetto et al., Nucleotide-resolution DNA double-strand break mapping by next-generation sequencing; Nature Methods, vol. 10, No. 4, pp. 361-365; Apr. 2013.
D'Adda Di Fagagna, Living on a break: cellular senescence as a DNA-damage response; Nature Reviews Cancer, vol. 8, No. 7, pp. 512-522; Jul. 2008.
Di Micco et al., Oncogene-induced senescence is a DNA damage response triggered by DNA hyper-replication; Nature Publishing Group, vol. 444, pp. 638-642; Nov. 30, 2006.
Francia et al., Site-specific DICER and DROSHA RNA products control the DNA damage response; Nature Publishing Group, vol. 488, pp. 231-235; Aug. 9, 2012; http://doi.org/10.1038/nature11179.
Jackson et al., The DNA-damage response in human biology and disease; Nature, vol. 461, No. 7267, pp. 1071-1078; Oct. 22, 2009.
Ren et al., Dicer-dependent Biogenesis of Small RNAs Derived from 7SL RNA; PLoS One, vol. 7, No. 7, pp. e40705-e40705; Jul. 2012.
Seo et al., Genome-wide profiles of H2AX and γ-H2AX differentiate endogenous and exogenous DNA damage hotspots in human cells; Nucleic Acids Research, vol. 40, No. 13, pp. 5965-5974; 2012.
Vvei et al., A Role for Small RNAs in DNA Double-Strand Break Repair; Cell, vol. 149, No. 1, pp. 101-112; Mar. 2012.

*Primary Examiner* — Amy H Bowman
(74) *Attorney, Agent, or Firm* — Knobbe Martens Olson & Bear LLP

(57) ABSTRACT

The present invention relates to small RNAs, inhibitors thereof, inhibitors of enzymes producing thereof, and their use to modulate the response of a cell to a DNA damaging event. The invention concerns also a method to detect the presence or quantify DNA damage.

17 Claims, 55 Drawing Sheets

Specification includes a Sequence Listing.

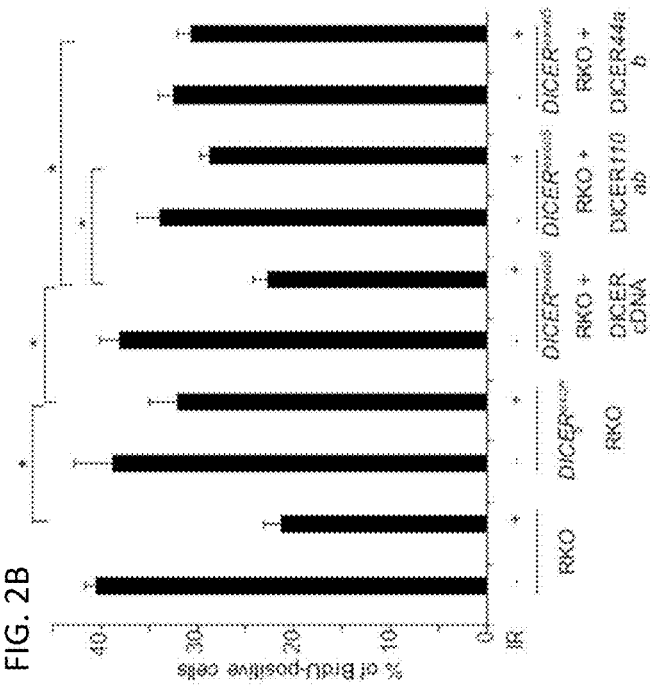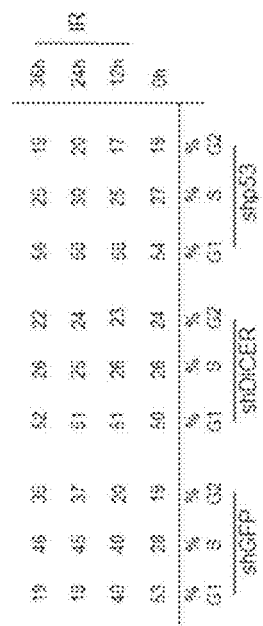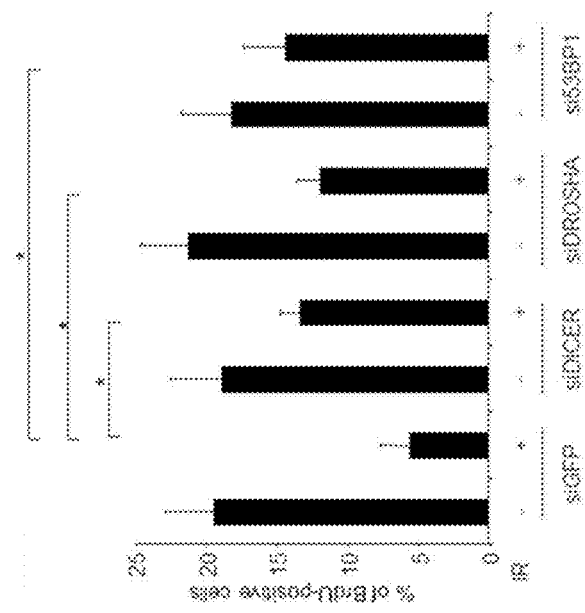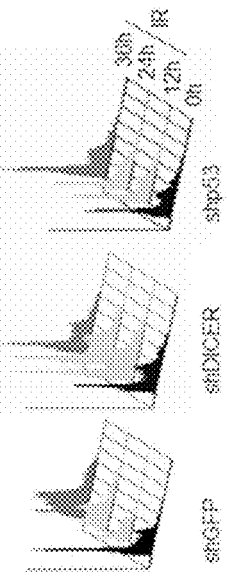
FIG. 2A
FIG. 2B
FIG. 2C
FIG. 2D

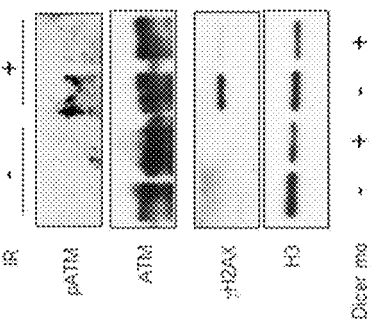
FIG. 3B
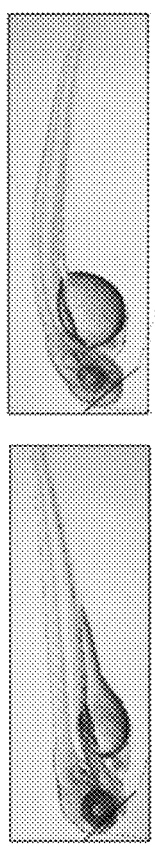
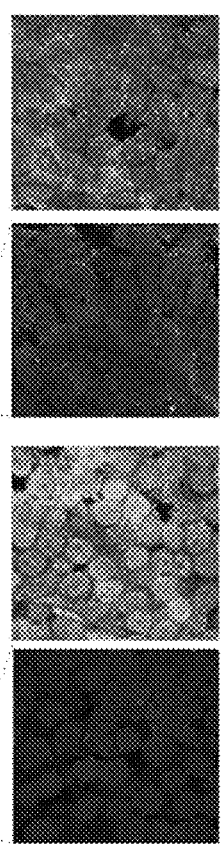
FIG. 3A
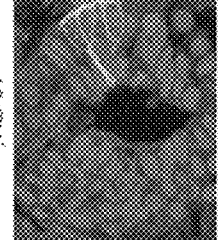
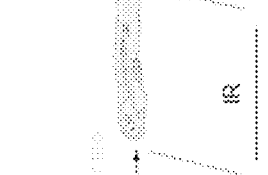
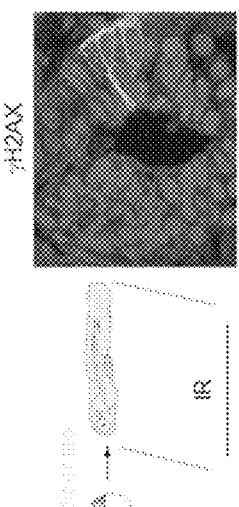
FIG. 3D
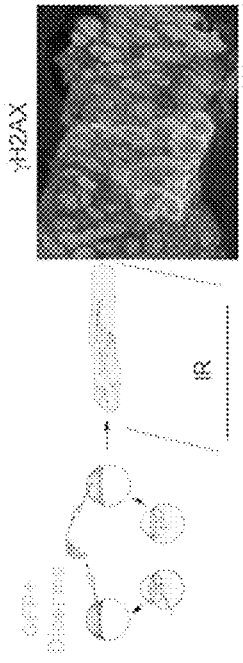
FIG. 3C

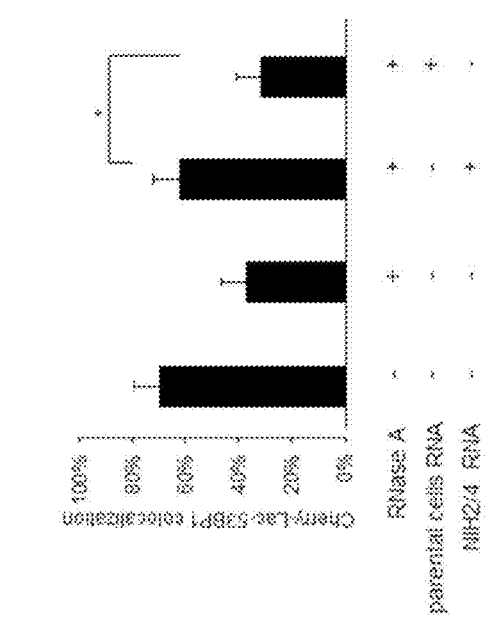

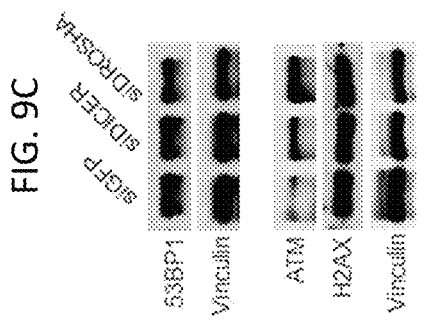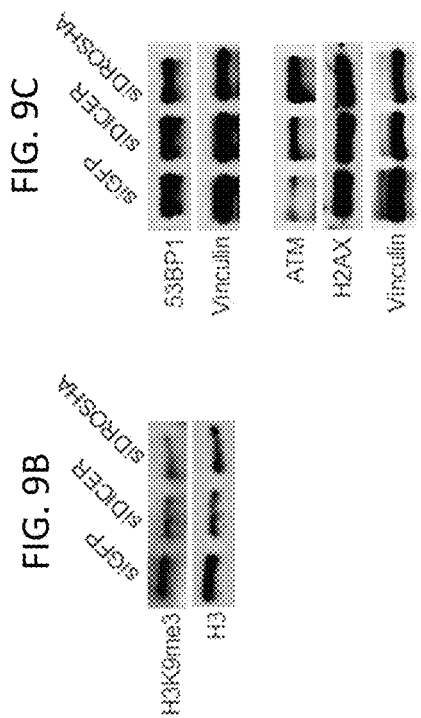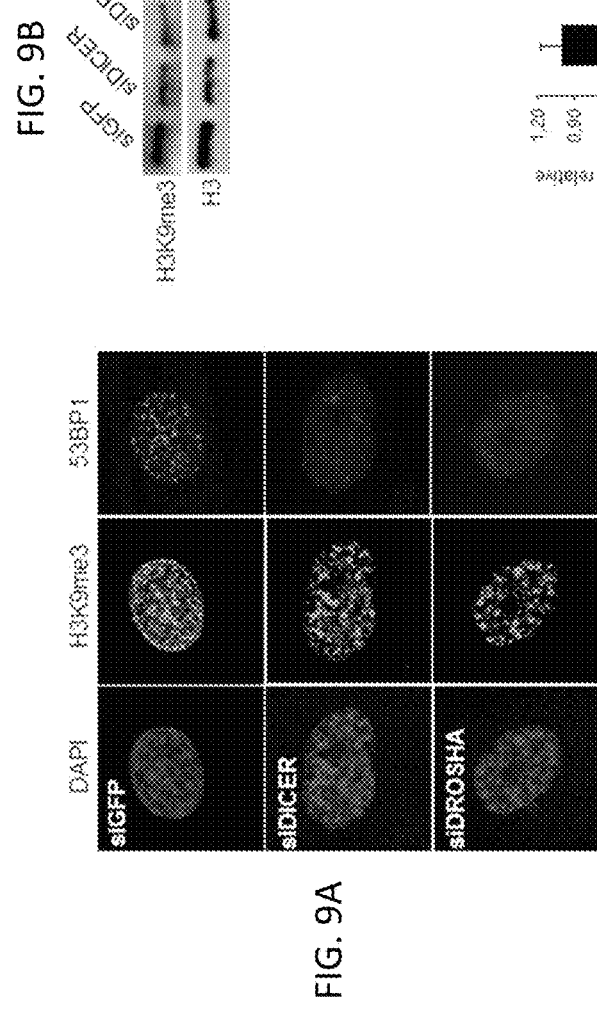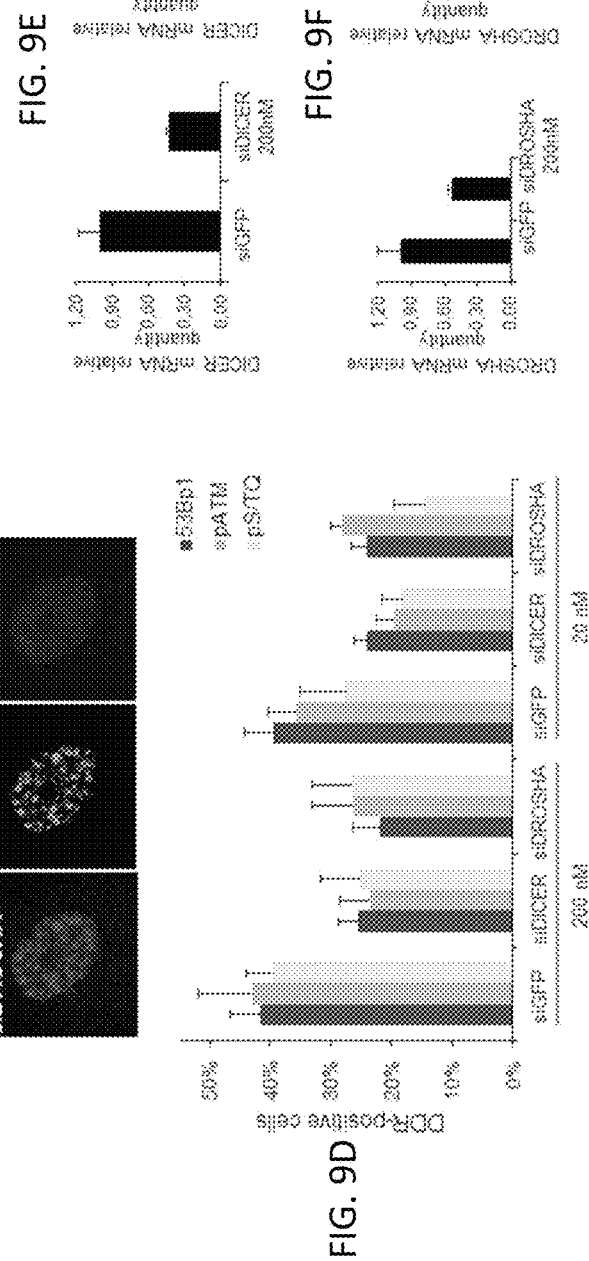

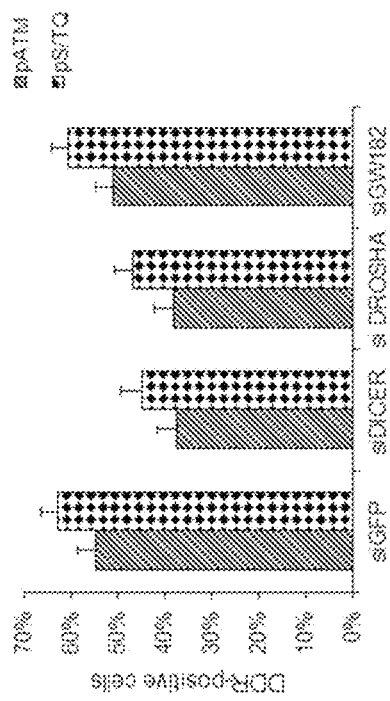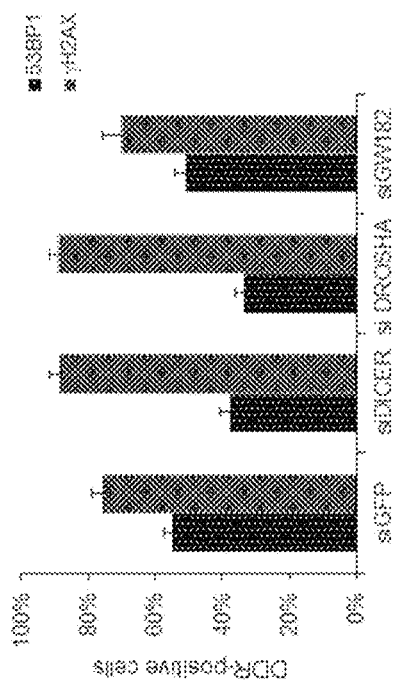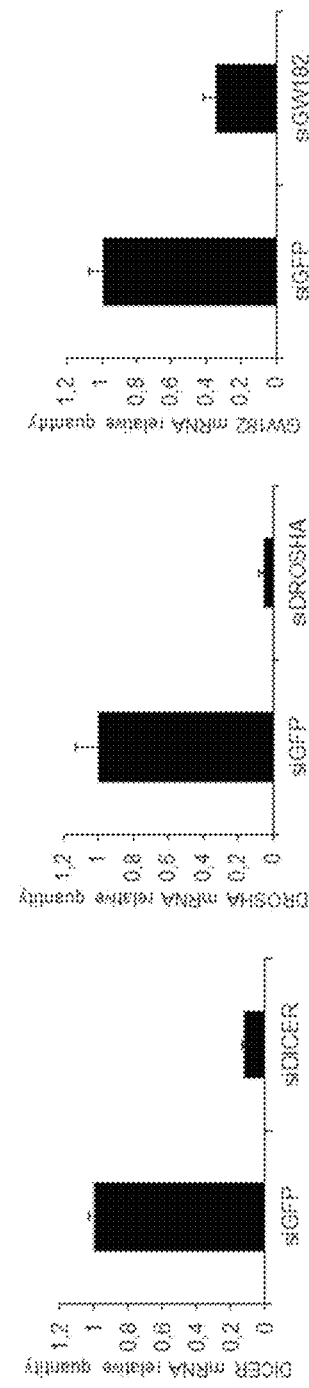
FIG. 14A
FIG. 14B
FIG. 14C

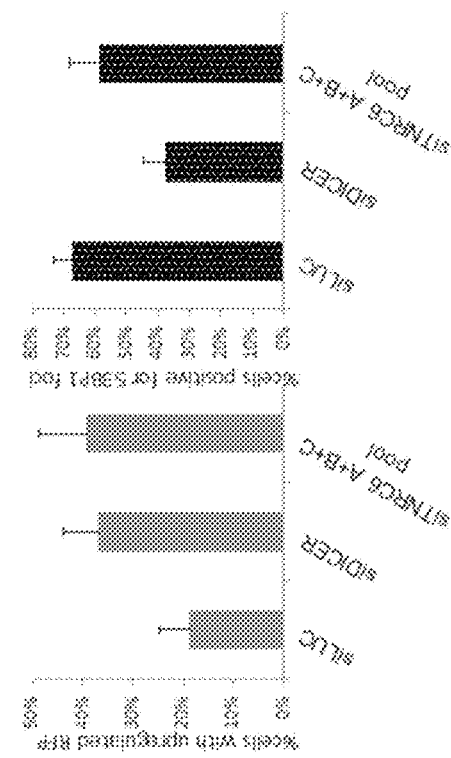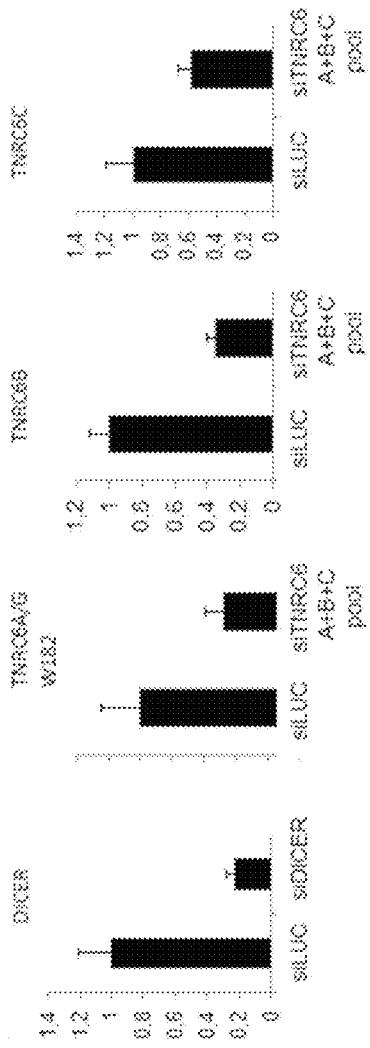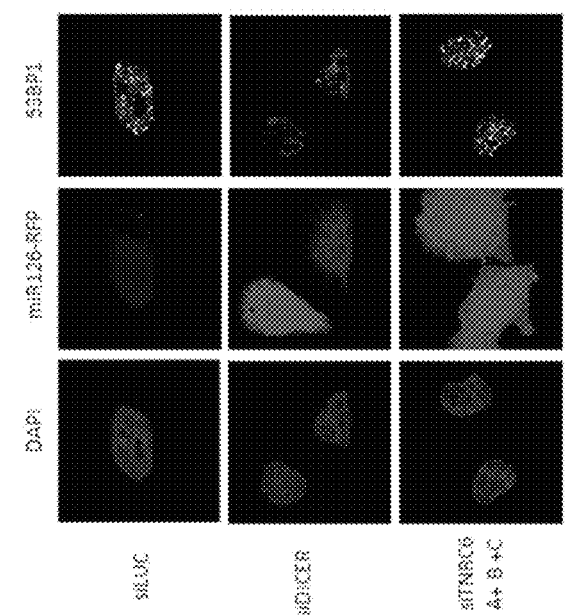
FIG. 15A, FIG. 15B, FIG. 15C, FIG. 15D

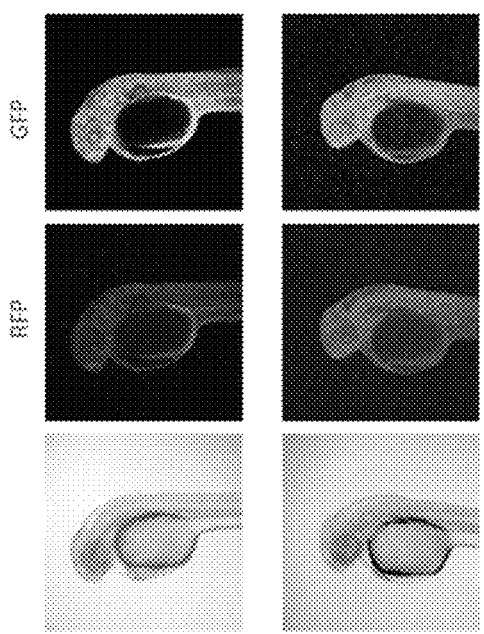
FIG. 21A
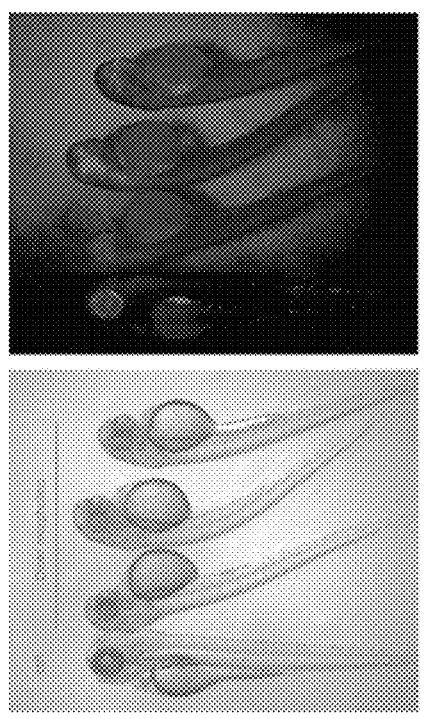
FIG. 21B
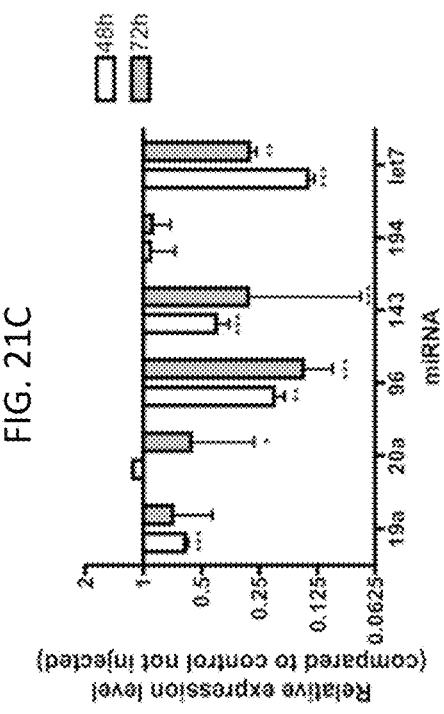
FIG. 21C
FIG. 21D

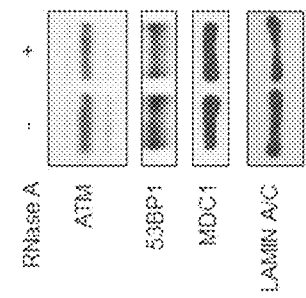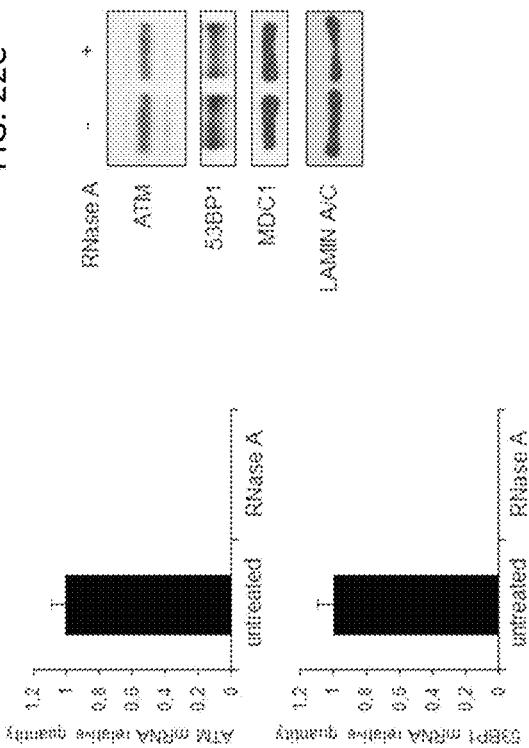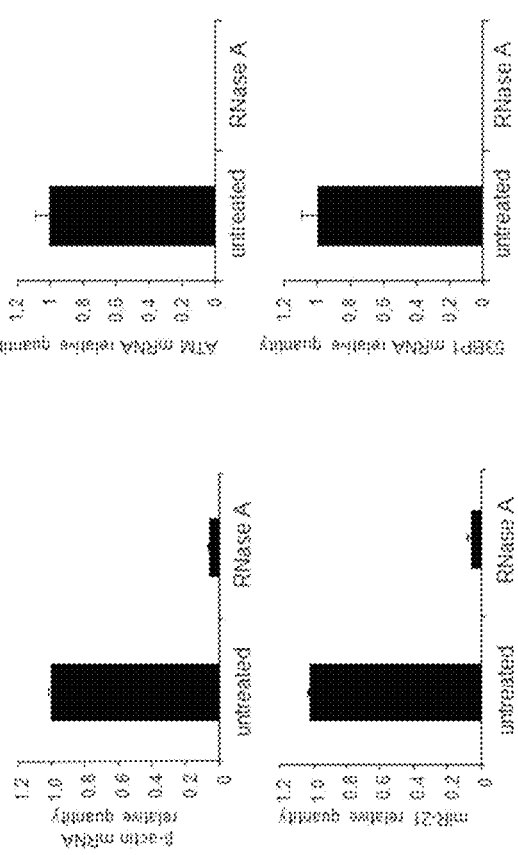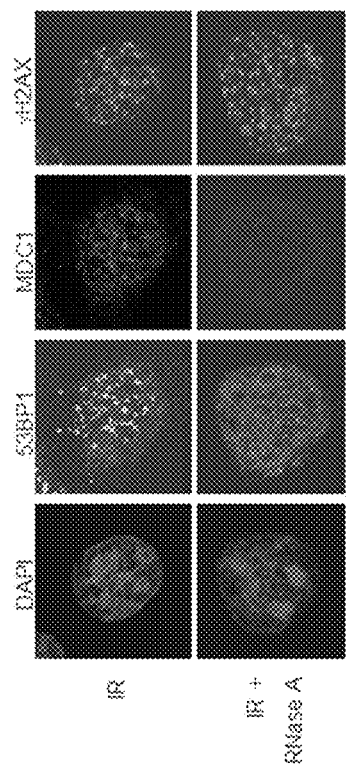

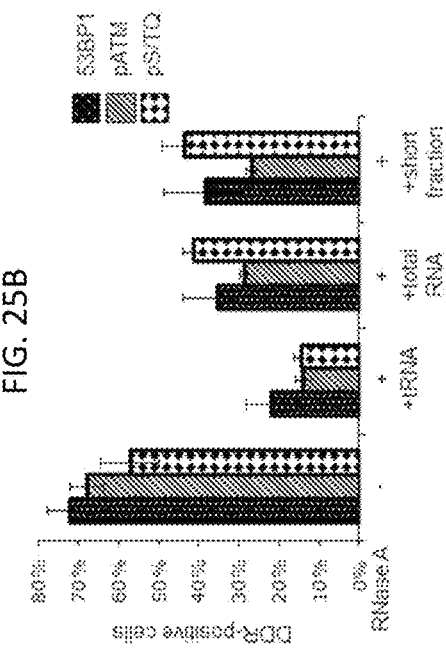
FIG. 25A
FIG. 25B
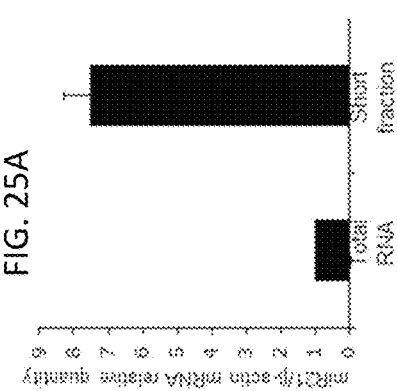
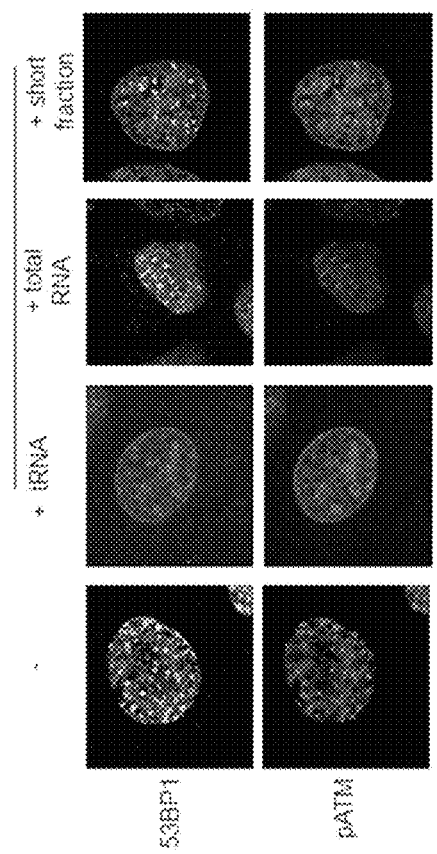
FIG. 25C

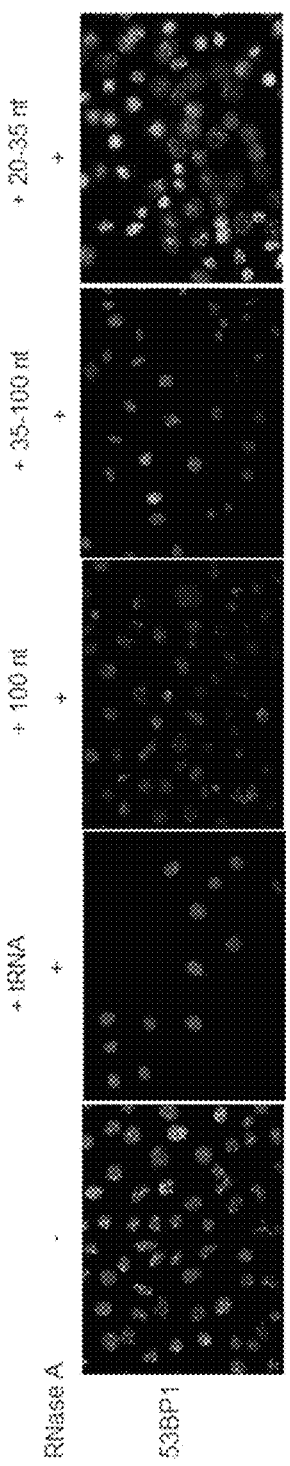
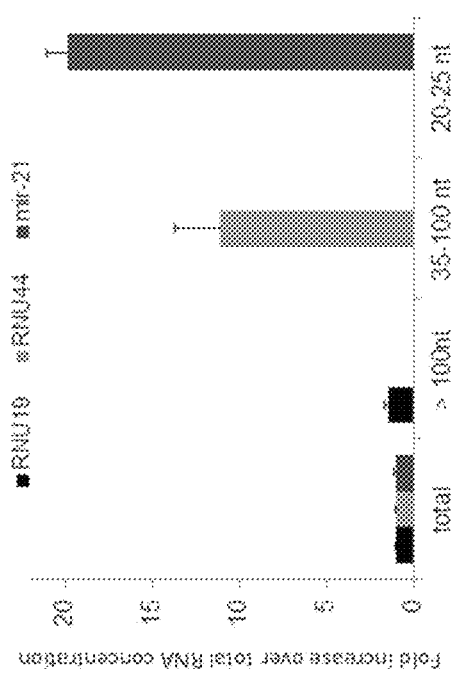
FIG. 26A
FIG. 26B

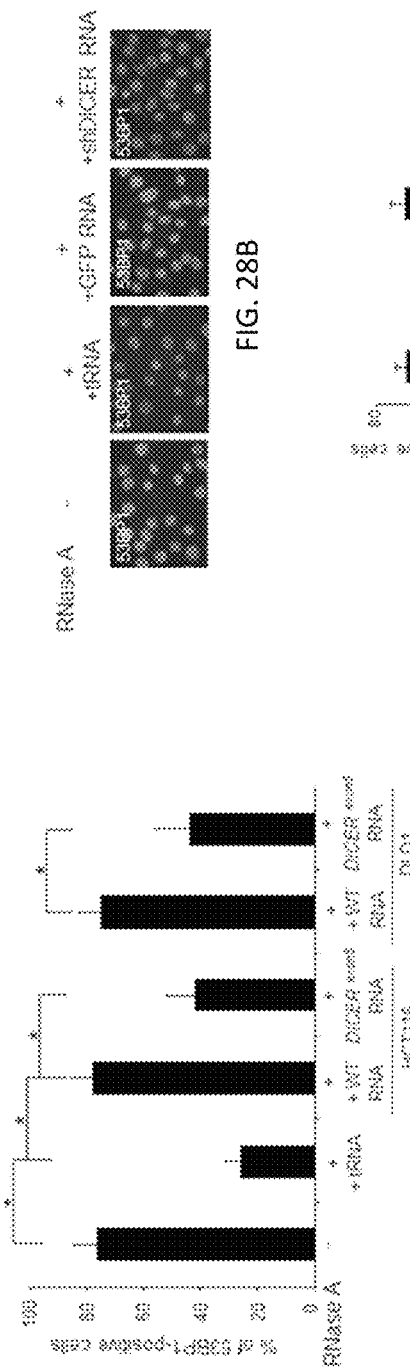
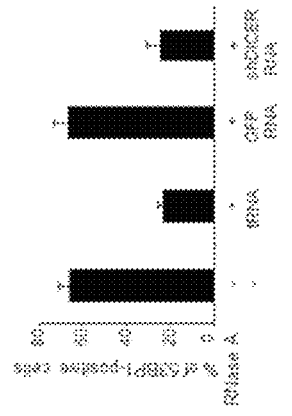
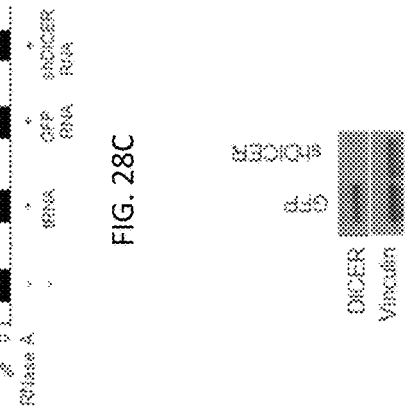
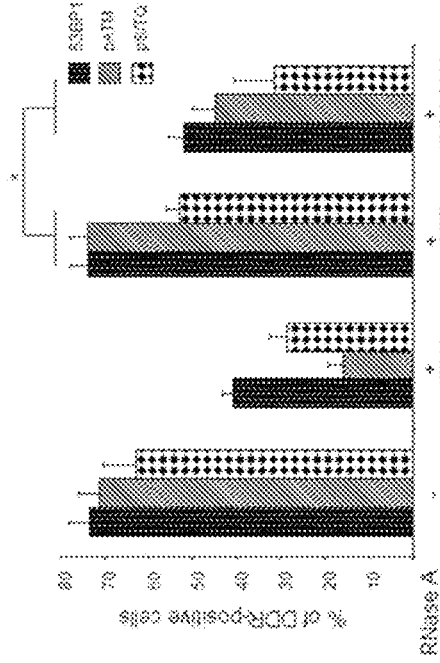
FIG. 28A
FIG. 28B
FIG. 28C
FIG. 28D
FIG. 28E

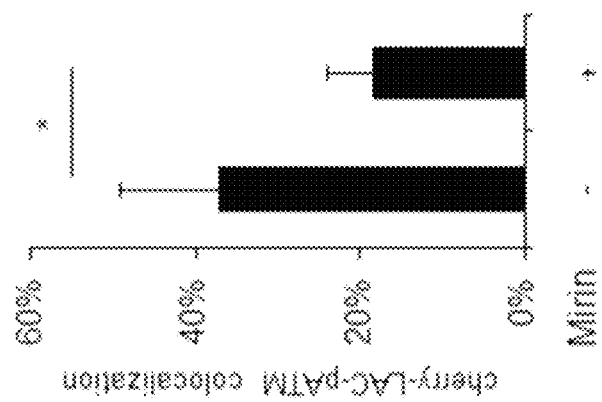
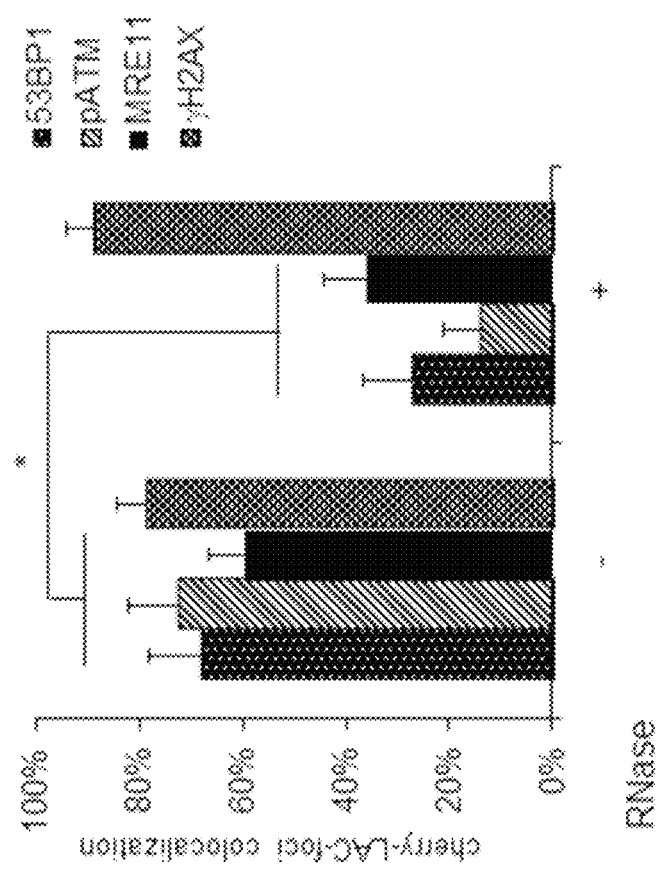
FIG. 29A
FIG. 29B

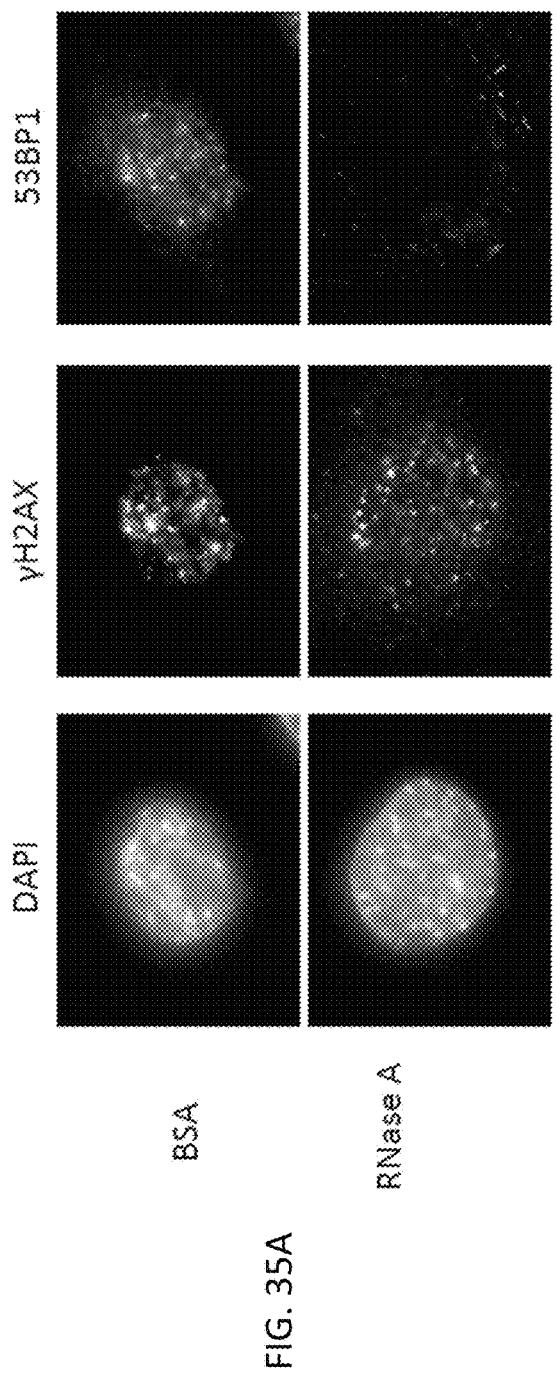
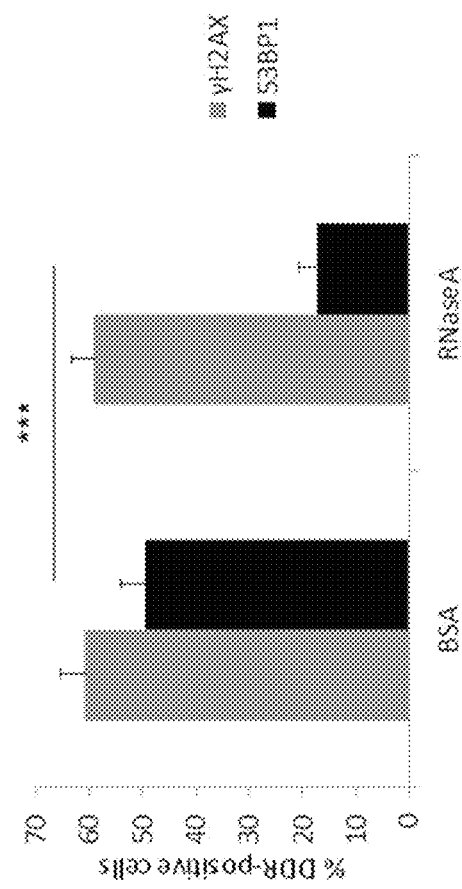
FIG. 35A
FIG. 35B

SEQUENCE LISTING

<160> NUMBER OF SEQ ID NOS: 62

<210> SEQ ID NO 1
<211> LENGTH: 58
<212> TYPE: DNA
<213> ORGANISM: Artificial Sequence
<220> FEATURE:
<223> OTHER INFORMATION: synthetic

<400> SEQUENCE: 1
ccggccacac atcttcaaga cttaactcga gttaagtctt gaagatgtgt ggttttg    58

<210> SEQ ID NO 2
<211> LENGTH: 22

<212> TYPE: DNA
<213> ORGANISM: Artificial Sequence
<220> FEATURE:
<223> OTHER INFORMATION: synthetic

<400> SEQUENCE: 2
agtagattac cactggagtc tt                                          22

<210> SEQ ID NO 3
<211> LENGTH: 57
<212> TYPE: DNA
<213> ORGANISM: Artificial Sequence
<220> FEATURE:
<223> OTHER INFORMATION: synthetic

<400> SEQUENCE: 3
ccgggcctca cttgacctga agtatctcga gatacttcag gtcaagtgag gctttt     57

<210> SEQ ID NO 4
<211> LENGTH: 58
<212> TYPE: DNA
<213> ORGANISM: Artificial Sequence
<220> FEATURE:
<223> OTHER INFORMATION: synthetic

<400> SEQUENCE: 4
ccggcctgga atatgtccac actttctcga gaaagtgtgg acatattcca ggttttg    58

<210> SEQ ID NO 5
<211> LENGTH: 19
<212> TYPE: RNA
<213> ORGANISM: Artificial Sequence
<220> FEATURE:
<223> OTHER INFORMATION: synthetic

<400> SEQUENCE: 5
gagagcagau gauccuuua                                              19

<210> SEQ ID NO 6
<211> LENGTH: 19
<212> TYPE: RNA
<213> ORGANISM: Artificial Sequence
<220> FEATURE:
<223> OTHER INFORMATION: synthetic

<400> SEQUENCE: 6
ggacaagucu cucagcuau                                              19

<210> SEQ ID NO 7
<211> LENGTH: 19
<212> TYPE: RNA
<213> ORGANISM: Artificial Sequence
<220> FEATURE:
<223> OTHER INFORMATION: synthetic

<400> SEQUENCE: 7
gauaucagcu uagacaauu                                              19

<210> SEQ ID NO 8
<211> LENGTH: 19
<212> TYPE: RNA
<213> ORGANISM: Artificial Sequence
<220> FEATURE:
<223> OTHER INFORMATION: synthetic

<400> SEQUENCE: 8
ggacagaacc cgcagauuu                      19

<210> SEQ ID NO 9
<211> LENGTH: 19
<212> TYPE: RNA
<213> ORGANISM: Artificial Sequence
<220> FEATURE:
<223> OTHER INFORMATION: synthetic

<400> SEQUENCE: 9
gaauguugcu uucugaauu                      19

<210> SEQ ID NO 10
<211> LENGTH: 19
<212> TYPE: RNA
<213> ORGANISM: Artificial Sequence
<220> FEATURE:
<223> OTHER INFORMATION: synthetic

<400> SEQUENCE: 10
agacagaauu cccaaauaa                      19

<210> SEQ ID NO 11
<211> LENGTH: 19
<212> TYPE: RNA
<213> ORGANISM: Artificial Sequence
<220> FEATURE:
<223> OTHER INFORMATION: synthetic

<400> SEQUENCE: 11
uauaucaccu guuuguuag                      19

<210> SEQ ID NO 12
<211> LENGTH: 19
<212> TYPE: RNA
<213> ORGANISM: Artificial Sequence
<220> FEATURE:
<223> OTHER INFORMATION: synthetic

<400> SEQUENCE: 12
aggaggagcu ugggccuuu                      19

<210> SEQ ID NO 13
<211> LENGTH: 19
<212> TYPE: RNA
<213> ORGANISM: Artificial Sequence
<220> FEATURE:
<223> OTHER INFORMATION: synthetic

<400> SEQUENCE: 13
uaaaguagcu ggaaugaug                      19

<210> SEQ ID NO 14
<211> LENGTH: 19
<212> TYPE: RNA
<213> ORGANISM: Artificial Sequence
<220> FEATURE:
<223> OTHER INFORMATION: synthetic

<400> SEQUENCE: 14
ggaagaggcu gacuaugaa                      19

<210> SEQ ID NO 15
<211> LENGTH: 19
<212> TYPE: RNA
<213> ORGANISM: Artificial Sequence

```
<220> FEATURE:
<223> OTHER INFORMATION: synthetic

<400> SEQUENCE: 15
gaauaucgau ccuauguuc                                                  19

<210> SEQ ID NO 16
<211> LENGTH: 19
<212> TYPE: RNA
<213> ORGANISM: Artificial Sequence
<220> FEATURE:
<223> OTHER INFORMATION: synthetic

<400> SEQUENCE: 16
gauccuaugu ucaaucuaa                                                  19

<210> SEQ ID NO 17
<211> LENGTH: 19
<212> TYPE: RNA
<213> ORGANISM: Artificial Sequence
<220> FEATURE:
<223> OTHER INFORMATION: synthetic

<400> SEQUENCE: 17
caacauagac uacacgauu                                                  19

<210> SEQ ID NO 18
<211> LENGTH: 19
<212> TYPE: RNA
<213> ORGANISM: Artificial Sequence
<220> FEATURE:
<223> OTHER INFORMATION: synthetic

<400> SEQUENCE: 18
ccaacucccu cgaggauua                                                  19

<210> SEQ ID NO 19
<211> LENGTH: 19
<212> TYPE: RNA
<213> ORGANISM: Artificial Sequence
<220> FEATURE:
<223> OTHER INFORMATION: synthetic

<400> SEQUENCE: 19
ggccaacugu uauagaaua                                                  19

<210> SEQ ID NO 20
<211> LENGTH: 19
<212> TYPE: RNA
<213> ORGANISM: Artificial Sequence
<220> FEATURE:
<223> OTHER INFORMATION: synthetic

<400> SEQUENCE: 20
gaguaggcuu cgugacuua                                                  19

<210> SEQ ID NO 21
<211> LENGTH: 19
<212> TYPE: RNA
<213> ORGANISM: Artificial Sequence
<220> FEATURE:
<223> OTHER INFORMATION: synthetic

<400> SEQUENCE: 21
gaaaugcucu gguccgcua                                                  19
```

```
<210> SEQ ID NO 22
<211> LENGTH: 19
<212> TYPE: RNA
<213> ORGANISM: Artificial Sequence
<220> FEATURE:
<223> OTHER INFORMATION: synthetic

<400> SEQUENCE: 22
gccuaaauau uggugauua                                                19

<210> SEQ ID NO 23
<211> LENGTH: 19
<212> TYPE: RNA
<213> ORGANISM: Artificial Sequence
<220> FEATURE:
<223> OTHER INFORMATION: synthetic

<400> SEQUENCE: 23
gcacugcccu gauccgaua                                                19

<210> SEQ ID NO 24
<211> LENGTH: 19
<212> TYPE: RNA
<213> ORGANISM: Artificial Sequence
<220> FEATURE:
<223> OTHER INFORMATION: synthetic

<400> SEQUENCE: 24
ggaauuaagu cgucgucau                                                19

<210> SEQ ID NO 25
<211> LENGTH: 19
<212> TYPE: RNA
<213> ORGANISM: Artificial Sequence
<220> FEATURE:
<223> OTHER INFORMATION: synthetic

<400> SEQUENCE: 25
cuauuaaccu cgccaauua                                                19

<210> SEQ ID NO 26
<211> LENGTH: 19
<212> TYPE: RNA
<213> ORGANISM: Artificial Sequence
<220> FEATURE:
<223> OTHER INFORMATION: synthetic

<400> SEQUENCE: 26
gguaaguccu ccauugaug                                                19

<210> SEQ ID NO 27
<211> LENGTH: 19
<212> TYPE: RNA
<213> ORGANISM: Artificial Sequence
<220> FEATURE:
<223> OTHER INFORMATION: synthetic

<400> SEQUENCE: 27
ccgugaaagu uuaacguuu                                                19

<210> SEQ ID NO 28
<211> LENGTH: 21
<212> TYPE: RNA
<213> ORGANISM: Artificial Sequence
<220> FEATURE:
<223> OTHER INFORMATION: synthetic
```

```
<400> SEQUENCE: 28
aacacuuguc acuacuuucu c                                    21

<210> SEQ ID NO 29
<211> LENGTH: 23
<212> TYPE: DNA
<213> ORGANISM: Artificial Sequence
<220> FEATURE:
<223> OTHER INFORMATION: synthetic

<400> SEQUENCE: 29
cauucuaucc ucuagaggau gtt                                  23

<210> SEQ ID NO 30
<211> LENGTH: 23
<212> TYPE: DNA
<213> ORGANISM: Artificial Sequence
<220> FEATURE:
<223> OTHER INFORMATION: synthetic

<400> SEQUENCE: 30
ttguaagaua ggagaucucc uac                                  23

<210> SEQ ID NO 31
<211> LENGTH: 18
<212> TYPE: DNA
<213> ORGANISM: Artificial Sequence
<220> FEATURE:
<223> OTHER INFORMATION: synthetic

<400> SEQUENCE: 31
ttcattgtgg gagcagac                                        18

<210> SEQ ID NO 32
<211> LENGTH: 18
<212> TYPE: DNA
<213> ORGANISM: Artificial Sequence
<220> FEATURE:
<223> OTHER INFORMATION: synthetic

<400> SEQUENCE: 32
cagcagtttc tccagagc                                        18

<210> SEQ ID NO 33
<211> LENGTH: 24
<212> TYPE: DNA
<213> ORGANISM: Artificial Sequence
<220> FEATURE:
<223> OTHER INFORMATION: synthetic

<400> SEQUENCE: 33
agcaacacag agatctcaaa catt                                 24

<210> SEQ ID NO 34
<211> LENGTH: 19
<212> TYPE: DNA
<213> ORGANISM: Artificial Sequence
<220> FEATURE:
<223> OTHER INFORMATION: synthetic

<400> SEQUENCE: 34
gcaaagcagg gcttttcat                                       19

<210> SEQ ID NO 35
```

<211> LENGTH: 20
<212> TYPE: DNA
<213> ORGANISM: Artificial Sequence
<220> FEATURE:
<223> OTHER INFORMATION: synthetic

<400> SEQUENCE: 35
tgttccagga agaccaggtt                                              20

<210> SEQ ID NO 36
<211> LENGTH: 23
<212> TYPE: DNA
<213> ORGANISM: Artificial Sequence
<220> FEATURE:
<223> OTHER INFORMATION: synthetic

<400> SEQUENCE: 36
actatccctc aaacactctg gaa                                          23

<210> SEQ ID NO 37
<211> LENGTH: 20
<212> TYPE: DNA
<213> ORGANISM: Artificial Sequence
<220> FEATURE:
<223> OTHER INFORMATION: synthetic

<400> SEQUENCE: 37
ggcccgagag cctttttatag                                             20

<210> SEQ ID NO 38
<211> LENGTH: 22
<212> TYPE: DNA
<213> ORGANISM: Artificial Sequence
<220> FEATURE:
<223> OTHER INFORMATION: synthetic

<400> SEQUENCE: 38
tgcacacgtc taactcttcc ac                                           22

<210> SEQ ID NO 39
<211> LENGTH: 20
<212> TYPE: DNA
<213> ORGANISM: Artificial Sequence
<220> FEATURE:
<223> OTHER INFORMATION: synthetic

<400> SEQUENCE: 39
cagccagtca gaaagcagtg                                              20

<210> SEQ ID NO 40
<211> LENGTH: 23
<212> TYPE: DNA
<213> ORGANISM: Artificial Sequence
<220> FEATURE:
<223> OTHER INFORMATION: synthetic

<400> SEQUENCE: 40
tgtgagtcca ggatctgcta ctt                                          23

<210> SEQ ID NO 41
<211> LENGTH: 20
<212> TYPE: DNA
<213> ORGANISM: Artificial Sequence
<220> FEATURE:
<223> OTHER INFORMATION: synthetic

<400> SEQUENCE: 41

-continued gcaaggaatg gactctgagc                                            20

<210> SEQ ID NO 42
<211> LENGTH: 21
<212> TYPE: DNA
<213> ORGANISM: Artificial Sequence
<220> FEATURE:
<223> OTHER INFORMATION: synthetic

<400> SEQUENCE: 42
ggggacttcg atatcctctt c                                          21

<210> SEQ ID NO 43
<211> LENGTH: 25
<212> TYPE: DNA
<213> ORGANISM: Artificial Sequence
<220> FEATURE:
<223> OTHER INFORMATION: synthetic

<400> SEQUENCE: 43
cgtctctaga aaggtcctac aagaa                                      25

<210> SEQ ID NO 44
<211> LENGTH: 20
<212> TYPE: DNA
<213> ORGANISM: Artificial Sequence
<220> FEATURE:
<223> OTHER INFORMATION: synthetic

<400> SEQUENCE: 44
ggctcaggag caactggtaa                                            20

<210> SEQ ID NO 45
<211> LENGTH: 24
<212> TYPE: RNA
<213> ORGANISM: Artificial Sequence
<220> FEATURE:
<223> OTHER INFORMATION: synthetic

<400> SEQUENCE: 45
auaacaauuu guggaauucg gcgc                                       24

<210> SEQ ID NO 46
<211> LENGTH: 22
<212> TYPE: RNA
<213> ORGANISM: Artificial Sequence
<220> FEATURE:
<223> OTHER INFORMATION: synthetic

<400> SEQUENCE: 46
cgaauuccac aaauuguuau cc                                         22

<210> SEQ ID NO 47
<211> LENGTH: 32
<212> TYPE: RNA
<213> ORGANISM: Artificial Sequence
<220> FEATURE:
<223> OTHER INFORMATION: synthetic

<400> SEQUENCE: 47
auuuguggaa uucggcgccu cuagagucga gg                              32

<210> SEQ ID NO 48
<211> LENGTH: 17
<212> TYPE: RNA

```
<213> ORGANISM: Artificial Sequence
<220> FEATURE:
<223> OTHER INFORMATION: synthetic

<400> SEQUENCE: 48
ccucgacucu agaggcg                                                   17

<210> SEQ ID NO 49
<211> LENGTH: 30
<212> TYPE: RNA
<213> ORGANISM: Artificial Sequence
<220> FEATURE:
<223> OTHER INFORMATION: synthetic

<400> SEQUENCE: 49
agcggauaac aauuuguggc cacaugugga                                     30

<210> SEQ ID NO 50
<211> LENGTH: 17
<212> TYPE: RNA
<213> ORGANISM: Artificial Sequence
<220> FEATURE:
<223> OTHER INFORMATION: synthetic

<400> SEQUENCE: 50
uguggccaca aauuguu                                                   17

<210> SEQ ID NO 51
<211> LENGTH: 32
<212> TYPE: RNA
<213> ORGANISM: Artificial Sequence
<220> FEATURE:
<223> OTHER INFORMATION: synthetic

<400> SEQUENCE: 51
acucccuauc agugauagag aaaagugaaa gu                                  32

<210> SEQ ID NO 52
<211> LENGTH: 32
<212> TYPE: RNA
<213> ORGANISM: Artificial Sequence
<220> FEATURE:
<223> OTHER INFORMATION: synthetic

<400> SEQUENCE: 52
cuuucacuuu ucucuaucac ugauagggag ug                                  32

<210> SEQ ID NO 53
<211> LENGTH: 21
<212> TYPE: RNA
<213> ORGANISM: Artificial Sequence
<220> FEATURE:
<223> OTHER INFORMATION: synthetic

<400> SEQUENCE: 53
guucagcgug uccggcgagu u                                              21

<210> SEQ ID NO 54
<211> LENGTH: 21
<212> TYPE: RNA
<213> ORGANISM: Artificial Sequence
<220> FEATURE:
<223> OTHER INFORMATION: synthetic

<400> SEQUENCE: 54
cucgccggac acgcugaacu u                                              21
```

<210> SEQ ID NO 55
<211> LENGTH: 73
<212> TYPE: DNA
<213> ORGANISM: Artificial Sequence
<220> FEATURE:
<223> OTHER INFORMATION: synthetic

<400> SEQUENCE: 55
gcattattac tcacggtacg aataaggcat tattactcac ggtacgaata aggcattatt    60
actcacggta cga                                                      73

<210> SEQ ID NO 56
<211> LENGTH: 73
<212> TYPE: DNA
<213> ORGANISM: Artificial Sequence
<220> FEATURE:
<223> OTHER INFORMATION: synthetic

<400> SEQUENCE: 56
cgtaataatg agtgccatgc ttattccgta ataatgagtg ccatgcttat tccgtaataa    60
tgagtgccat gct                                                      73

<210> SEQ ID NO 57
<211> LENGTH: 22
<212> TYPE: DNA
<213> ORGANISM: Artificial Sequence
<220> FEATURE:
<223> OTHER INFORMATION: synthetic

<400> SEQUENCE: 57
ttatccgctc acaattccac at                                            22

<210> SEQ ID NO 58
<211> LENGTH: 22
<212> TYPE: DNA
<213> ORGANISM: Artificial Sequence
<220> FEATURE:
<223> OTHER INFORMATION: synthetic

<400> SEQUENCE: 58
atgtggaatt gtgagcggat aa                                            22

<210> SEQ ID NO 59
<211> LENGTH: 21
<212> TYPE: DNA
<213> ORGANISM: Artificial Sequence
<220> FEATURE:
<223> OTHER INFORMATION: synthetic

<400> SEQUENCE: 59
actgataggg agtggtaaac t                                             21

<210> SEQ ID NO 60
<211> LENGTH: 21
<212> TYPE: DNA
<213> ORGANISM: Artificial Sequence
<220> FEATURE:
<223> OTHER INFORMATION: synthetic

<400> SEQUENCE: 60
agagaaaagt gaaagtcgag t                                             21

<210> SEQ ID NO 61

```
<211> LENGTH: 21
<212> TYPE: DNA
<213> ORGANISM: Artificial Sequence
<220> FEATURE:
<223> OTHER INFORMATION: synthetic

<400> SEQUENCE: 61
ccctaaccct aaccctaacc c                                              21

<210> SEQ ID NO 62
<211> LENGTH: 21
<212> TYPE: DNA
<213> ORGANISM: Artificial Sequence
<220> FEATURE:
<223> OTHER INFORMATION: synthetic

<400> SEQUENCE: 62
gggttagggt tagggttagg g                                              21
```

RNA PRODUCTS AND USES THEREOF

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present invention relates to small RNAs (DDRNAs), inhibitors thereof, inhibitors of enzymes producing thereof, and their use to modulate the response of a cell to a DNA damaging event. The invention concerns also a method to detect the presence or quantify DNA damage.

BACKGROUND ART

The DNA damage response (DDR) is a coordinate set of events that promptly follows the generation of a lesion in the DNA double helix. Detection of DNA discontinuities by specialized factors initiates a signaling cascade that, stemming from the site of DNA damage, amplifies the signal and reaches the whole nuclear space and the entire cell[1]. DDR signaling cascade initiation establishes a local self-feeding loop that leads to focal accumulation of upstream DDR factors in the form of cytologically detectable DDR foci at damaged sites. Specifically, detection of a DNA double-strand break (DSB) triggers the activity of the protein kinase ATM that, among other factors, phosphorylates the histone variant H2AX (γH2AX) at the DNA damage site. This modification recruits DDR-mediators like MDC1 and 53BP1 that boost ATM activity. DDR activation can be triggered by exogenous DNA damaging agents such as ionizing radiations and chemotherapeutic agents (i.e. including but not limited to bleomycin) and by endogenous physiological events such as meiotic recombination, V(D)J recombination at the immunoglobulins and T cell receptor loci, telomere shortening and reactive oxygen species, as well as pathological events such as oncogene activation, viral integration in the genome, viral replication and bacterial infection [1,82]. Telomeres dysfunction and oncogene activation can generate a sustained DDR leading to a permanent cell-cycle arrest known as cellular senescence[2]. Recently also bacteria have been shown to generate persistent DNA damage and cellular senescence in mammals [82]. Several pathologies associated with altered telomere functions have been reported as "telomeropathies"[85].

It has recently been appreciated that mammalian genomes are pervasively transcribed and the vast majority of DNA sequences can be found in primary, often overlapping, transcripts most of which apparently not associated with coding functions [3]. These non-coding RNAs (ncRNAs) may remain associated with chromatin, and some aggregate in subnuclear structures such as speckles and paraspeckles[4]. An unsuspected increasing number of these ncRNA transcripts have been shown to be evolutionarily conserved among related species[5,6] and play a variety of relevant cellular functions by regulating the localization and the activity of proteins and/or providing structural support for cellular and sub-cellular structures[7] and controlling chromatin-modification[4,8] and enhancer-like functions[9]. These activities may be exerted despite estimated very low levels of expression, few molecules per cell, for some of these RNA molecules[10,11,12,13]. Some ncRNAs may be processed by ribonucleases of the RNA interference (RNAi) pathway, giving rise to short double-stranded RNA products that participate in various cellular functions. The RNAi pathway is a conserved machinery, whose components are thought to have evolved to preserve genome integrity from the attacks of viruses and mobile genetic elements[14]. It involves different types of short double-stranded RNA molecules including small interfering RNAs (siRNAs), microRNAs, repeat-associated small interfering RNAs (rasiRNAs), Piwi-interacting RNAs (piRNAs)[15] and QDE-2 interacting RNAs (qiRNA) in Neurospora crassa[16]. It is commonly thought that only microRNA maturation is dependent on both DROSHA and DICER endonucleases, two RNase type III enzymes that process hairpin structures to generate double-stranded microRNAs[17]. In mammals, microRNAs modulate gene expression usually by their ability to regulate mRNA translation and stability and have been involved in several processes such as cell fate determination, transformation, proliferation and cell death[18]. piRNAs and qiRNAs have been implicated in genome stability maintenance[16] and a family of microRNAs (miR-34) has been shown to act downstream of p53[19]. It is presently unknown whether any RNAs have any direct role in the control of DDR activation at sites of DNA damage.

US2006105384 is focused on a technique for detecting and diagnosing disease conditions, as well as health conditions due to exposure to environmental conditions by detecting and identifying DNA or RNA damage markers. This technique is based on measurement of free levels of nucleotide excision products resulting from DNA or RNA damage. The DDRNAs of the instant invention are not nucleotide excision products.

JP2009171895 concerns a method for analyzing the function of a non-coding RNA (ncRNA) existing in a nucleus by destroying the ncRNA by introducing an antisense oligomolecule containing substantially the same sequence as a sequence complementary to a single-stranded region in the secondary structure of the target ncRNA to a cell nucleus and destroying the RNA molecule.

WO2012/013821 relates to the field of cancer, particularly cancers wherein p53 tumour suppression function is lost or impaired. It is shown herein that Dicer is a synthetic lethal partner of p53, allowing the selective targeting and killing of cancer cells. The effects of Dicer on survival on cancer cells are mediated through the miR17-92 cluster and inhibition of members of this miRNA cluster is an attractive treatment strategy in cancer. Most particularly, these findings are of importance in the field of retinoblastoma.

WO2011/157294 relates to compositions comprising an inhibitor of a polynucleotide, said polynucleotide to be inhibited being capable of decreasing or suppressing expression of Dicer or a biologically active derivative thereof for use in treating or preventing cancer, metastasis, heart failure, cardiac remodelling, dilated cardiomyopathy, autoimmune diseases, or diseases or disorders related thereto. Furthermore, the present invention also relates to methods of treating or preventing cancer, metastasis, heart failure, cardiac remodelling, dilated cardiomyopathy, autoimmune diseases, or diseases or disorders related thereto. DDRNAs are not mentioned nor the impact of Dicer modulation on DNA damage related events and DDR modulation.

WO2009/102225 relates to compositions and methods for cancer diagnosis, research and therapy, including but not limited to, cancer markers. In particular, the present invention relates to ncRNAs as diagnostic markers and clinical targets for prostate, lung, breast and pancreatic cancer.

US2012289581 relates to long non-coding RNAs (lncR-NAs) and methods of using them diagnostically and therapeutically for treatment of cancer, stem cell therapy, or regenerative medicine are disclosed. In particular, the invention relates to lncRNAs that play roles in regulation of genes involved in cell proliferation, differentiation, and apoptosis. Such lncRNAs can be used as biomarkers to monitor cell proliferation and differentiation during cancer progression or tissue regeneration. One of the identified lncRNAs, referred to as PANDA (a P21-Associated NcRNA, DNA damage Activated), inhibits the expression of apoptotic genes normally activated by the transcription factor NF-YA. Inhibitors of PANDA sensitize cancerous cells to chemotherapy and can be used in combination with chemotherapeutic agents for treatment of cancer.

Limmer K et al. (2013) used a Molecular Force Assay (MFA) to measure the activity of Dicer. As a model system, they used an RNA sequence that forms an aptamer-binding site for paromomycin, a 615-dalton aminoglycoside. They have shown that Dicer activity is modulated as a function of concentration and incubation time: the addition of paromomycin leads to a decrease of Dicer activity according to the amount of ligand. The measured dissociation constant of paromomycin to its aptamer was found to agree well with literature values. The parallel format of the MFA allows a large-scale search and analysis for ligands for any RNA sequence.

Wei et al, (2012) reports the existence in plants and in a human cancer cell line of small RNAs, named diRNAs, generated in proximity to DNA DSB sites[81]. The authors show that genetic inactivation of Dicer-like RNA endonucleases results in a specific defect in DNA repair by homologous recombination. Authors observe some correlation between diRNAs accumulation and DNA repair by homologous recombination, and propose that diRNAs control DNA repair. However there is no support by the data shown in the article by Wei et al. to such hypothesis. As a matter of fact there is no evidence that diRNA play a biologically active role in the process of DNA repair. Prior art data in Wei et al are not in contrast with diRNAs being generated following the degradation of a RNA transcript spanning the DSB site.

In addition, it is not demonstrated in the Wei et al article that the proposed effect of the inactivation of Dicer-like genes and DNA repair is not indirect, possibly mediated by canonical RNA interference mechanisms. Although the authors show that the abundance of few DNA repair factors is not affected, it is not demonstrated that other DNA repair factors, not tested by the authors, are unaffected and not targeted by RNA interference mechanisms and thus potentially making an indirect impact on DNA repair.

Finally, correlation is not always maintained and at least in plants the authors show cases in which diRNAs are decreased (FIG. 3a, mutants RDR2 and RDR6) and DNA repair is unaltered (FIG. 3b).

DDRNA of the instant invention have been characterized for distinct functions: DDRNAs control DDR signaling, whereas diRNA of Wei et al are not shown to have any role in DDR signaling: Wei et al show no evidence of altered DDR activation, as detected by nuclear DDR foci formation or of DDR proteins activation, for instance by phosphorylation, or of altered DNA damage checkpoint functions or modulation of cellular senescence. Thus there is no demonstrated overlap between their functions.

In cultured Drososphila cells, Michalik et al.[79], showed that the transfection of a linearized plasmid leads to the generation of short (21 nt) RNAs with the sequence of the plasmid DNA ends. The small RNAs in this system are produced by active transcription of plasmid genes in the vicinity of the break. The function proposed for them was the repression of the marker gene encoded by the plasmid. Inactivation of some of the factors involved in the RNA interference pathway relieves the observed repression. Such effect has been interpreted as RNA interference activity of the short RNAs acting as endo-siRNAs. A causal relation between the production of short RNA and DDR activation or DNA repair is lacking in this study. This set of observation support the notion that small RNA are produced at DNA ends in cultured Drosophila cells, but it does not provide a function of this novel RNA molecule in the DNA damage response pathway.

SUMMARY OF THE INVENTION

DICER (Gene ID: 23405; Official Symbol: DICER1 Name: dicer 1, ribonuclease type III [Homo sapiens] Other Aliases: DCR1, Dicer, HERNA, KIAA0928, MNG1; Other Designations: Dicer1, Dcr-1 homolog; K12H4.8-LIKE; dicer 1, double-stranded RNA25 specific endoribonuclease; endoribonuclease Dicer; helicase MOI; helicase with RNAse motif; helicase-moi, Chromosome: 14; Location: 14q32.13, Annotation: Chromosome 14, NC_000014.8 (95552565 . . . 95623759, complement), MIM: 606241, NCBI version May 4, 2012) and DROSHA (Gene ID: 29102; Official Symbol: DROSHA Name: drosha, ribonuclease type III [Homo sapiens], Other Aliases: ETOHI2, HSA242976, RANSE3L, 30 RN3, RNASE3L, RNASEN; Other Designations: RNase III; drosha, double-stranded RNA-specific endoribonuclease; nuclear RNase III Drosha; p241; protein Drosha; putative protein p241 which interacts with transcription factor Sp1; putative ribonuclease III; ribonuclease 3; ribonuclease III, nuclear; ribonuclease type III, nuclear; Chromosome: 5; Location: 5p13.3, Annotation: Chromosome 5, NC_000005.9 (31400601 . . . 31532282, complement), MIM: 608828, NCBI version May 4, 2012) are crucial ribonucleases involved in RNA interference (RNAi). Components of RNAi are thought to have evolved to preserve genome stability from the attacks of viruses and mobile genetic elements. RNA products generated by DICER and DROSHA are involved in chromatin assembly in Schizosaccharomyces pombe, gene silencing and cancer. The DNA damage response (DDR) is a signaling pathway that arrests the proliferation of cells undergoing genotoxic events to preserve genome stability. So far, RNAi and DDR signaling pathways have not been demonstrated to directly interact. Here the authors show that oncogene-induced senescent cells, cells thus bearing oncogene-induced DNA damage and consequent DDR activation, require DICER and DROSHA to maintain DDR activation and cell-cycle arrest. DICER and DROSHA are also necessary to activate DDR upon exogenous DNA damage, and DDR checkpoint functions depend on the ribonuclease activity of DICER. DICER is required for irradiation-induced DDR activation in vivo in zebrafish. In an in vitro cellular system, DDR foci stability is sensitive to RNase A treatment, and DICER- and DROSHA-dependent small RNA products are required to restore DDR foci in RNase A-treated cells. Study of DDR activation at a DNA double-strand break within a unique and traceable exogenous integrated locus reveals that DDR focus formation requires locus-specific RNA molecules. The authors provide evidence through RNA sequencing that short or small RNAs, that the authors call DDRNAs, originate at the locus and carry the sequence of the damaged locus. When chemically synthesized or generated in vitro by DICER cleavage of transcripts spanning the locus, DDRNAs promote DDR activation at the DNA damage site in RNase A-treated cells also in the absence of other mammalian RNAs. All together, the authors' results reveal an unanticipated direct role of short or small RNAs (DDRNAs) in the control of DDR activation at sites of DNA damage.

DDRNAs act differently from microRNAs and canonical RNAi mechanisms because:
- DDRNAs act without the need for any other cellular RNA (see the results obtained with gel-extracted RNA and synthetic RNAs in RNAse A-treated cells experiments).
- DDRNAs can have a sequence (LAC or TET repeats) that has no endogenous cellular transcripts match and still be biological active
- DDRNAs can act fast (in minutes) at room temperature in cells inhibited for transcription and translation (see the results obtained in RNAse A-treated cells experiments).
- Inactivation of GW proteins (effectors of canonical miRNA) does not affect DDR foci.

It is therefore an object of the present invention a method to inhibit the DNA damage response in a cell damaged in at least one sequence specific genomic locus comprising the step of:
 a) inhibiting the function of small RNAs (DDRNAs), said small RNAs being generated by processing by DICER and/or DROSHA of a RNA transcript synthesized upon transcription of the damaged genomic locus, or impairing the production thereof.

Preferably the method further comprising the step of: b) exposing said cell to a DNA damaging treatment.

Preferably the DNA damaging treatment belongs to the group of: radiotherapy, chemotherapy (i.e. hydroxyurea treatment, bleomycine treatment), a treatment that impairs DNA repair or any genotoxic treatment.

It is another object of the invention a method for sensitizing a cell damaged in at least one sequence specific genomic locus to the effect of a DNA damaging treatment, comprising the step of:
 a) inhibiting the function of small RNAs (DDRNAs), said small RNAs being generated by processing by DICER and/or DROSHA of a RNA transcript synthesized upon transcription of the damaged genomic locus, or impairing the production thereof,
 and
 b) exposing said cell to an effective amount of the DNA damaging treatment, wherein step a) and step b) are performed in any order.

Preferably the DNA damaging treatment is a radiotherapy. Still preferably the radiotherapy is any ionizing radiation.

In a preferred embodiment the cell is damaged in at least one sequence specific genomic locus by a genotoxic event.

Preferably the genotoxic event belongs to the group of: cell transformation, cellular senescence, oncogene activation, DNA replication stress, reactive oxygen species, ionizing radiation, chemotherapeutic agents (i.e. comprising but not limiting to bleomycin), telomere shortening, damaged telomere, recombination including V(D)J recombination at the immunoglobulins and T cell receptor locus, viral integration in the genome, viral infection and replication, bacterial infection.

In a preferred embodiment the step of inhibiting the function of said small RNAs (DDRNAs) is performed by a sequence specific inhibitor molecule.

Preferably the sequence specific inhibitor molecule is a sequence specific oligonucleotide. Still preferably the sequence specific inhibitor oligonucleotide is a LNA molecule.

In a preferred embodiment the step of impairing the production of said small RNAs (DDRNAs) is performed by inhibiting the cleavage and/or helicase activity of DICER and/or DROSHA.

Preferably the inhibitor of the cleavage and/or helicase activity of DICER and/or DROSHA is a specific siRNA.

In a preferred embodiment the cell is a mammalian cell. Preferably a human cell. Yet preferably the cell carries a sequence specific DNA damaged genomic locus.

Still preferably a pre-cancerous cell, a cancer cell, a senescent cell, a cell with damaged telomeres or a viral infected cell. Preferably, the senescent cell has critically short and/or damaged and/or dysfunctional telomeres.

It is a further object of the invention an inhibitor of small RNAs (DDRNAs), said small RNAs being generated by processing by DICER and/or DROSHA of a RNA transcript synthesized upon transcription of a sequence specific damaged genomic locus for medical use.

Preferably the inhibitor is for use in the treatment of a condition induced by the sequence specific damaged genomic locus.

Preferably the condition is cancer and/or aging and/or a viral infection. Preferably aging is associated with critically short and/or damaged and/or dysfunctional telomeres.

In a preferred embodiment the inhibitor is a sequence specific inhibitor molecule. Preferably said sequence specific inhibitor molecule is a sequence specific oligonucleotide. Still preferably said sequence specific inhibitor oligonucleotide is a LNA molecule.

Preferably the inhibitor is an inhibitor of DICER and/or DROSHA. Still preferably the inhibitor is a siRNA.

It is a further object of the invention a pharmaceutical composition comprising the inhibitor as defined above. The pharmaceutical composition comprises carriers, diluents and/or excipients. The composition may be administered by parenteral, oral, intravenous, intranasal, intramuscular route or any suitable route. The pharmaceutical composition mya be administered in any effective amount to elicit the desired therapeutic effect. The composition may be in any forms: solution, tablet, ointment etc.

It is a further object of the invention a method to detect the presence of damage to DNA in a sequence specific genomic locus in a cell comprising the steps of:
 a) detecting the presence of small RNAs (DDRNAs), said small RNAs being generated by processing by DICER and/or DROSHA of a RNA transcript synthesized upon transcription of the damaged genomic locus in said cell;
 b) comparing the result to a control cell with undamaged DNA genomic locus.

It is a further object of the invention a method to identify the genomic location of a damage to DNA in a sequence-specific genomic locus in a cell comprising the steps of:
 a) isolating and/or purifying small RNAs (DDRNAs) from a sample, said small RNAs being generated by processing by DICER and/or DROSHA of a RNA transcript synthesized upon transcription of the damaged genomic locus in said cell;
 b) sequencing said isolated and/or purified small RNAs (DDRNAs).

It is a further object of the invention a method to quantify the DNA damage in a specific genomic locus in a cell comprising the steps of:

a) measuring the amount of small RNAs (DDRNAs), said small RNAs being generated by processing by DICER and/or DROSHA of a RNA transcript synthesized upon transcription of the damaged genomic locus in said cell;

b) comparing the result to a proper control.

It is a further object of the invention a method for the diagnosis and/or prognosis of a condition associated with and/or induced by the generation of DNA damage in at least one sequence specific genomic locus comprising:

a) measuring the amount of small RNAs, said small RNAs being generated by processing by DICER and/or DROSHA of a RNA transcript synthesized upon transcription of the damaged genomic locus in said cell;

b) comparing the result to a proper control.

Preferably the condition associated with and/or induced by the generation of DNA damage in at least one sequence specific genomic locus is selected from the group consisting of: cancer, aging, viral infection. Still preferably aging is associated with critically short and/or damaged and/or dysfunctional telomeres.

It is a further object of the invention a method for monitoring the efficacy of therapy directed to a condition associated with and/or induced by the generation of DNA damage in at least one sequence specific genomic locus in a subject comprising:

a) measuring the amount of small RNAs (DDRNAs), said small RNAs being generated by processing by DICER and/or DROSHA of a RNA transcript synthesized upon transcription of the damaged genomic locus in said cell;

b) comparing the result to a proper control.

Preferably the condition associated with and/or induced by the generation of DNA damage in at least one sequence specific genomic locus is selected from the group consisting of: cancer, aging, viral infection. Still preferably aging is associated with damaged telomeres. In the method for monitoring the efficacy of therapy, the proper control may be an untreated cell, a healthy cell or a cell at various time point during the therapy.

It is a further object of the invention a method of screening for an agent able to inhibit small RNAs (DDRNAs), said small RNAs being generated by processing by DICER and/or DROSHA of a RNA transcript synthesized upon transcription of a damaged genomic locus in a cell comprising the step of measuring the amount of said small RNAs upon exposure of the cell to said agent, and comparing to a proper control.

In the method of screening for an agent able to inhibit small RNAs, the proper control may be a cell treated with a reference compound or a non-treated cell.

In the present invention, DDRNAs are small RNAs, with the potential to form double-stranded pairs, that are generated by processing by DICER and/or DROSHA of a sequence specific RNA transcript synthesized upon transcription of a damaged DNA locus. DDRNAs are small RNAs of a length between 10 and 50 nucleotides. For example of a length between 17 and 32 nucleotides. For example of a length between 20 and 25 nucleotides. For example of a length between 22 and 23 nucleotides.

Said DDRNAs function by favoring the sequence-specific accumulation of DDR factors at specific sites of DNA damage and promote DDR signaling (i.e. comprising but not limiting to protein phosphorylation events).

A critically short telomere is a telomere able to engage the DDR machinery due to its critical short length. A damaged telomere is a telomere carrying a DNA lesion able to engage the DDR machinery. A dysfunctional telomere is a telomere that due to its altered protein and/or nucleic acid structure engages the DDR machinery In the present invention an oncogenic stress may be a genotoxic stress (i.e. comprising but not limiting to DNA lesions, impaired DNA replication forks progression) due to oncogene activation, amplification, gain of function mutation, increased levels and activity. A cell carrying a DNA damage is a cell whose DNA damage is not exogenously induced (i.e. a cell comprising but not limiting to critically short telomere and damaged telomere, oncogenic stress, oxidative DNA damage).

Aging is associated with telomeric DNA damage and DDR activation[2, 84].

Genotoxic treatments commonly used in cancer therapy are treatments associated with the generation of DNA damage (i.e. comprising but not limiting to radiotherapy and chemotherapy).

A radiotherapy is a therapy based on the exposure to ionizing radiation.

An effective dose of ionizing radiation is a dose of ionizing radiation able to generate the desired outcome. The skilled person in the art using common routine techniques knows how to determine such dose.

A senescent cell is a cell retaining persistent DDR activation (usually following oncogenic stress and/or telomere shortening/DNA damage).

The presence of DNA damage is concluded by the presence of said short RNAs (DDRNAs); in the absence of said DDRNAs, it is concluded that cells do not have DNA damage.

In qualitative analysis, control cell may be a non-damaged cell or a healthy cell. The analysis may be carried out by quantitative Reverse Transcriptase-PCR, northern blot hybridization, next generation sequencing (Illumina etc), ion torrent technology or by any other means available, appropriated and known to the skilled person in the art. It may be performed on a cell or the blood or other biological fluids. It can also be performed in tissue lysates.

The quantity of said short RNAs (DDRNAs) is proportional to DNA damage, higher quantities of said RNAs indicate larger amount of DNA damage.

In quantitative analysis, the control may be a non-damaged cell or a healthy cell. The analysis may be carried out by qRT-PCR, northern blot hybridization, next generation sequencing (Illumina etc), ion torrent technology or by any other means available, appropriated and known to the skilled person in the art. It may be performed on a cell or the blood or other biological fluids. It can also be performed in tissue lysates.

In the present invention, "inhibiting DICER and/or DROSHA" means:

1. Inhibiting the enzymatic (nuclease and/or helicase) activity of DICER and/or DROSHA by means of a small molecule compound and/or;
2. Inhibiting the synthesis of DICER and/or DROSHA by RNA interference means and/or;
3. Destabilizing the proteins DICER and/or DROSHA by targeting by various means protein cofactors that bind and are necessary for DICER and/or DROSHA activities and/or;
4. Inhibiting DICER and/or DROSHA activity by the expression of DICER and/or DROSHA alleles with dominant negative functions and/or;
5. Inhibiting DICER and/or DROSHA by targeting the genomic loci responsible for their synthesis.

An inhibitor of DICER and/or DROSHA is able to have at least one of the above activities. In the present invention "inhibiting small RNAs, said small RNAs being generated by processing by DICER and/or DROSHA of a RNA transcript synthesized upon transcription of the damaged genomic locus" means:

1. preventing DDRNAs biogenesis and/or processing by inhibiting DICER and/or DROSHA as described above and/or
2. preventing DDRNAs synthesis by preventing the transcription of the longer RNA precursor eventually cleaved by DICER and/or DROSHA and/or
3. preventing DDRNAs proper localization in the cell to prevent their processing and/or
4. preventing DDRNAs proper localization in the cell to prevent their functions and/or
5. preventing DDRNAs accumulation by increasing their degradation rates and/or
6. preventing DDRNAs functions by the use of a sequence specific inhibitory oligonucleotide able to avidly and specifically bind to DDRNAs. These oligonucleotides comprise but are not limiting to locked nucleic acids (LNA), phosphorothioate modified oligonucleotides, 2'-O-methoxyethyl modified oligonucleotides, 2' O-Methyl modified oligonucleotides, methylphosphonates, morpholino oligonucleotides, LNA-DNA-LNA gapmer oligonucleotides, Chimeric 2'-O-methyl RNA-DNA gapmer, N3'-P5' Phosphoroamidate, 2'-fluoro-arabino nucleic acid, Phosphoroamidate Morpholino, Cyclohexene nucleic acid, Tricyclo-DNA, Peptide nucleic acid, Unlocked nucleic acid, Hexitol nucleic acid, Boranophosphate oligonucleotides, Phosphoroamidate oligonucleotides and/or oligonucleotides expressed by plasmid-encoded genes delivered by different means (comprising but not limited to plasmid transfection, viral infection) and/or
7. preventing DDRNAs functions by modifying them by means i.e. of methylation, and/or
8. preventing any modification of DDRNAs (such as phosphorylation, methylation etc etc . . . ) that may be necessary for their function, stability or localization.

A DICER and/or DROSHA inhibitor is an agent or molecule able to display at least one DICER and/or DROSHA inhibiting function as described above (inhibiting the enzymatic activity of DICER and/or DROSHA, inhibiting the synthesis of DICER and/or DROSHA, destabilizing the proteins DICER and/or DROSHA, inhibiting DICER and/or DROSHA activity by the expression of DICER and/or DROSHA alleles with dominant negative functions and/or; targeting the genomic loci responsible for DICER and/or DROSHA synthesis).

An inhibitor of DDRNAs is an agent or molecule able to display at least one DICER and/or DROSHA inhibiting function as described above (preventing their synthesis, preventing their proper localization in the cell to prevent their processing and/or functions, preventing their accumulation, preventing their functions, preventing them to act as they would and/or preventing any modification of DDRNAs).

The invention will be now described by way of non-limiting examples referring to the following figures.

DESCRIPTION OF THE DRAWINGS

FIG. 1A DICER and DROSHA knockdown by siRNA pools in OIS cells impairs DDR foci maintenance as detected by 53BP1, pATM, pS/TQ, γH2AX immunostaining. FIG. 1B Histograms show quantification of the percentage of cells positive for 53BP1, pATM, pS/TQ and γH2AX or H3K9me3, a marker of SAHF formation. FIG. 1C DICER or DROSHA knockdown by siRNA pools in WI38 human fibroblasts impairs pATM, pS/TQ, MDC1, but not γH2AX, foci assembly. Cells were irradiated (10Gy) and fixed 7 h later. FIG. 1D Histograms show percentage of WI38 cells positive for pATM, pS/TQ, MDC1 and γH2AX foci. FIG. 1E pATM, pS/TQ and MDC1, but not γH2AX, foci formation is impaired in DICER$^{exon5}$-hypomorphic cells. Cells were irradiated (2Gy) and fixed 2 h later. FIG. 1F Histograms show the percentage of cells positive for DDR foci. Error bars indicate s.e.m. (n≥3). Differences (*) are statistically significant (p-value<0.001).

FIGS. 2A-2D|DICER-inactivated cells have impaired G1/S and G2/M checkpoint. FIG. 2A DICER, DROSHA or 53BP1 knockdown by siRNA pools in WI38 impairs irradiation-induced G1/S checkpoint. siGFP was used as control. Cells were irradiated (10Gy) and labeled with BrdU for 7 hours before fixation. Histograms show the percentage of BrdU-positive cells in not-irradiated (−) and in irradiated (+) cells. FIG. 2B DICER$^{exon5}$-hypomorphic cells have impaired G1/S checkpoint. Cells were irradiated (2Gy) and labeled with BrdU for 2 hours before fixation. Histograms show the percentage of BrdU-positive cells in not-irradiated (−) and in irradiated (+) cells. Wild-type DICER-flag cDNA expression restores the G1/S checkpoint while cDNAs of DICER endonuclease mutants DICER44ab-flag and DICER110ab-flag do not. Error bars indicate s.e.m. (n=3). Differences (*) are statistically significant (p-value<0.01). FIG. 2C DICER knocked-down cells have impaired G2/M checkpoint. FACS profiles of HEK293 cells transfected with an shRNA against DICER and p53 at 12, 24 and 36 hours post irradiation (5Gy). shGFP is used as control. FIG. 2D The table shows the percentage of cells in G1, S and G2 phase of the cell cycle at different time points post IR.

FIGS. 3A-3D|Irradiation induces pATM and γH2AX nuclear accumulation in control but not in Dicer1 morpholino-injected zebrafish embryos. FIG. 3A Images illustrating the location of the sections from the head of 3 days post fertilization (dpf) WT (not injected) and Dicer1-morpholino injected zebrafish larvae stained for pATM and γH2AX before and after irradiation (12Gy). Sections were stained with DAPI (blue) and pATM or γH2AX antibody (green). FIG. 3B Immunoblot analysis of pATM and γH2AX accumulation in extracts from not irradiated and irradiated wild-type embryos or Dicer1 morpholino-injected embryos. Total ATM and histone H3 were used as loading control. FIG. 3C Schematic drawing of the transplantation procedure. GFP-positive Dicer1 morpholino transplanted cells, integrated in various locations in the host, show reduced γH2AX signals following IR. FIG. 3D Schematic drawing of the reverse transplantation procedure: control cells from embryos injected with mRNA encoding for GFP were transplanted into Dicer1 morpholino injected embryos. Dicer1-expressing cells display γH2AX signals, while the surrounding Dicer1 morpholino-injected cells do not.

FIG. 4A Irradiated HeLa cells (2Gy) were treated with PBS (−) or RNase A (+) and probed for 53BP1, pATM, pS/TQ, MDC1 and γH2AX foci. 53BP1, pATM, pS/TQ and MDC1, but not γH2AX, foci are strongly reduced upon RNase A treatment. FIG. 4B Histograms report the percentage of cells positive for DDR foci. FIG. 4C Addition of gel-purified RNA in the size range of 20-35 nt allows DDR foci reformation in RNase A-treated cells. RNAs were separated according to their size by acrylamide gel electrophoresis and gel extracted. 100, 50 or 20 ng of gel extracted total RNA and 50 ng of RNA extracted from each gel fraction (>100 nt, 35-100 nt and 20-35 nt) were used for RNA reconstitution post RNase treatment in HeLa cells. Error bars indicate s.e.m. (n=2). Differences are statistically significant (*p-value<0.01). FIG. 4D Irradiation-induced 53BP1, pS/TQ and pATM foci are restored in RNase A-treated cells when incubated with RNA of wild-type (WT RNA) RKO cells but not with RNA of DICER$^{exon5}$-hypomorphic (DICER$^{exon5}$ RNA) RKO cells. tRNA was used as control. γH2AX foci were not affected. FIG. 4E Histograms report the percentage of cells positive for DDR foci. Error bars indicate s.e.m. (n≥4). Differences are statistically significant (*p-value<0.001).

FIGS. 5A-5E|Site-specific DDR focus formation is RNase A-sensitive and can be restored by locus-specific RNA in a MRE11-RAD50-NBS1 complex-dependent manner. FIG. 5A NIH2/4 mouse cells experiencing I-Sce I-induced DSB next to a Lac-operator array (LacO array) display a 53BP1 (green) and γH2AX (magenta) focus colocalizing with the Cherry-Lac focus (red). 53BP1, but not γH2AX focus, is sensitive to RNase A and it is restored by incubation with total RNA. FIG. 5B Histograms show the percentage of cells in which 53BP1 and Cherry-Lac foci co-localize. Addition of 50, 200, 800 ng of RNA purified from NIH2/4 rescues 53BP1 foci formation in a dose-dependent manner. FIG. 5C Incubation of RNase A-treated cells with RNA purified from NIH2/4 expressing I-Sce I restores 53BP1 focus at the I-Sce I induced cut site, while RNA from NIH3T3 parental cells expressing I-Sce I does not. FIG. 5D RNA from NIH2/4 cells, or parental one, was used in RNase A-treated NIH2/4 cells to test 53BP1 focus reformation in the presence of the MRN inhibitor mirin. Cells were pretreated with 100 μM mirin for 15 minutes at room temperature before RNA addition and mirin was kept at the same concentration during incubation with RNA. Both 53BP1 and pATM foci reformation is inhibited by the presence of mirin. Histograms report the percentage of cells positive for DDR foci. Error bars indicate s.e.m. (n≥3). Differences are statistically significant (*p-value<0.05). FIG. 5E RNA from NIH2/4 cells, or parental one, was used in RNase A-treated NIH2/4 cells to test pATM focus reformation in the presence of the MRN inhibitor mirin. Cells were pretreated with 100 μM mirin for 15 minutes at room temperature before RNA addition and mirin was kept at the same concentration during incubation with RNA. Both 53BP1 and pATM foci reformation is inhibited by the presence of mirin. Histograms report the percentage of cells positive for DDR foci. Error bars indicate s.e.m. (n≥3). Differences are statistically significant (*p-value<0.05).

FIGS. 6A-6D|Chemically synthesized locus-specific RNAs and in vitro generated DICER RNA products promote DDR focus formation at the DNA damage site in RNase A-treated cells.

FIG. 6A A pool of chemically synthesized oligonucleotides was tested to restore DDR focus formation in RNase A-treated NIH2/4 cells. Mixed with a constant amount of RNA from parental cells (800 ng), a wide range of concentrations (1 ng/μl-1 fg/μl, ten-fold dilution steps) of locus-specific or control (GFP) RNAs was used. Locus-specific synthetic RNAs (down to a concentration of 100 fg/μl), but not control ones, allow site-specific DDR activation. FIG. 6B Short RNAs generated by recombinant DICER processing of RNA generated in vitro by transcription of a DNA fragment carrying the central portion of the integrated locus, or a control one of similar length, were tested to restore DDR focus formation at the DNA damage site in RNase A-treated NIH2/4 cells. RNAs were tested at the concentration of 1 ng/μl mixed with 800 ng of RNA from parental cells. Locus-specific DICER RNA products, but not control ones, allow site-specific DDR activation. FIG. 6C The fraction of 22-23 nt vs total short RNAs at the locus decreases in DICER and DROSHA knockdown samples both in uncut and cut conditions. In DICER knockdown samples the decrease is statistically significant (in the uncut samples p=4.8e-7, in the cut samples p=0.029). The fraction of 22-23 nt vs total short RNAs at the locus increases in the wildtype upon cutting (p=0.02). The statistical significance was calculated by fitting a negative binomial model to the short RNA count data and performing a likelihood ratio test, keeping the fraction of 22-23 nt vs total RNAs at the locus fixed across conditions under the null hypothesis and allowing it to vary between conditions under the alternative hypothesis. FIG. 6D The distribution of nucleotides at the 5' and the 3' end of RNA sequences from the damaged locus is depicted in the sequence logo, showing that 82.9% of sequences start with adenine or uracil and that 48.6% of sequences end with guanine.

FIG. 7A DICER, DROSHA knockdown by siRNA pools in OIS cells were evaluated by QRT-PCR. ATM knockdown by siRNA pool was evaluated by immunofluorescence. FIG. 7B DICER or DROSHA knockdown in OIS cells by siRNA increases BrdU incorporation rates. Histograms show the percentage of BrdU-positive cells. siGFP was used as control. Error bars indicate s.e.m. (n≥3). Differences are statistically significant (p-value<0.001). FIG. 7C DICER-, DROSHA- and DDR-inactivated OIS cells by transfection with siRNA pools, re-express MCM2, a marker of chromosomal DNA replication. Error bars indicate s.e.m. (n≥3). Differences are statistically significant (p-value<0.001). FIG. 7F DICER-, DROSHA- and DDR-inactivated OIS cells by transfection with siRNA pools, re-express pH3, a marker of entry into mitosis. Error bars indicate s.e.m. (n≥3). Differences are statistically significant (p-value<0.001). FIG. 7D DICER and DROSHA knockdown was evaluated by QRT-PCR and FIG. 7G DICER and DROSHA knockdown was evaluated by QRT-PCR FIG. 7E 53BP1 knockdown is evaluated by immunofluorescence.

FIG. 8A 200 nM and 20 nM concentration of siRNA pools against DICER or DROSHA in OIS cells allow escape from senescence. Error bars indicate s.e.m. (n≥3). Differences are statistically significant (p-value<0.05). Knockdown was evaluated by QRT-PCR. FIG. 8B 200 nM and 20 nM concentration of siRNA pools against DICER or DROSHA in OIS cells allow escape from senescence. Error bars indicate s.e.m. (n≥3). Differences are statistically significant (p-value<0.05). Knockdown was evaluated by QRT-PCR. FIG. 8C 200 nM and 20 nM concentrations of siRNA pools against DICER or DROSHA in OIS cells allow escape from senescence. Error bars indicate s.e.m. (n≥3). Differences are statistically significant (p-value<0.05). Knockdown was evaluated by QRT-PCR. FIG. 8D siRNA pools against DICER or DROSHA used in OIS cells were deconvolved and siRNAs were tested individually and they reproducibly allow escape from senescence. Error bars indicate s.e.m. (n≥3). Differences are statistically significant (p-value<0.05). Knockdown was evaluated by QRT-PCR. FIG. 8E siRNA pools against DICER or DROSHA used in OIS cells were deconvolved and siRNAs were tested individually and they reproducibly allow escape from senescence. Error bars indicate s.e.m. (n≥3). Differences are statistically significant (p-value<0.05). Knockdown was evaluated by QRT-PCR.

FIGS. 9A-9F|DICER or DROSHA inactivation in OIS cells does not alter SAHF maintenance and does not decrease DDR protein levels but impairs their activation over a range of siRNA concentrations. FIG. 9A DICER or DROSHA were inactivated by transfection with siRNA pool in OIS cells. Cells were stained for H3K9me3 SAHF marker and for 53BP1. siGFP transfected cells are used as control. DICER or DROSHA inactivation affects 53BP1 foci without altering SAHF stability. FIG. 9B Immunoblot analysis of H3K9me3 in DICER or DROSHA inactivated OIS cells. Total H3 is used as loading control. FIG. 9C Immunoblot analysis of 53BP1, ATM and H2AX in DICER or DROSHA inactivated OIS cells. siGFP transfected cells are used as control. Vinculin is used as loading control. FIG. 9D Different concentrations (10 fold difference) of siRNA pools against DICER or DROSHA in OIS cells impair DDR foci detection. Error bars indicate s.e.m. (n≥3). Differences are statistically significant (p-value<0.05). Knockdown was evaluated by QRT-PCR. FIG. 9E Different concentrations (10 fold difference) of siRNA pools against DICER or DROSHA in OIS cells impair DDR foci detection. Error bars indicate s.e.m. (n≥3). Differences are statistically significant (p-value<0.05). Knockdown was evaluated by QRT-PCR. FIG. 9F Different concentrations (10 fold difference) of siRNA pools against DICER or DROSHA in OIS cells impair DDR foci detection. Error bars indicate s.e.m. (n≥3). Differences are statistically significant (p-value<0.05). Knockdown was evaluated by QRT-PCR.

FIG. 10A DICER, DROSHA or GW182/TNRC6A were inactivated by siRNA pool in OIS cells. DICER-, DROSHA- or GW182/TNRC6A-inactivated cells were stained for 53BP1, pATM and pS/TQ markers of activated DDR. GW182/TNRC6A inactivation has no detectable effect on DDR. Differences for DICER and DROSHA, but not GW182, are statistically significant (p-value<0.005). Error bars indicate s.e.m. (n≥3). FIG. 10B Knockdown was evaluated by QRT-PCR.

FIG. 11A OIS cells inactivated by individual siRNA for DROSHA or TNRC6A, B and C simultaneously (with two different sets of siRNAs: pool #1 and #2) were stained for 53BP1, pATM and pS/TQ markers of activated DDR. TNRC6A, B and C simultaneous inactivation with either siRNA pools #1 or #2 has no detectable effect on DDR. Differences for DROSHA, but not TNRC6A B and C, are statistically significant (p-value<0.05). Error bars indicate s.e.m. (n≥3). FIG. 11B Knockdown was evaluated by QRT-PCR.

FIGS. 12A, 12B Efficiency of DICER or DROSHA knockdown in WI38 human fibroblasts was evaluated by immunostaining FIG. 12A and QRT-PCR FIG. 12B, respectively. FIG. 12C Immunoblot analysis of ATM, 53BP1 and H2AX proteins expression levels in DICER- or DROSHA-inactivated WI38. siGFP transfected cells are used as control. Vinculin is used as loading control. FIGS. 12D, 12E, 12F, and 12G siRNA pools against DICER or DROSHA were deconvolved and siRNAs were used individually. They all reduce DDR foci formation. 53BP1, but not γH2AX is reduced FIG. 12D and pATM and pS/TQ are reduced, FIG. 12E. Differences are statistically significant (p-value<0.005). Error bars indicate s.e.m. (n≥3). FIG. 12F Knockdown was evaluated by QRT-PCR. FIG. 12G Knockdown was evaluated by QRT-PCR.

FIG. 13A 53BP1-foci formation is impaired 10 minutes post IR (10Gy) in WI38 cells knocked-down for DICER or DROSHA by siRNA pools. Histograms show the percentage of WI38 cells positive for 53BP1 foci. Differences (*) are statistically significant (p-value<0.05). FIG. 13B Expression of siRNA-resistant wt DICER, but not a mutant allele lacking endonuclease activity, rescues DDR foci formation defect in DICER knocked-down cells. FIG. 13C 53BP1 foci formation was studied 10' after IR (10Gy), pATM and MDC1 1 hour afterward. Differences (*) are statistically significant (p-value<0.001). Error bars indicate s.e.m. (n=3). FIG. 13D Knockdown of endogenous DICER by 3'UTR siRNA was evaluated by QRT-PCR.

FIGS. 14A-14C|DICER or DROSHA, but not GW182, inactivation in HNF impairs DDR foci formation. FIG. 14A DICER, DROSHA or GW182/TNRC6A was inactivated in Wi38 cells by siRNA pools, cells were irradiated (2Gy) and stained for 53BP1 10' later, for γH2AX. FIG. 14B DICER, DROSHA or GW182/TNRC6A was inactivated in Wi38 cells by siRNA pools, cells were irradiated (2Gy) and stained for pATM and pS/TQ markers of activated DDR, 1 hour post IR. GW182/TNRC6A inactivation has no detectable effect on DDR. Differences for DICER and DROSHA, but not GW182, are statistically significant (p-value<0.001). Error bars indicate s.e.m. (n≥3). FIG. 14C Knockdown was evaluated by QRT-PCR.

FIGS. 15A-15D|DICER inactivation and TNRC6 A, B and C, simultaneous inactivation in HeLa cells is associated with similar levels of the co-transfected RFP-miR126 sensor mRNA but DDR foci are impaired only in DICER-inactivated cells FIG. 15A HeLa cells were cotransfected with RFP-miR126 sensor mRNA and siRNA against DICER or TNRC6A, B and C in a pool. Cells were irradiated (2Gy) and stained for 53BP1 10' later. FIG. 15B Both DICER and GW182-like proteins inactivation results in the upregulation of the miR126 sensitive RFP reporter but only DICER inactivation has detectable effect on DDR. Differences for DICER but not TNRC6 A, B and C, are statistically significant (p-value<0.05). Error bars indicate s.e.m. (n≥3). FIG. 15C Knockdown was evaluated by QRT-PCR. FIG. 15D The relative miRNA quantity of DICER and TNRC6A, B, and C in HeLa cells transfected with siRNA against DICER or TNRC6A, B and C is depicted.

FIG. 16A Immunoblot analysis of ATM, MDC1, 53BP1 and H2AX in wild-type (WT) and DICER$^{exon5}$-hypomorphic RKO cells. Vinculin and tubulin are used as loading control. FIG. 16B Irradiated DICER$^{exon5}$-hypomorphic RKO cells have delayed 53BP1-foci formation. Images show 53BP1-foci at 10, 30 and 90 minutes post IR (2Gy) in wild-type (WT) and DICER$^{exon5}$-hypomorphic RKO cells. FIG. 16C Histograms show the percentage of RKO cells positive for 53BP1 foci. Error bars indicate s.e.m. (n=3). Differences (*) are statistically significant (p-value<0.05).

FIG. 17A Expression of wt DICER but not a mutant allele lacking endonuclease activity, restores DDR foci formation defect in DICER$^{exon5}$-hypomorphic RKO cells. 53BP1 foci formation was studied 10' after IR (2Gy), pATM and pS/TQ 1 hour afterward. FIG. 17B Histograms show the percentage of cells positive for the indicated DDR foci. Differences (*) are statistically significant (p-value<0.001). Error bars indicate s.e.m. (n≥3).

FIG. 18A ATM activation following IR (10Gy) is impaired in DICER and DROSHA knocked-down WI38 human fibroblasts as detected by immunoblot analysis for pATM. siGFP transfected cells are used as a positive control for ATM activation. Total ATM is unaffected as shown by vinculin. DICER knockdown was evaluated by immunoblot analysis. FIG. 18B DROSHA knockdown in WI38 cells was evaluated by QRT-PCR. FIG. 18C ATM activation is impaired in irradiated (2Gy) DICER$^{exon5}$-hypomorphic RKO cells. Total ATM and vinculin are used as loading control.

FIG. 19D siRNA pools against DICER or DROSHA used in WI38 cells were deconvolved and siRNAs were used individually and they reproducibly impair G1/S checkpoint activation. Histogram shows the percentage of BrdU positive cells before (black bar) and after IR (gray bar) upon normalization on the percentage of BrdU-positive cells before IR for each cell line. Error bars indicate s.e.m. (n=3). FIG. 19E Knockdown was evaluated by QRT-PCR. FIG. 19F DICER-inactivated MRC-5 cells have impaired G1/S checkpoint post IR (10Gy). siGFP is used as control. FIG. 19G DICER and 53BP1 knockdowns efficiency in MRC-5 was monitored by immunofluorescence. Error bars indicate s.e.m. (n=3). Differences (*) are statistically significant (p-value<0.05).

FIG. 20A DICER-flag cDNA transfection into HCT116 DICER$^{exon5}$-hypomorphic cells restores a proficient G1/S checkpoint post IR (2Gy). Histograms show the percentage of BrdU-positive cells. Error bars indicate s.e.m. (n=3). Differences (*) are statistically significant (p-value<0.01). FIG. 20B Immunoblot analysis against flag-epitope shows the expression of DICER mutants (DICER-flag, DICER110ab-flag and DICER44ab-flag) in RKO cells. FIG. 20C DICER knockdown by shRNA in HEK293 cells was monitored by QRT-PCR. FIG. 20D DICER-inactivated HEK293 cells have impaired G2/M checkpoint as detected by pH3 immunostaining of mitotic cells in not irradiated cells and 24 h post IR (5Gy). Histograms show the percentage of pH3 positive cells in control and DICER-inactivated cells. Error bars indicate s.d. (n=3). Differences are statistically significant by student's t-test (p-value<0.05). FIG. 20E DICER knocked-down cells have an impaired G2/M checkpoint that can be restored upon transfection of siRNA-resistant DICER. The table shows the percentage of cells in G1, S and G2 phase of the cell cycle at different time points post IR. FIG. 20F FACS profiles of HEK293 cells transfected with the indicated combinations of siRNA and vectors (EV stands for empty vector), 36 hours post IR (5Gy). FIG. 20G Endogenous DICER (En DICER) knockdown and exogenous DICER (Exo DICER) overexpression were evaluated by QRT-PCR.

FIGS. 21A-21D|Dicer1 morpholino-injected zebrafish embryos downregulate the expression of miRNAs. FIG. 21A 72 hours post fertilization (hpf) larvae injected with Red Fluorescent Protein (RFP) miR126 sensor mRNA (1 larva on the left) or RFP miR126 sensor mRNA together with Dicer1 morpholino (3 larvae on the right). Note the jaw defects, small eye and delayed yolk re-absorption indicative of developmental delays in the Dicer1 morpholino-injected embryos. The same embryos visualized by epifluorescence show an increase in RFP expression in Dicer1 morpholino injected embryos. FIG. 21B Specificity of miR126 sensor. Upper panels show the expression levels of RFP miR126 sensor mRNA and GFP mRNA in the control, uninjected embryos. Lower panel shows the effects of Dicer1 morpholino injection on the expression of RFP miR126 sensor (increased in the absence of mature miR 126) and GFP (unchanged). FIG. 21C miRNA expression of 48 and 72 hours post fertilization embryos injected or not with Dicer1 morpholino were analyzed by real-time PCR. Data are expressed as relative expression level of Dicer1 morpholino-injected embryos compared to the control embryos not injected and are the mean of two independent pools of embryo performed in duplicate. FIG. 21D Table of raw $C_T$ values.

FIGS. 22A-22D|RNase A treatment degrades both mRNAs and microRNAs, leaves DDR protein levels unaltered but compromises their activation. FIG. 22A QRT PCR analysis of β-actin mRNA and miR-21 in mock and RNase A-treated cells. Error bars indicate s.d. (n=3). Differences are statistically significant by Student's t-test (p-value<0.05). FIG. 22B QRT PCR analysis of 53BP1 and ATM mRNA in RNase A-treated cells. Error bars indicate s.d. (n=3). Differences are statistically significant by Student's t-test (p-value<0.05). FIG. 22C RNase A treatment does not affect DDR (ATM, 53BP1, MDC1) protein stability. Lamin A/C is used as loading control. FIG. 22D RNase A affects 53BP1 and MDC1 but not □H2AX in the same focus. Irradiated HeLa cells were treated with PBS or RNase FIG. 22A 53BP1 foci (green) and MDC1 foci (red) are affected by RNase A treatment while γH2AX (magenta) foci in the same cell are not.

FIG. 23A Irradiation-induced (2Gy) 53BP1 foci are α-amanitin sensitive. HeLa cells were irradiated and incubated with PBS (−) or RNase A (+). Afterwards cells were incubated with the RNase A inhibitor RNaseOUT, with or without α-amanitin for 10 or 45 minutes. Incubation with α-amanitin prevents 53BP1-foci reformation. FIG. 23B Histogram shows the percentage of cells positive for 53BP1 foci. Error bars indicate s.e.m. (n=3). Differences (*) are statistically significant (p-value<0.01).

FIG. 24A shows the percentage of cells positive for 53BP1. FIG. 24B shows the percentage of cells positive for pATM. FIG. 24C shows the percentage of cells positive for pS/TQ.

FIGS. 25A-25C|Short RNAs promote DDR foci reformation at the DNA damage site FIG. 25A Relative enrichment of miR-21 RNA compared to β-actin mRNA quantity evaluated by QRT-PCR in total RNA and short RNA-enriched fractions. FIG. 25B Histograms show the percentage of cells positive for 53BP1, pATM and pS/TQ foci in irradiated HeLa cells, RNase A-treated, and cells incubated with 200 ng of total RNA or a proportional volume of short RNA-enriched (<200 nt) fraction. tRNA (200 ng) was used as control. FIG. 25C Irradiation-induced 53BP1 (green) and pATM (red) foci are restored in RNase A-treated cells by incubation with total and short RNAs-enriched fraction. tRNA was used as control.

FIGS. 26A and 26B|Irradiation-induced DDR foci are restored in RNase A-treated cells by incubation with RNAs extracted from gel in the 20-35 nt range. FIG. 26A Irradiated cells were RNase A treated and incubated with equal amounts (50 ng) of RNA extracted from polyacrilamide gel as shown in FIG. 4C Images show 53BP1 staining in cells incubated with the indicated RNAs. FIG. 26B QRT PCR analysis of RNU19 (200 nt), RNU44 (61 nt) and mir-21 (22 nt) in the indicated RNA fractions extracted from gel. Error bars indicate s.d. (n=3). Differences are statistically significant by student's t-test (p-value<0.005).

FIG. 27A Irradiated cells were RNase A-treated and incubated with RNA extracted from the indicated cells. RNA from wild type cells or DICER$^{exon5}$-hypomorphic cells transfected with wild type DICER allows 53BP1 foci reformation, while RNA from untransfected DICER$^{exon5}$-hypomorphic cells or the same cells transfected with mutant DICER do not. FIG. 27B Histograms show the percentage of cells positive for the indicated DDR markers. Error bars indicate s.e.m. (n=3). Differences (*) are statistically significant (p-value<0.005).

FIGS. 28A-28E|DICER and DROSHA RNA products are required for DDR foci reformation FIG. 28A RNA extracted from wild-type HCT116 and DLD-1 cell lines, but not that extracted from DICER$^{exon5}$-hypomorphic HCT116 and DLD-1 cell lines, rescues 53BP1 foci. Histograms show the percentage of cells positive for 53BP1 foci. Error bars indicate s.e.m. (n=3). Differences are statistically significant (p-value<0.01). FIG. 28B RNA extracted from shDICER-transfected (or GFP as control) HEK293 cells does not restore irradiation-induced 53BP1 foci in RNase A-treated HeLa cells. tRNA is used as negative control. FIG. 28C Histograms report the percentage of cells positive for 53BP1 foci. FIG. 28D Immunoblotting shows DICER knockdown efficiency. FIG. 28E Histograms show the percentage of cells positive for 53BP1, pATM and pS/TQ foci in irradiated HeLa cells after RNase A treatment and incubation with RNA purified from siGFP and siDROSHA transfected cells. tRNA was used as control.

FIGS. 29A and 29B|MRN complex involvement in DDR foci reformation after RNase treatment. FIG. 29A MRN complex recruitment to the I-Sce I-induced DSB is sensitive to RNase A treatment. 53BP1, pATM and MRE11 foci, but not γH2AX, are lost in RNase A treated NIH2/4 cells. Histograms show the percentage of cells in which 53BP1, pATM, MRE11 or γH2AX foci colocalizing with the Cherry-Lac focus. FIG. 29B Mirin impairs pATM activation on the I-Sce I-induced DSB. Histogram shows the percentage of cells in which pATM focus colocalize with the Cherry-Lac focus. Error bars indicate s.e.m. (n≥3). Differences are statistically significant (*p-value<0.05).

FIG. 30A Nuclear RNA shorter than 200 nt was purified and analyzed on the small RNA Bioanalyser kit (Agilent). FIG. 30B Short RNA library was prepared and extracted from 6% polyacrylamide gel (indicated by an arrow at 100 bp). FIG. 30C The integrity of the prepared library was checked using the Agilent DNA high sensitivity kit. FIG. 30D Length distribution of tags in the library. FIG. 30E Length distribution of tags in the library mapping to the exogenous integrated locus combining tags from cut and uncut samples. FIG. 30F A pool of chemically synthesized oligonucleotides mapping to the exogenous locus was tested to restore DDR focus formation in RNase A-treated NIH2/4 cells. Mixed with a constant amount of tRNA, a wide range of concentrations (0.1 ng/µl, 0.1 pg/µl and 1 fg/µl) of locus-specific or control (GFP) RNAs, was used. FIG. 30G DICER processing was evaluated by running DICER RNA-products on a 3% agarose gel. FIG. 30H Short RNAs cleaved by recombinant DICER processing of RNA generated in vitro upon transcription of a DNA fragment carrying the central portion of the integrated locus, or a control one of similar length, were tested to restore DDR focus formation in RNase A-treated NIH2/4 cells. RNAs were tested at the concentration of 1 ng/µl mixed with 800 ng of tRNA. Locus-specific DICER RNA products, but not control ones, allow site-specific DDR activation at the DNA damage site. Histograms report the percentage of cells positive for DDR foci.

FIG. 31A Bioanalyser profile of <200 nt RNA from wildtype cut sample. FIG. 31B Short RNA libraries were prepared from 40 ng RNA from each sample and run on a 6% PAGE gel. Arrow shows the 100 bp library band of interest. FIG. 31C Wildtype cut library profile. Gel extracted libraries were run on Bioanalyser high sensitivity kit. Sequencing was performed on Hi seq Version 3. FIG. 31D Tag length distribution of wildtype uncut. FIG. 31E Tag length distribution of Dicer KD uncut. FIG. 31F Tag length distribution of Drosha KD uncut. FIG. 31G Tag length distribution of wildtype uncut. FIG. 31H Tag length distribution of Dicer KD cut. FIG. 31I Tag length distribution of Drosha KD uncut.

FIG. 32A Dicer and Drosha knockdown by shRNA in uncut and cut samples was evaluated by QRT-PCR. FIG. 32B Reads mapping to the miRNA database miRBase release 18 were normalized with the number of reads of spike in each library. Normalized miRNAs in Dicer and Drosha knockdown samples were compared with wildtype samples before and after cut (as labeled). Statistical significance was calculated using the Wilcoxon signed-rank test. The authors find that miRNAs are significantly lower expressed in the Dicer and Drosha knockdown sample compared to the wildtype sample in both cut and uncut conditions (Dicer knockdown uncut vs wildtype uncut p=1.544e-263; Drosha knockdown uncut vs wildtype uncut p=3.843e-279; Dicer knockdown cut vs wildtype cut p=8.911e-84; Drosha knockdown cut vs wildtype cut p=1.172e-275).

FIG. 33A depicts the length of tags arising from the locus before and after cutting. FIG. 33B depicts the length of tags arising from the locus before and after cutting with shDICER. FIG. 33C depicts the length of tags arising from the locus before and after cutting with shDROSHA. FIG. 33D 22-23 nt percentage of the locus is significantly different from the same ratio of non miRNA genomic loci. Fractions of 22-23 nt vs total short RNAs at non miRNA genomic loci with at least 50 reads are shown in histograms with the vertical axis depicting their frequency. In each sample, the vertical line depicts the ratio of 22-23 nt RNAs to the total at the locus. The p-value was calculated by summing the area (indicated in red) to the right of this line. The authors find that the fraction of 22-23 nt vs total short RNAs at the locus studied is significantly higher than the fraction of 22-23 nt tags at non miRNA genomic loci in both uncut (p=0.049) and cut (p=0.022) conditions.

FIG. 34A shows the TET-I-SceI-LAC locus, the DDRNAs generated upon cut (grey line), and the LNAs used (black dotted line). Cells were co-transfected with Cherry-Lac and I-Sce I-restriction endonuclease expressing vectors together with different sets (as in the legend in the figure) of LNA (200 pM) with the potential to anneal to DDRNAs arising from the locus upon I-SceI-induced cleavage or a control LNA matching telomere sequence. 24 h post transfection cells were scored for DDR markers at the Lac array. Histograms show the percentage of cells positive for the DDR markers analysed: γH2AX FIG. 34B is not affected, whereas 53BP1 FIG. 34C accumulation at the locus is significantly reduced upon all sets of transfected LNAs. Around 100 cells from three independent experiments were scored. Error bars indicate s.e.m. Statistical significance was calculated by Chi-squared test compared to control LNA (sample 2). *p-value<0.05, p-value<0.01, *p-value<0.005.

FIGS. 35A and 35B|DDR activation (53BP1 focus maintenance) at uncapped telomeres is RNA-dependent. TRF2$^{flox/flox}$ MEFs (Lazzerini Denchi and de Lange, Nature 2007) were treated with 4-hydroxytamoxifen to induce cre-mediated TRF2 knockout and generate uncapped telomeres. 48 hours later, cells were permeabilized and treated with RNase A or BSA, as a control. FIG. 35A Representative images show that γH2AX foci are stable, while 53BP1 foci disassemble upon RNase A treatment. FIG. 35B Quantification of γH2AX and 53BP1 foci in RNase A and BSA treated cells. For the quantifications shown around 150 cells from two independent experiments were scored. Error bars indicate s.e.m. ***p-value<0.001.

FIG. 36A 53BP1 foci-positive cells were scored at the indicated time points post transfection. LNA 5 and 6 cause a decrease in DDR-positive cells, to different extent, compared to control LNA in induced cells, while no difference was observed in uninduced cells. For the quantifications shown, around 30-100 cells were scored for each time point FIGS. 36B, 36C Induced cells were incubated with BrdU for 16 hours and scored for BrdU incorporation 3 days following LNA transfection. LNA 5 and 6 transfected Flag+cells show a significant increase in the percentage of BrdU-positive cells, compared to the Cntrl LNA FIG. 36B, while no difference is observed in Flag−cells FIG. 36C. For the quantifications shown around 150 cells from three FIG. 36B or two FIG. 36C independent experiments were scored. Error bars indicate s.e.m. *p-value<0.05, ***p-value<0.001.

DETAILED DESCRIPTION OF THE INVENTION

Figure 1A:
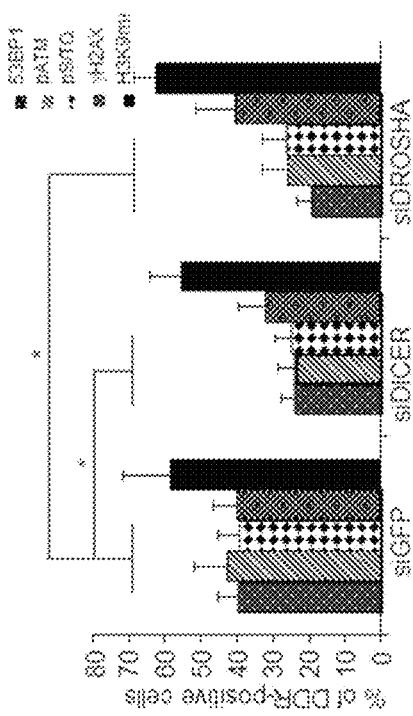
FIGS. 1A-1F|DICER or DROSHA inactivation impairs DDR foci stability and formation in OIS and in irradiated cells.

Methods
Cultured Cells.

Early passage BJ cells, WI38 and MRC-5 (The American Type Culture Collection, ATCC) were grown under standard tissue culture conditions (37° C., 5% $CO_2$) in MEM supplemented with 10% fetal bovine serum, 1% L-glutamine, 1% non-essential aminoacids, 1% Na Pyruvate. HeLa, Phoenix ecotrophic and HEK293T cell lines were grown under standard tissue culture conditions (37° C., 5% $CO_2$) in DMEM, supplemented with 10% fetal bovine serum, 1% glutamine, 1% penicillin/streptomycin. RKO, HCT116 and DLD1 colon cancer cell lines[25] were cultured in Mc'Coy 5A medium+10% fetal calf serum, 1% penicillin/streptomycin. NIH2/4[35] where grown in DMEM, supplemented with 10% fetal bovine serum, 1% glutamine, gentamicine (40 μg/ml), and hygromycin (400 μg/ml).

H-RasV12 overexpressing senescent BJ cells were generated as in[20]. BrdU incorporation assays were carried at least a week after cultures had fully entered the senescent state, as determined by ceased proliferation, DDR activation, SAHF formation, and senescence-associated β-galactosidase expression. Ionizing radiation (IR) was induced by a high-voltage X-rays generator tube (Faxitron X-Ray Corporation). In general, cultured cells were exposed to 2 Grays for the foci formation assay. The authors used 5 Grays for the G2/M checkpoint assays and 10 Grays for the G1/S checkpoint assays.

Cherry-Lac and I-Sce I-restriction endonuclease expressing vector were transfected by lipofectamine 2000 (Invitrogen) in a ratio of 3:1. 16 h post transfection around 70% of the cells were scored positive for DDR markers at the Lac array. For generation of Dicer and Drosha knocked-down NIH2/4 cells were infected with Lentiviral particles carrying pLKO.1, shDicer or shDrosha vectors. After 48 hours cells were superinfected with Adeno Empty Vector or Adeno I-Sce I [Anglana et al. Nucl Ac Res 1999]. Nuclei were isolated the day after the adenoviral infection.

Transient expression of ER-I-PpoI endonucleases in HeLa cells was carried out by Lipofectamine 2000 transfection and 16 hours later tamoxifen (0.1 μM) was added to culture medium to induce the activation of the endonuclease. 4 hours later cells were fixed for immunostaining or used for RNA extraction. Cherry-Lac transfected (mock) cells were used as control in these experiments.

Cultured Cells and LNA Transfection (for the experiments in FIG. 34). NIH2/4 cells where grown in DMEM, supplemented with 10% fetal bovine serum, 1% glutamine, gentamicine (40 mg/ml), and hygromycin (400 mg/ml). Cherry-Lac and I-Sce I-restriction endonuclease expressing vectors were transfected with Lipofectamine 2000 (Invitrogen) with a 3:1 ratio. LNA were first boiled at 90° C. for 5 minutes and quickly chilled at 4° C. for 5 minutes and then added in different combinations to the Cherry-Lac and I-Sce I transfection mix, at the final concentration of 200 pM. 24 h post transfection cells were scored for DDR markers at the Lac array.

Cultured Cells (for the experiments in FIGS. 35-36). T19 fibrosarcoma cells (van Steensel, Cell 1998) were grown in DMEM supplemented with 10% fetal bovine serum, 1% glutamine and doxycycline (100 ng/ml). For induction, cells were grown without doxycycline for at least 7-8 days. CRE-ER TRF2$^{flox/flow}$ MEFs (Lazzerini Denchi and de Lange, Nature 2007) were grown in DMEM supplemented with 10% fetal bovine serum and 1% glutamine. For induction, cells were grown in presence of 4-hydroxytamoxifen (600 nM) for 48 hours. For BrdU incorporation, cells were labeled with 10 μg/ml bromodeoxyuridine (BrdU, Sigma) for 16 hours and incorporation was evaluated by immunofluorescence after DNA denaturation.

Antibodies.

Mouse anti-γH2AX, anti-H3K9me3, rabbit polyclonal anti-PH3 (Upstate Biotechnology); anti-pS/TQ (Cell Signaling Technology); anti-H2AX, anti-H3 and anti DICER (13D6) (Abcam); rabbit polyclonal anti-53BP1 (Novus Biological) and mouse monoclonal anti-53BP1 (a gift from Thanos Halazonetis); anti-MRE11 (a gift from S. Jackson); anti pH3, anti-BrdU (Becton Dickinson); rabbit polyclonal anti-MCM2 (a gift of Marine Melixetian); anti MRE11 rabbit polyclonal raised against recombinant MRE11; anti-pATM (Rockland); mouse monoclonal anti-ATM and anti-MDC1 (SIGMA); anti-vinculin (clone hVIN-1), anti-β-tubulin (clone AA2) and anti-Flag M2 monoclonal antibodies (SIGMA).

Indirect Immunofluorescence.

Cells were grown on poly-D-lysinated coverslips (poly-D-lysine was used at 50 μg/ml final concentration) and plated (15-20×10$^3$ cells/cover) one day before staining. DDR and BrdU staining was performed as in[20]. Cells were fixed in 4% paraformaldehyde or methanol:acetone 1:1. NIH2/4 mouse cells were fixed by 4% paraformaldehyde as in[35]. Images were acquired using a wide field Olympus Biosystems Microscope BX71 and the analySIS or the MetaMorph software (Soft Imaging System GmbH). Comparative immunofluorescence analyses were performed in parallel with identical acquisition parameters; at least 100 cells were screened for each antigen. Cells with more than 2 DDR foci were scored positive. Foci intensity quantifications were performed using Cell Profiler software 2.0. Confocal sections were obtained with a Leica TCS SP2 AOBS confocal laser microscope by sequential scanning.

Immunofluorescence (for the experiments in FIGS. 35-36). Cells were fixed with 1:1 methanol/acetone solution for 2 minutes at room temperature, or 4% paraformaldehyde for 10 minutes at room temperature. After blocking, cells were stained with primary antibodies for 1 h at room temperature, washed and incubated with conjugated secondary antibodies for 40 minutes at RT. Nuclei were stained with DAPI (1 μg/ml).

Plasmids.

Flag-DICER, Flag-DICER44ab and Flag-DICER110ab were a kind gift of R. Shiekhattar. pLKO.1 shDICER expressing vector was a kind gift of WC. Hahn. Short hairpin sequence for DICER is: CCG GCC ACA CAT CTT CAA GAC TTA ACT CGA GTT AAG TCT TGA AGA TGT GTG GTT TTT G (SEQ ID NO:1). pRETROSUPER shp53 as in[20]. Short hairpin sequence for p53 was: AGT AGA TTA CCA CTG GAG TCT T (SEQ ID NO:2). Cherry-Lac-repressor and I-Sce I-restriction endonuclease expressing vectors were kind gifts of E. Soutoglou[35]. ER-I-Ppo I-restriction endonuclease expressing vector was a kind gift of Michael Kastan[33]. shRNA against mouse Dicer and Drosha expressing vectors were a kind gift of W. C. Hahn. shRNA for mouse Dicer: CCG GGC CTC ACT TGA CCT GAA GTA TCT CGA GAT ACT TCA GGTCAA GTG AGG CTT TTT (SEQ ID NO:3). shRNA for mouse Drosha: CCG GCC TGG AAT ATG TCC ACA CTT TCT CGA GAA AGT GTG GAC ATA TTC CAG GTT TTT G (SEQ ID NO:4).

siRNA.

The DHARMACON siGENOME SMARTpool siRNA oligonucleotide sequences for human 53BP1, ATM, DICER, DROSHA were:

53BP1:

GAG AGC AGA UGA UCC UUU A; (SEQ ID NO: 5)

GGA CAA GUC UCU CAG CUA U; (SEQ ID NO: 6)

GAU AUC AGC UUA GAC AAU U; (SEQ ID NO: 7)

GGA CAG AAC CCG CAG AUU U. (SEQ ID NO: 8)

ATM:

GAA UGU UGC UUU CUG AAU U; (SEQ ID NO: 9)

AGA CAG AAU UCC CAA AUA A; (SEQ ID NO: 10)

UAU AUC ACC UGU UUG UUA G; (SEQ ID NO: 11)

AGG AGG AGC UUG GGC CUU U. (SEQ ID NO: 12)

DICER:

UAA AGU AGC UGG AAU GAU G; (SEQ ID NO: 13)

GGA AGA GGC UGA CUA UGA A; (SEQ ID NO: 14)

GAA UAU CGA UCC UAU GUU C; (SEQ ID NO: 15)

GAU CCU AUG UUC AAU CUA A. (SEQ ID NO: 16)

DROSHA:

CAA CAU AGA CUA CAC GAU U; (SEQ ID NO: 17)

CCA ACU CCC UCG AGG AUU A; (SEQ ID NO: 18)

GGC CAA CUG UUA UAG AAU A; (SEQ ID NO: 19)

GAG UAG GCU UCG UGA CUU A. (SEQ ID NO: 20)

The DHARMACON siGENOME si RNA sequences for Human TNRC6A, B and C were:

GW182/TNRC 6A:

GAA AUG CUC UGG UCC GCU A; (SEQ ID NO: 21)

GCC UAA AUA UUG GUG AUU A. (SEQ ID NO: 22)

TNRC6B:

GCA CUG CCC UGA UCC GAU A; (SEQ ID NO: 23)

(SEQ ID NO: 24)

```
                           -continued
GGA AUU AAG UCG UCG UCA U.

TNRC6C:
                                         (SEQ ID NO: 25)
CUA UUA ACC UCG CCA AUU A;

(SEQ ID NO: 26)
GGU AAG UCC UCC AUU GAU G.

siRNA against human DICER 3' UTR:
                                         (SEQ ID NO: 27)
CCG UGA AAG UUU AAC GUU U.

siRNA against GFP:
                                         (SEQ ID NO: 28)
AAC ACU UGU CAC UAC UUU CUC.

siRNA against Luciferase:
                                         (SEQ ID NO: 29)
CAU UCU AUC CUC UAG AGG AUG dTdT;

(SEQ ID NO: 30)
dTdT GUA AGA UAG GAG AUC UCC UAC.
``` siRNAs were transfected by Oligofectamine (Invitrogen) at a final concentration of 200 nM in OIS cells and 100 nM in HNF. In the siRNA titration experiment we transfected OIS cells in parallel with 20 nM and 200 nM siRNA oligos. For siRNA transfection with deconvolved siRNA oligos the authors used 50 nM for smart pools and 12.5 nM for deconvolved siRNAs.

Real-Time Quantitative PCR (RT-QPCR).

Total RNA was isolated from cells using TRIzol (Invitrogen) or RNAeasy kit (Qiagen) according to the manufacturer's instructions, and treated with DNAse before reverse transcription. For microRNA isolation the authors used mirVana™ miRNA Isolation Kit (Ambion). cDNA was generated using the Superscript II Reverse Transcriptase (Invitrogen). cDNA was used as template in TaqMan® Gene Expression Assays (Applied Biosystems) for the evaluation of DICER (Assay ID: Hs00998580_m1) and DROSHA (Assay ID: Hs01095030_m1) mRNA levels. TaqMan® MicroRNA Assays (Applied Biosystems) were used for the evaluation of mature miR-21 and rnu44 and rnu19 expression levels (Assay ID: 000397, 001094 and 001003). 18S or β-actin was used as a control gene for normalization. miR21 and rnu44 enrichment in the small RNA-enriched fraction was evaluated as the ratio between PCR cycles (ct) for miR-21 or rnu44 and for β-actin mRNA after normalization to the same ratio in total RNA fraction. Real-time quantitative PCR reactions were performed on an Applied Biosystems ABI Prism 7900HT Sequence Detection System or on a Roche LightCycler 480 Sequence Detection System. The reactions were prepared using SyBR Green reaction mix from Roche. Ribosomal protein P0 (RPP0) was used as a human and mouse control gene for normalization.

Primer sequences for real-time quantitative PCR were:

```
RPP0:
(Forward)
                                         (SEQ ID NO: 31)
TTCATTGTGGGAGCAGAC, (Reverse)
                                         (SEQ ID NO: 32)
CAGCAGTTTCTCCAGAGC;

human endogenous DICER:
(Forward)
                                         (SEQ ID NO: 33)
AGCAACACAGAGATCTCAAACATT, (Reverse)
                                         (SEQ ID NO: 34)
GCAAAGCAGGGCTTTTCAT;

human endogenous and overexpressed DICER:
(Forward)
                                         (SEQ ID NO: 35)
TGTTCCAGGAAGACCAGGTT, (Reverse)
                                         (SEQ ID NO: 36)
ACTATCCCTCAAACACTCTGGAA;

human DROSHA:
(Forward)
                                         (SEQ ID NO: 37)
GGCCCGAGAGCCTTTTATAG , (Reverse)
                                         (SEQ ID NO: 38)
TGCACACGTCTAACTCTTCCAC;

human GW182:
(Forward)
                                         (SEQ ID NO: 39)
CAGCCAGTCAGAAAGCAGTG, (Reverse)
                                         (SEQ ID NO: 40)
TGTGAGTCCAGGATCTGCTACTT;

mouse Dicer:
(Forward)
                                         (SEQ ID NO: 41)
GCAAGGAATGGACTCTGAGC, (Reverse)
                                         (SEQ ID NO: 42)
GGGGACTTCGATATCCTCTTC;

mouse Drosha:
(Forward)
                                         (SEQ ID NO: 43)
CGTCTCTAGAAAGGTCCTACAAGAA, (Reverse)
                                         (SEQ ID NO: 44)
GGCTCAGGAGCAACTGGTAA.
```

RNase a Treatment and RNA Complementation Experiments.

Cells were plated on poly-D-lysinated coverslips and irradiated with 2Gy of IR. 1 h after HeLa cells were permeabilized with 2% Tween 20 in PBS for 10 minutes at RT while I-Sce I-transfected NIH2/4 cells were permeabilized in 0.5% Tween 20 in PBS for 10 minutes at RT. RNase A treatment was carried out in 1 ml of 1 mg/ml Ribonuclease A from bovine pancreas (Sigma-Aldrich cat n: R5503) in PBS for 25 minutes at room temperature. After RNase A digestion, the samples were washed with PBS, treated with 80 units of RNase inhibitor (RNaseOUT Invitrogen 40 units/μl) and 2 μg/ml of α-amanitin (SIGMA) for 15 minutes in a total volume of 70 μl. For experiments with mirin, NIH2/4 cells were incubated at this point also with 100 μM mirin (SIGMA) or DMSO for 15 minutes. Then, RNase A-treated cells were incubated with total, small or gel extracted RNA, or the same amount of tRNA, for additional 15 minutes at room temperature. If using mirin, NIH2/4 cells were incubated with total RNA in the presence of 100 μM mirin or DMSO for 25 minutes at room temperature. Cell were then fixed with 4% paraformaldehyde or methanol: acetone 1:1.

In complementation experiments with synthetic RNA oligonucleotides, eight RNA oligonucleotides with the potential to form four pairs were chosen among the sequences obtained by deep sequencing that map at the integrated locus in NIH2/4 cells. Synthetic RNA oligonucleotides were generated by SIGMA with a monophosphate modification at the 5' end. Sequences map to different regions of the integrated locus: two pairs map to a unique sequence flanking the I-Sce I restriction site (Oligo 1+Oligo 2 and Oligos 3+Oligo 4), one to the Lac-operator (Oligo 5+Oligo 6) and one to the Tet-repressor repetitive sequences (Oligo 7+Oligo 8). Two paired RNA oligonucleotides with the sequences of GFP were used as negative control (Oligo GFP 1+Oligo GFP 2). Sequences are reported below.

DDRNA Sequences

```
Oligo 1:
                                    (SEQ ID NO: 45)
5'-AUA ACA AUU UGU GGA AUU CGG CGC-3', oligo 2:
                                    (SEQ ID NO: 46)
5'-CGA AUU CCA CAA AUU GUU AUC C-3', oligo 3:
                                    (SEQ ID NO: 47)
5'-AUU UGU GGA AUU CGG CGC CUC UAG AGU CGA GG-3', oligo 4:
                                    (SEQ ID NO: 48)
5'-CCU CGA CUC UAG AGG CG-3', oligo 5:
                                    (SEQ ID NO: 49)
5'-AGC GGA UAA CAA UUU GUG GCC ACA UGU GGA-3', oligo 6:
                                    (SEQ ID NO: 50)
5'-UGU GGC CAC AAA UUG UU-3', oligo 7:
                                    (SEQ ID NO: 51)
5'-ACU CCC UAU CAG UGA UAG AGA AAA GUG AAA GU-3', oligo 8:
                                    (SEQ ID NO: 52)
5'-CUU UCA CUU UUC UCU AUC ACU GAU AGG GAG UG-3'

GFP 1:
                                    (SEQ ID NO: 53)
5'-GUU CAG CGU GUC CGG CGA GUU-3',

GFP 2:
                                    (SEQ ID NO: 54)
5'-CUC GCC GGA CAC GCU GAA CUU-3'
```

RNAs were resuspended in 60 mM KCl, 6 mM HEPES-pH 7.5. 0.2 mM MgCl2, at the stock concentration of 12.5 µM, denatured at 95° C. for 5 minutes and annealed for 10 minutes at room temperature.

DICER RNA products were generated as follows. A 550 bp DNA fragment carrying the central portion of the genomic locus studied (three Lac repeats, the I-Sce I site and two Tet repeats) was flanked by T7 promoters at both ends and was used as a template for in vitro transcription with the TurboScript T7 transcription kit (AMSBIO). The 500 nt long RNA obtained was purified and incubated with human recombinant DICER enzyme (AMSBIO) to generate 22-23 nt RNAs. RNA products were purified, quantified and checked on a polyacrylamide or an agarose gel. As a control, the same procedure was followed with a 700 bp construct containing the RFP DNA sequence. Equal amounts of DICER products generated in this way were used in complementation experiment in NIH2/4 cells following RNase treatment.

RNaseA Treatment (for the experiments in FIG. 35). CRE-ER TRF2$^{flox/flox}$ MEFs (Lazzerini Denchi and de Lange, Nature 2007) were induced to generate TRF2 knockout and telomere uncapping. 48 hours later cells were permeabilized with 0.6% Tween 20 in PBS for 15 min at room temperature. RNase A treatment was carried out in 1 ml of 1 mg/ml ribonuclease A from bovine pancreas (Sigma-Aldrich catalogue no. R5503) in PBS for 30 minutes at room temperature.

LNA Transfection (for the experiments in FIG. 36). LNA were first boiled at 90° C. for 5 minutes, chilled at 4° C. for 5 minutes and transfected with Lipofectamine RNAiMAX (Invitrogen) at the final concentration of 200 nM.

Small RNA Preparation.

Total RNA was isolated from cells using TRIzol (Invitrogen) according to the manufacturer's instructions. To generate small RNA-enriched fraction and small RNA-devoid fraction the authors used mirVana™ microRNA Isolation Kit (Ambion) according to the manufacturer's instructions. The mirVana microRNA isolation kit employs an organic extraction followed by immobilization of RNA on glass-fiber (silica-fibers) filters to purify either total RNA, or RNA enriched for small species. For total RNA extraction ethanol is added to samples, and they are passed through a Filter Cartridge containing a glass-fiber filter, which immobilizes the RNA. The filter is then washed a few times, and finally the RNA is eluted with a low ionic-strength solution. To isolate RNA that is highly enriched for small RNA species, ethanol is added to bring the samples to 25% ethanol. When this lysate/ethanol mixture is passed through a glass-fiber filter, large RNAs are immobilized, and the small RNA species are collected in the filtrate. The ethanol concentration of the filtrate is then increased to 55%, and it is passed through a second glass-fiber filter where the small RNAs become immobilized. This RNA is washed a few times, and eluted in a low ionic strength solution. Using this approach consisting of two sequential filtrations with different ethanol concentrations, an RNA fraction highly enriched in RNA species ≤200 nt can be obtained[25,66].

RNA Extraction from Gel.

Total RNA samples were heat-denatured, loaded and resolved on a 15% denaturing acrylamide gel [1×TBE, 7 M urea, 15% acrylamide (29:1 acryl:bis-acryl)]. Gel was run for 1 hour at 180 V and stained in GelRed solution. Gel slices were excised according to the molecular weight marker, moved to a 2 ml clean tube, smashed and RNA was eluted in 2 ml of ammonium acetate 0.5 M, EDTA 0.1 M in RNase-free water, rocking overnight at 4° C. Tubes were then centrifuged 5 minutes at top speed, the acqueous phase was recovered and RNA was precipitated and resuspended in RNase free water.

G1/S Checkpoint Assay.

WI38, BJ and MRC-5 cells were irradiated with 10Gy and 1 hour afterwards incubated with BrdU for 7 h; HCT116 and RKO cells were irradiated 2Gy and incubated with BrdU for 2 h. Cells were fixed with 4% paraformaldehyde and probed for BrdU immunostaining. At least 100 cells per condition were analyzed.

G2/M Checkpoint Assay.

HEK 293 calcium phosphate transfected cells were irradiated with 5Gy and allowed to respond to IR-induced DNA damage in a cell culture incubator for 12, 24 or 36 hours. Then, at these three time points post irradiation, together with not irradiated cells, 1×10$^6$ cells were collected for Fluorescence Activated Cell Sorting (FACS) analysis, fixed in 75% ethanol in PBS, 30 minutes on ice. Afterwards, cells were treated 12 hours with 40 µg/ml of RNase A and incubated at least 1 h with propidium iodide (PI). FACS profiles were obtained by the analysis of at least 5×10$^5$ cells. In the complementation experiments HEK 293 were transfected using Lipofectamine RNAi Max (Invitrogen) and 48 hours later irradiated with 5Gy. Cells were then treated as explained above.

Immunoblotting.

Cells were lysed in sample buffer and 50-100 µg of whole cell lysate were resolved by SDS-PAGE, transferred to nitrocellulose and probed as in[20].

For zebrafish immunoblotting protein analysis, 72 hours post fertilization (hpf) larvae were deyolked in Krebs Ringer's solution containing 1 mM EDTA, 3 mM PMSF and proteases inhibitor (Roche complete protease inhibitor cocktail). Embryos were then homogenized in SDS sample buffer containing 1 mM EDTA with a pestle, boiled 5 min and centrifuged 13000 rpm for 1 min. Protein concentration was measured with the BCA method (Pierce) and proteins (50 µg-900 µg) were loaded in an SDS-12% (for γH2AX and H3) and SDS-6% polyacrylamide gel (for pATM and ATM), transferred to a nitrocellulose membrane, and incubated with anti-γH2AX (1:2000, a gift from J. Amatruda[67]), H3 (1:10000, Abcam), pATM (1:1000, Rockland), ATM (1:1000, Sigma). Immunoreactive bands were detected with horseradish peroxidase-conjugated anti-rabbit or anti-mouse IgG and an ECL detection kit (Pierce, Springfield, Ill., USA). Protein loading was normalized to equal amounts of total ATM and H3.

Zebrafish Embryo Injection, Cell Transplantation and Staining.

Zebrafish embryos at the stage of 1-2 cells were injected with a morpholino against Dicer1[29] diluted in Danieau buffer. The morpholino oligonucleotide was injected at a concentration of 5 ng/nl, and a volume of 2 nl/embryo. To assess the efficiency of the morpholino to block microRNA maturation, the authors co-injected the morpholino with in vitro synthesized mRNA, encoding for red fluorescent protein (RFP) and carrying 3 binding site for miR126 in the 3' UTR[28]. The oligonucleotides carrying the binding sites for miR126 used for construction of pCS2:RFPmiR126 sensor are:

(SEQ ID NO: 55)
5' GCATTATTACTCACGGTACGAATAAGGCATTATTACTCACGGTACGA
ATAAGGCATTATTACTCACGGTACGA 3'
and (SEQ ID NO: 56)
5' CGTAATAATGAGTGCCATGCTTATTCCGTAATAATGAGTGCCATGCT
TATTCCGTAATAATGAGTGCCATGCT 3'.

The construct was verified by sequencing and used to synthesize mRNA in vitro using the mMessage Kit (Ambion). Messenger RNA encoding for RFPmiR126 sensor was injected alone or in combination with Dicer1 morpholino at a concentration of 10 pg/nl. Dicer morpholino was injected at a concentration of 5 ng/nl, and a volume of 2 nl/embryo. For cell transplantation experiments, the authors injected donor embryos with a mixture of dicer1 morpholino and mRNA encoding for GFP (5 pg/nl). Approximately 20 cells were transplanted from donor embryos at dome (5 hpf) stage to uninjected host at the same stage. Succesfully transplanted larvae (displaying GFP+ cells) were irradiated as described below. Mature miRNA were reverse transcribed to produce 6 different cDNA for TaqMan® MicroRNA assay (30 ng of total mRNA for each reaction; Applied Biosystems). Real-time PCR reactions based on TaqMan reagent chemistry were performed in duplicate on ABI PRISM® 7900HT Fast Real-Time PCR System (Applied Biosystems). The level of miRNA expression was measured using $C_T$ (threshold cycle). Fold change was generated using the equation $2^{-CT}$.

For immunofluorescence in zebrafish larvae: 72 hpf larvae were irradiated with 12Gy, fixed in 2% paraformaldehyde for 2 hours at room temperature. After equilibration in 10 and 15% sucrose in PBS, larvae were frozen in OCT compound on coverslips on dry ice. Sections were cut with a cryostat at a nominal thickness of 14 □m and collected on Superfrost slides (BDH). Antisera used were zebrafish γH2AX—a kind gift of J. Amatruda[67]—and pATM (Rockland). GFP fluorescence in transplanted embryos was still easily visible in fixed embryos. Images were acquired with a confocal (Leica SP2) microscope and 63× oil immersion lens.

RNA Sequencing.

Nuclear RNA shorter than 200 nt was purified using mirVana™ microRNA Isolation Kit. RNA quality was checked on a small RNA chip (Agilent) before library preparation (Supplementary FIG. 23a). For Illumina hi Seq Version3 sequencing, spike RNA was added to each RNA sample in the RNA:spike ratio of 10,000:1 before library preparation and libraries for Illumina GA IIX were prepared without spike. An improved short RNA library preparation protocol was used to prepare libraries[68]. In brief, adenylated 3' adapters were ligated to 3' ends of 3'-OH short RNAs using a truncated RNA ligase enzyme followed by 5' adapter ligation to 5'-monophosphate ends using RNA ligase enzyme, ensuring specific ligation of undegraded short RNAs. cDNA was prepared using a primer specific to the 3' adapter in the presence of Dimer eliminator and amplified for 12-15 PCR cycles using a special forward primer targeting the 5' adapter containing additional sequence for sequencing and a reverse primer targeting the 3' adapter. The amplified cDNA library was run on a 6% polyacrylamide gel and the 100 bp band containing cDNAs up to 33 nt was extracted using standard extraction protocols. Libraries were sequenced after quality check on a DNA high sensitivity chip (Agilent). Multiplexed barcode sequencing was performed on Illumina GA-IIX (35 bp Single end reads) and Illumina Hi seq version3 (51 bp single end reads). Sequences of all the DDRNAs identified in this study will be available for free downloading by the time of publication at short read archive.

Statistical Analyses.

Results are shown as means plus/minus standard error (s.e.m.). p-value was calculated by Chi-squared test. QRT-PCR results are shown as means of a triplicate plus/minus standard deviation (s.d.) and p-value was calculated by Student's t-test as indicated. *indicates p-value<0.05.

Figure 34A:
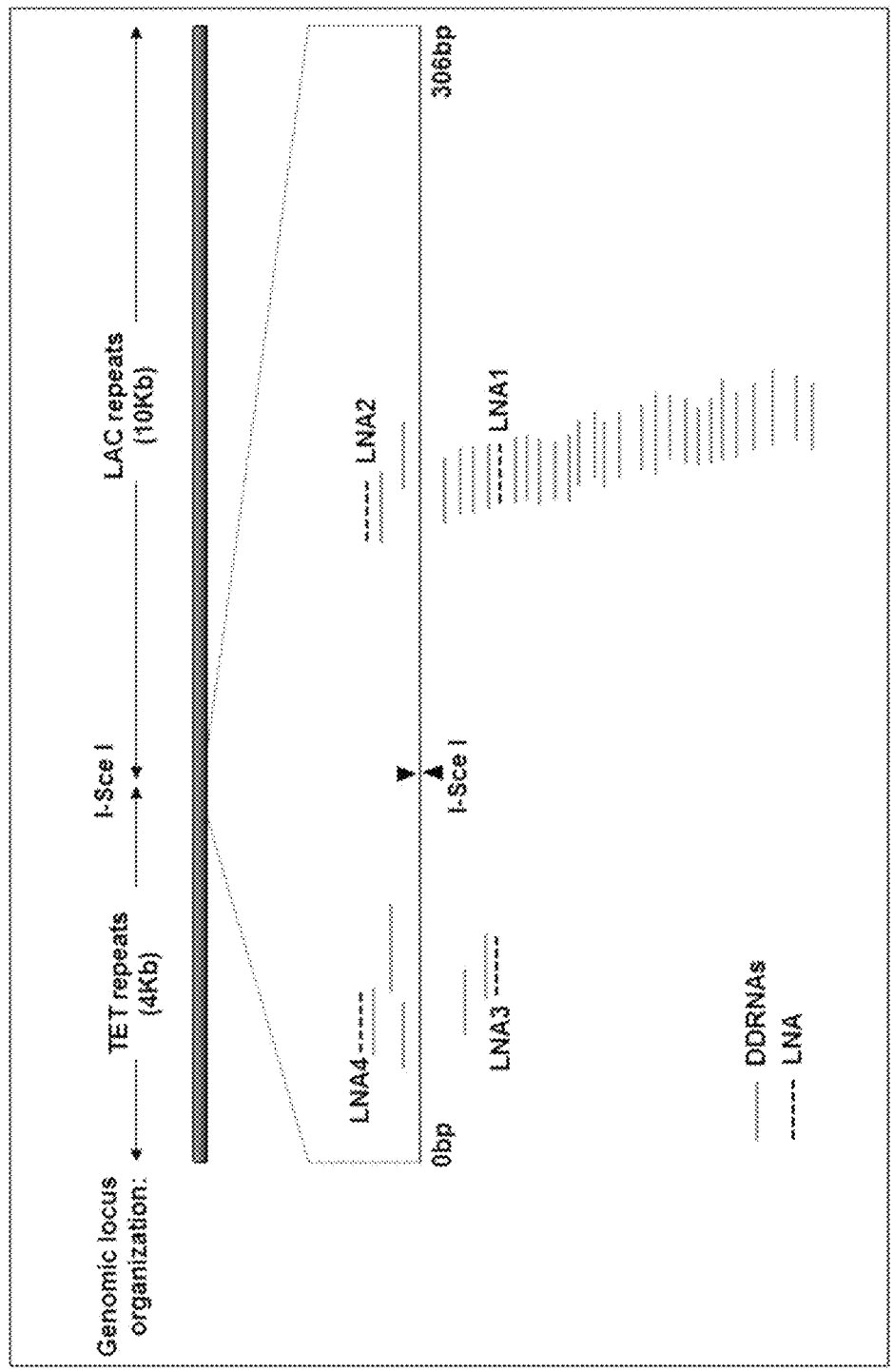
FIGS. 34A-34C|Sequence-specific inhibitory oligonucleotides (i.e. LNAs) transfection impairs DDR at the locus in cut cells. The scheme
Figure 34B:
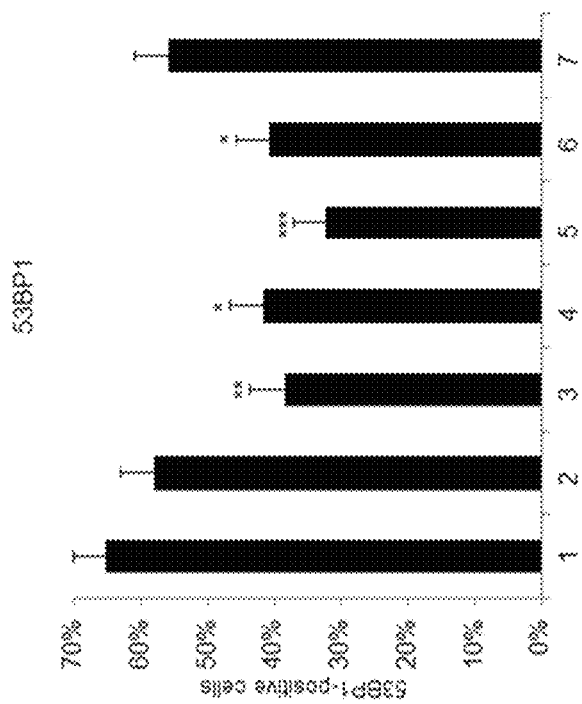

Results in FIGS. 34b and c are shown as means plus standard error (s.e.m.). p-value was calculated by Chi-squared test. *indicates p-value<0.05, indicates p-value<0.01, *indicates p-value<0.005.

Results in FIGS. 35-36 are shown as means plus standard error of the mean (s.e.m.). p-value was calculated by Chi-squared test. *indicates p-value<0.05, ***indicates p-value<0.001.

Short RNA Sequencing Data Statistical Analysis.

Statistical significance of downregulation of normalized miRNAs in Dicer and Drosha knockdown samples were calculated using the Wilcoxon signed-rank test.

The differences in the fraction of 22-23 nt vs total short RNAs at the locus between the wildtype, Dicer knockdown, and Drosha knockdown before and after cut was calculated by fitting a negative binomial model to the sRNA count data and performing a likelihood ratio test, keeping the fraction of 22-23 nt vs total short RNAs at the locus fixed across conditions under the null hypothesis and allowing it to vary between conditions under the alternative hypothesis.

LNA Sequences (for experiments in FIGS. 34 and 36).

```
LNA 1:
                                        (SEQ ID NO: 57)
TTATCCGCTCACAATTCCACAT

LNA 2:
                                        (SEQ ID NO: 58)
ATGTGGAATTGTGAGCGGATAA

LNA 3 (Cntrl in FIG. 36):
                                        (SEQ ID NO: 59)
ACTGATAGGGAGTGGTAAACT LNA 4:
                                        (SEQ ID NO: 60)
AGAGAAAAGTGAAAGTCGAGT LNA 5 (control in FIG. 34):
                                        (SEQ ID NO: 61)
CCCTAACCCTAACCCTAACCC LNA 6:
                                        (SEQ ID NO: 62)
GGGTTAGGGTTAGGGTTAGGG
```

Examples

Inactivation of DICER and DROSHA Inhibits DDR and Allows Senescent Cells to Re-Enter into Cell Cycle.

Figure 7A:
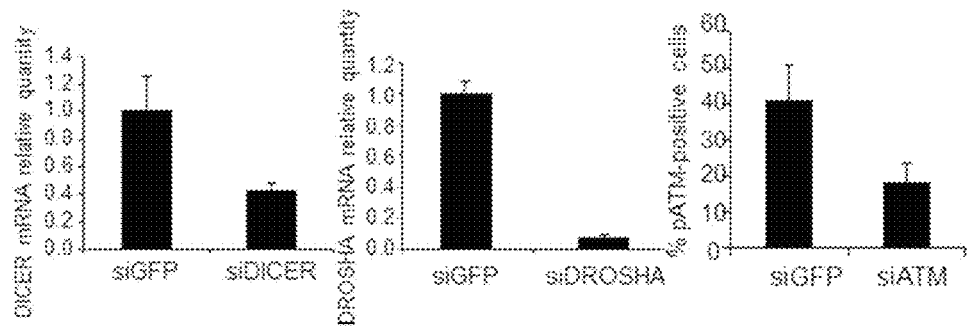
FIGS. 7A-7G|DICER or DROSHA inactivation in OIS cells allows escape from senescence and cell-cycle progression.
Figure 7B:
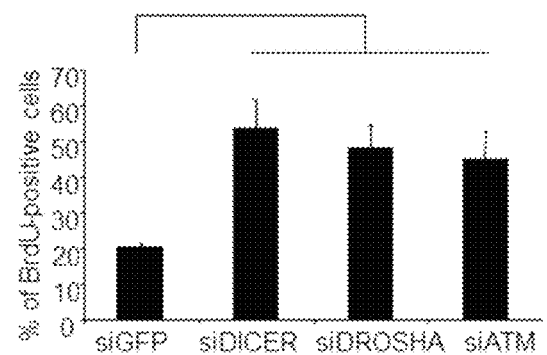
Figure 7C:
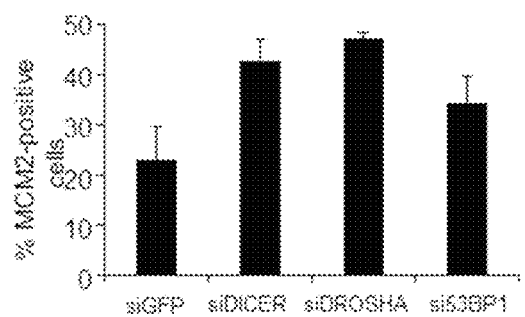
Figure 7D:
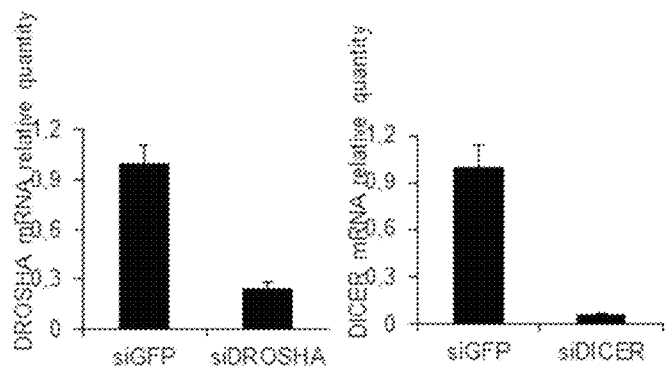
Figure 7E:
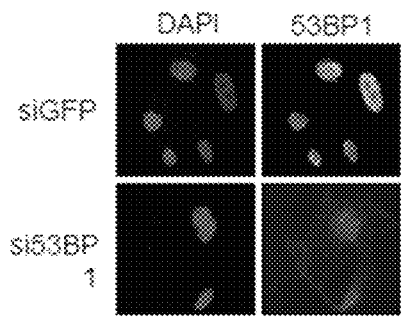
Figure 7F:
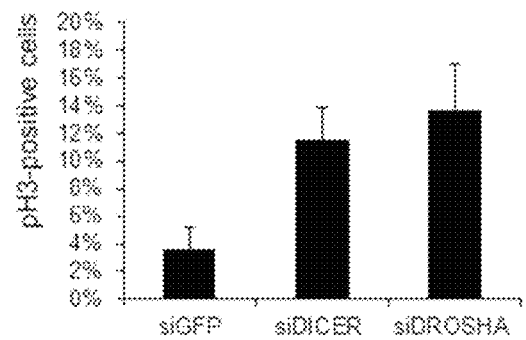
Figure 7G:
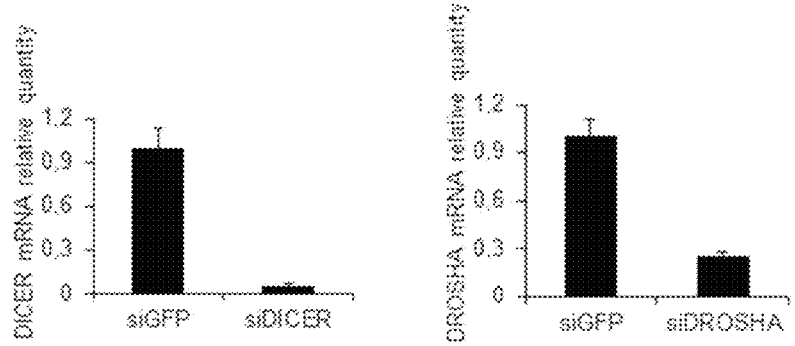
Figure 8A:
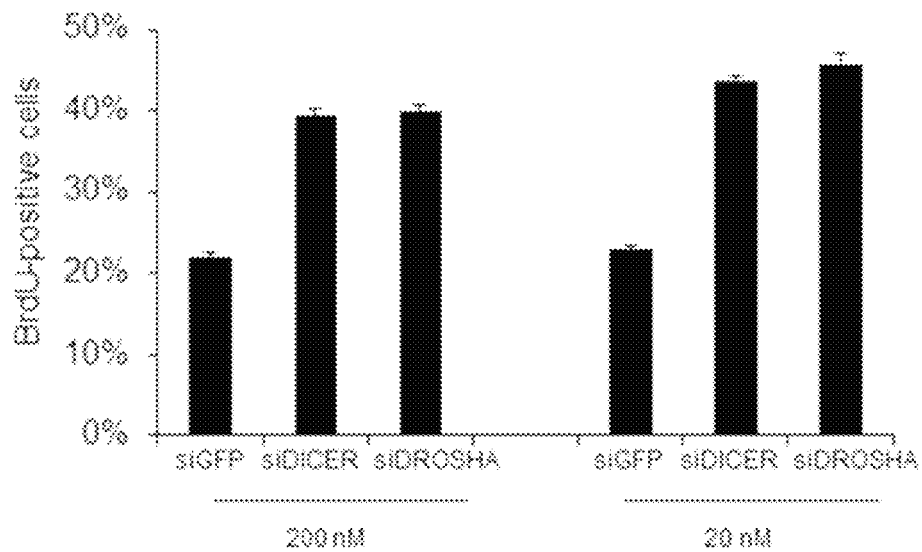
FIGS. 8A-8E|Different concentrations and individual siRNA against DICER or DROSHA in OIS cells reproducibly allow escape from senescence.
Figure 8B:
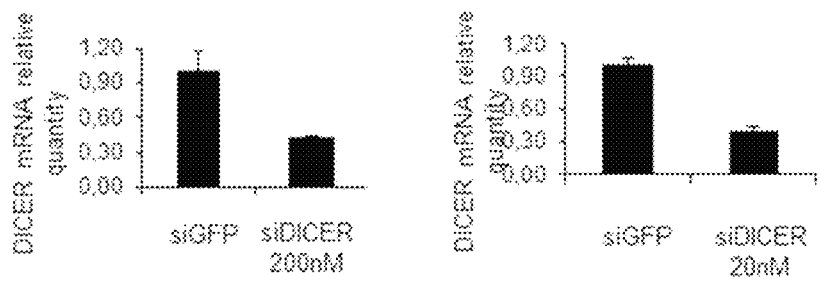
Figure 8C:
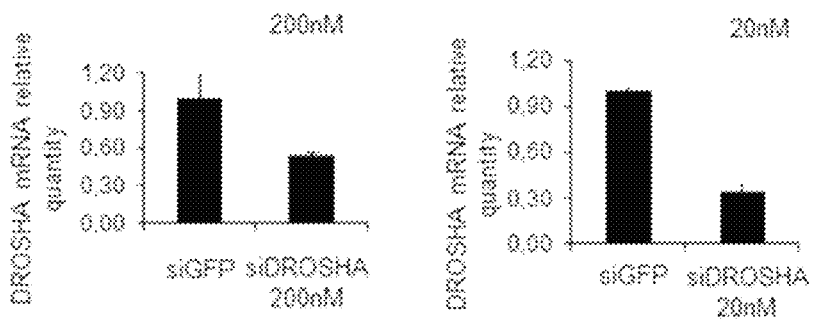
Figure 8D:
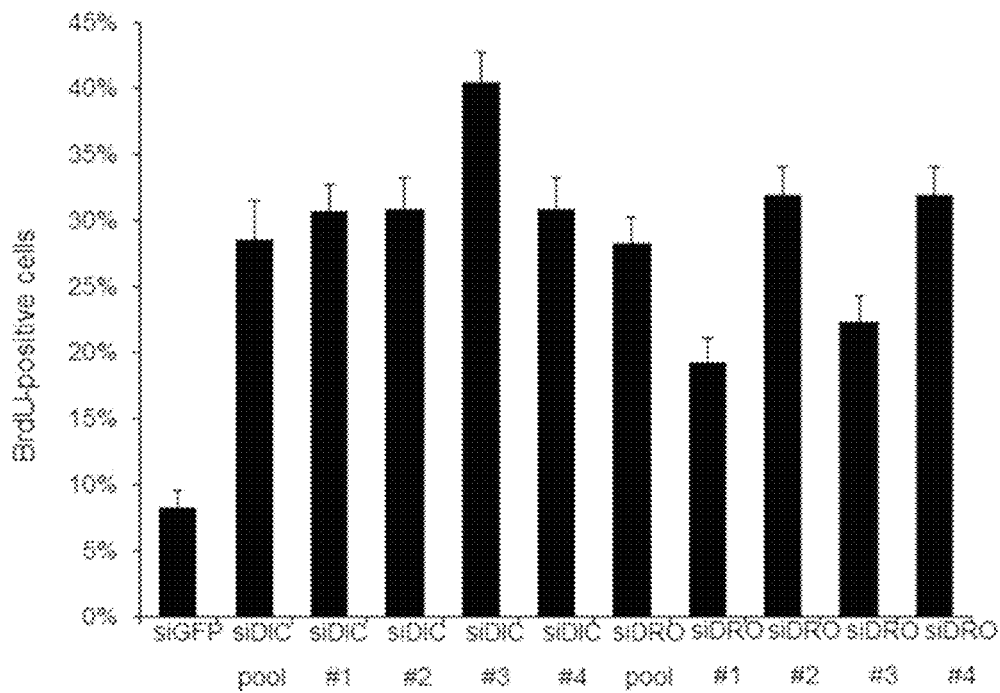
Figure 8E:
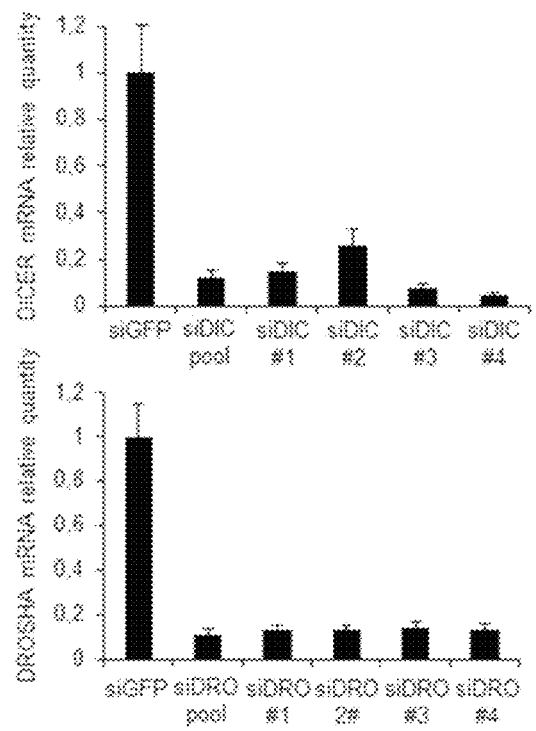

Oncogene-induced senescence (OIS) is a non-proliferative state characterized by a sustained DDR[20,21] (caused by high level of endogenous DNA damage) and senescence-associated heterochromatic foci (SAHF)[22]. Since the RNAi-machinery has been involved in heterochromatin formation[23], the authors investigated whether the inactivation of components of the RNAi machinery could have an impact on escape from senescence induced in human fibroblasts by transduction of H-RasV12 (referred here as OIS cells). The authors therefore suppressed the expression of DICER or DROSHA in OIS cells using a pool of small interfering RNAs (siRNA) and monitored cell-cycle progression into S-phase with BrdU labeling. The authors observed that DICER or DROSHA knockdown, as well as ATM knockdown used as positive control for escape from senescence[20] (Figure S1a), result in an increased fraction of BrdU-positive cells (FIG. 7B), re-expression of markers of chromosomal DNA replication (FIGS. 7C-7E) and entry into mitosis (FIGS. 7F-7G). These results could be reproduced over a range of siRNA concentrations (FIGS. 8A-8C) and with four individual siRNA oligonucleotides (FIGS. 8D and 8E). Perhaps unexpectedly however, in DICER- or DROSHA-inactivated cells the authors failed to detect any overt impairment in heterochromatin formation and SAHF components accumulation as detected by DAPI staining and by immunostaining and immunoblotting for the trimethylated form of the histone H3 (H3K9me3) (FIGS. 9A and 9B).

Figure 1B:
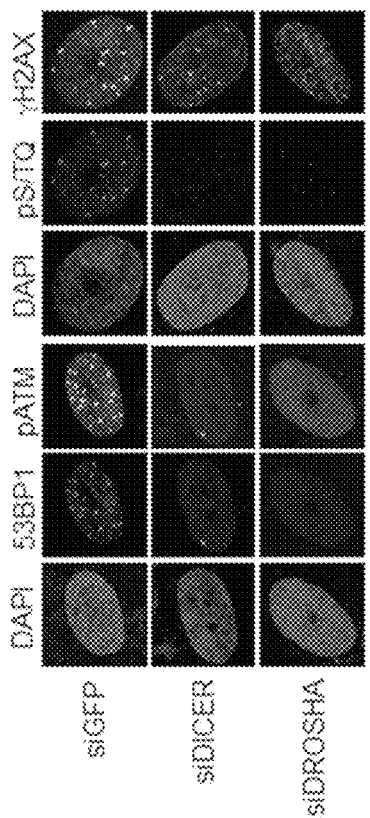
Figure 10A:
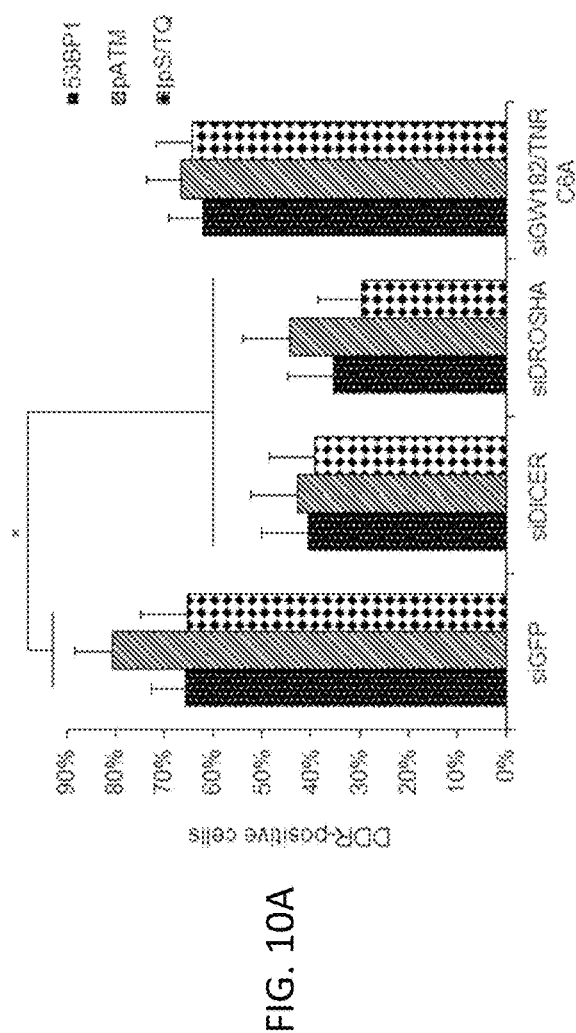
FIGS. 10A and 10B|DICER or DROSHA, but not GW182, inactivation in OIS cells impairs DDR foci formation.
Figure 10B:
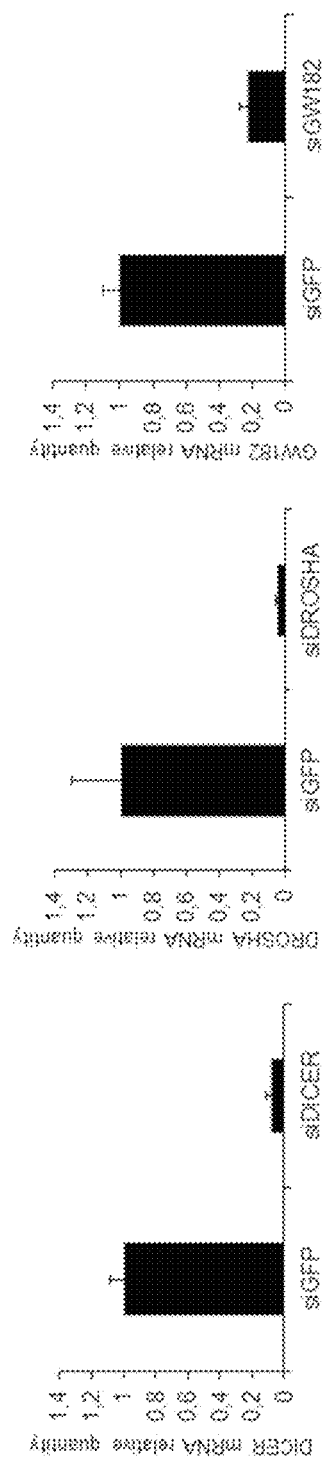
Figure 11A:
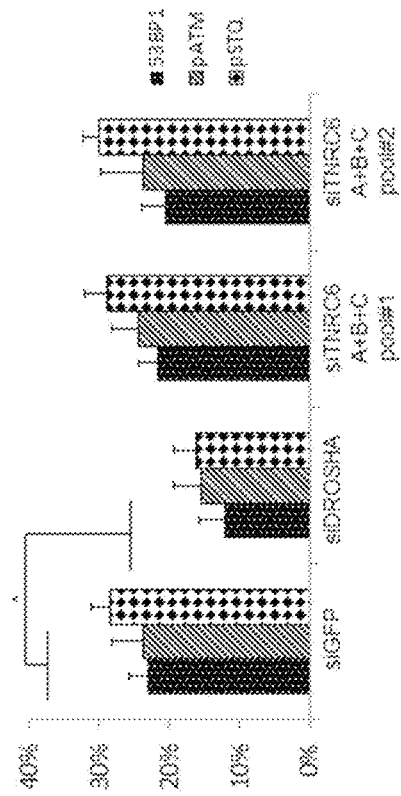
FIGS. 11A and 11B|Simultaneous inactivation of TNRC6A/GW182, TNRC6B and TNC6C in OIS cells does not affect DDR foci formation while DROSHA inactivation does.
Figure 11B:
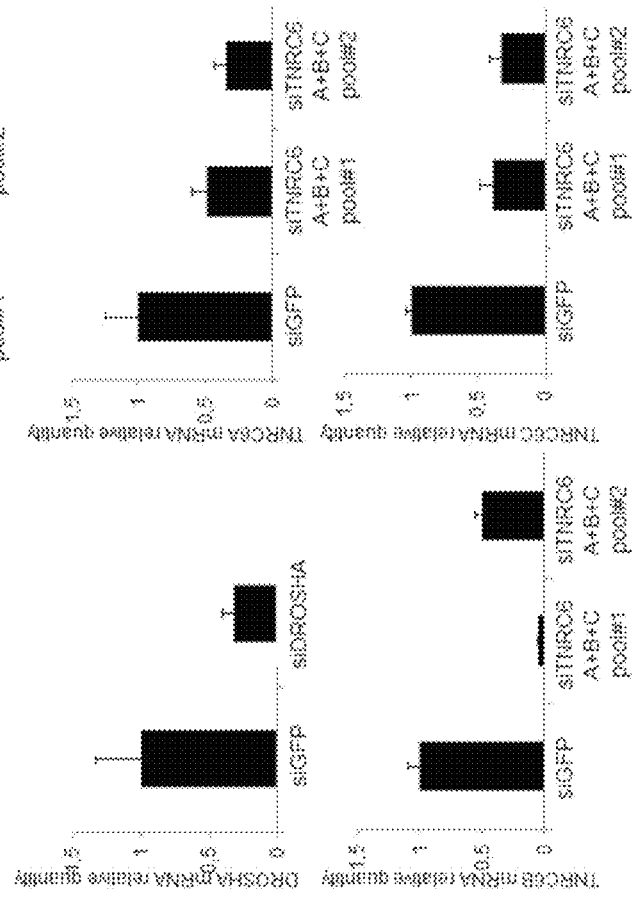

Since DDR plays a crucial role in the maintenance of the proliferative arrest in OIS cells[20,21], the authors monitored whether DICER or DROSHA inactivation had an impact on DDR foci maintenance. The authors therefore stained cells for markers of active DDR such as the autophosphorylated form of ATM (pATM), phosphorylated substrates of ATM and ATR (pS/TQ), 53BP1 and γH2AX. The authors observed that DICER or DROSHA inactivation significantly reduces the number of 53BP1, pATM and pS/TQ foci positive cells (FIGS. 1A, 1B, and 9A) even though 53BP1, ATM or H2AX protein levels are not reduced (FIG. 9C). The authors also observed that the percentage of γH2AX-positive cells did not show a significant variation, although the intensity of γH2AX foci was generally reduced (FIGS. 1A and 1B). These effects could be observed over a range of siRNA concentrations (FIGS. 9D-9F). Importantly, inactivation of GW182/TNRC6A, the main component of the RNAi machinery involved in mRNA translational control, did not impact on DDR foci detection (FIGS. 10A and 10B), nor the simultaneous inactivation of all three GW182-like proteins TNRC6A, B and C with two independent pools of siRNAs (FIGS. 11A and 11B). Therefore, DICER or DROSHA inactivation impairs DDR signaling and overcomes the DDR-induced proliferative arrest of OIS cells.

DICER or DROSHA Inactivation Impairs Ionizing Radiation-Induced DDR Foci Formation.

Figure 1C:
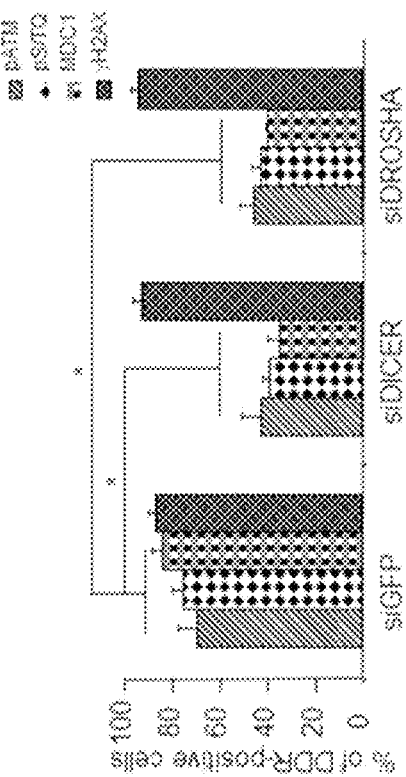
Figure 1D:
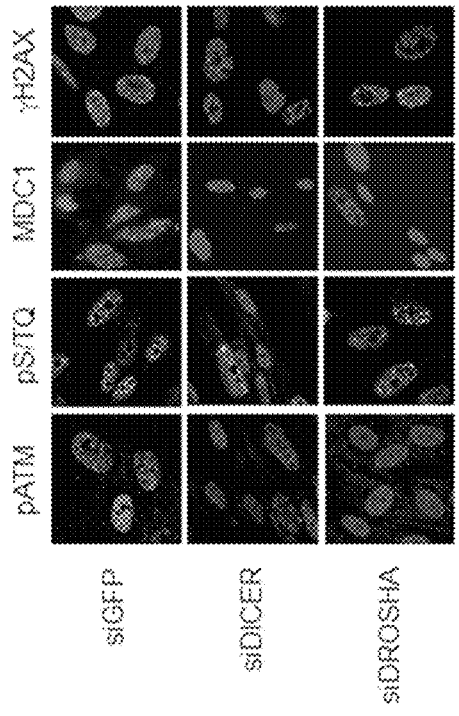
Figure 12A:
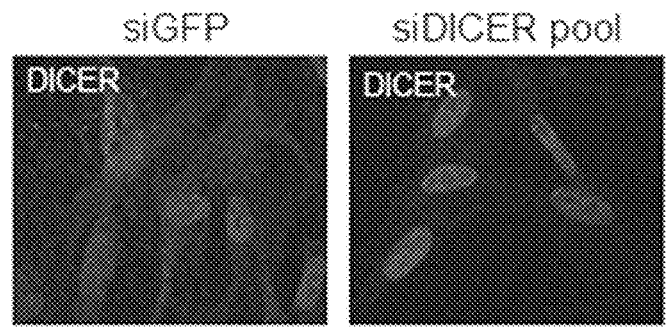
FIGS. 12A-12G|DICER or DROSHA inactivation in HNF impairs IR-induced DDR foci formation.
Figure 12B:
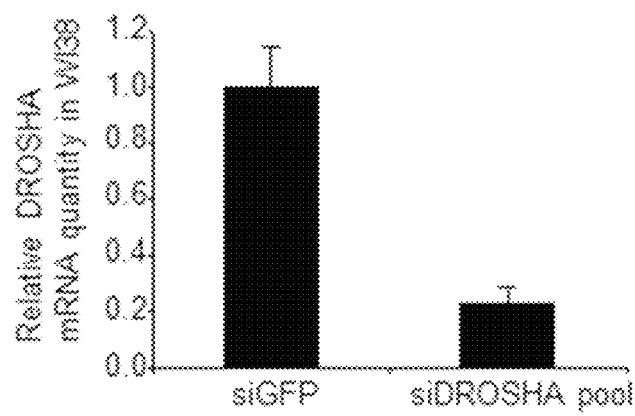
Figure 12C:
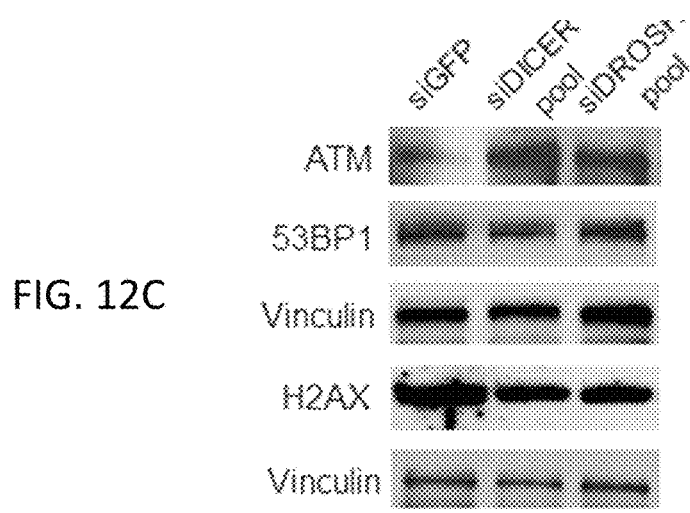
Figure 12D:
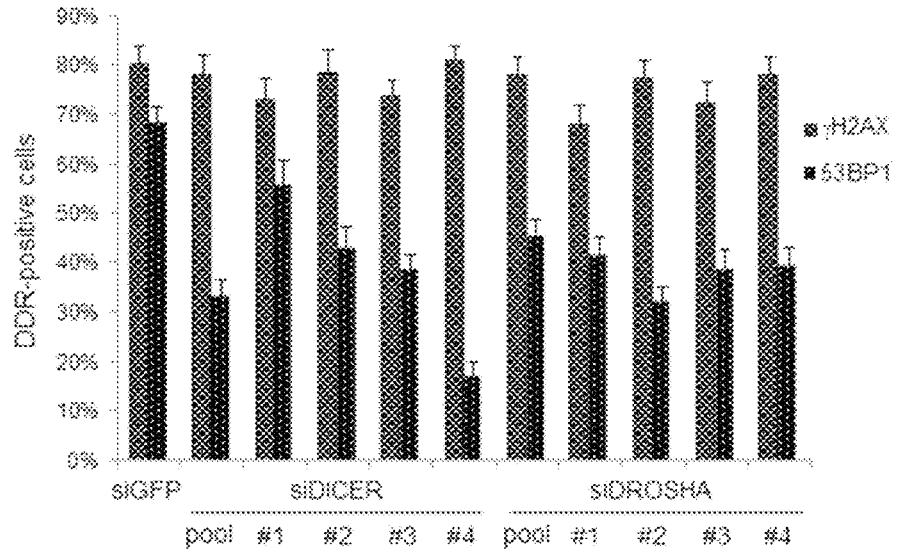
Figure 12E:
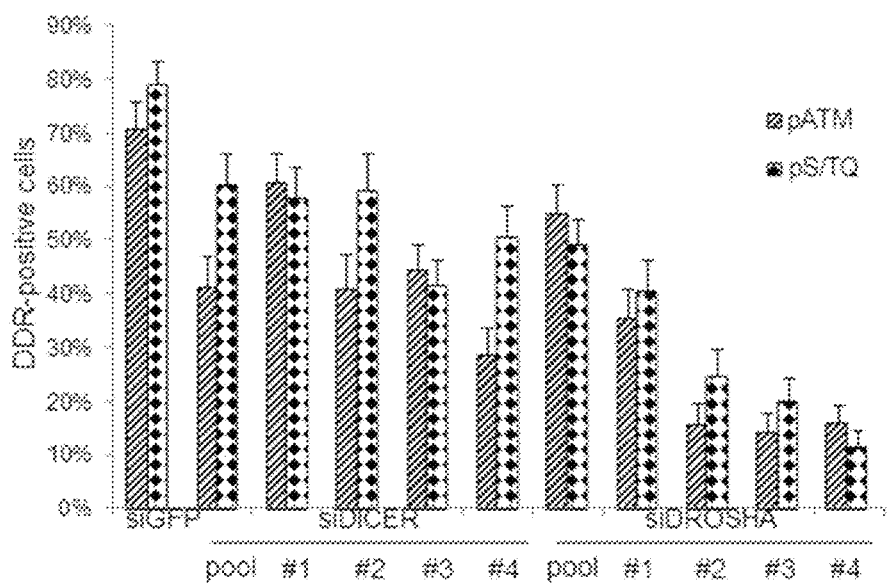
Figure 12F:
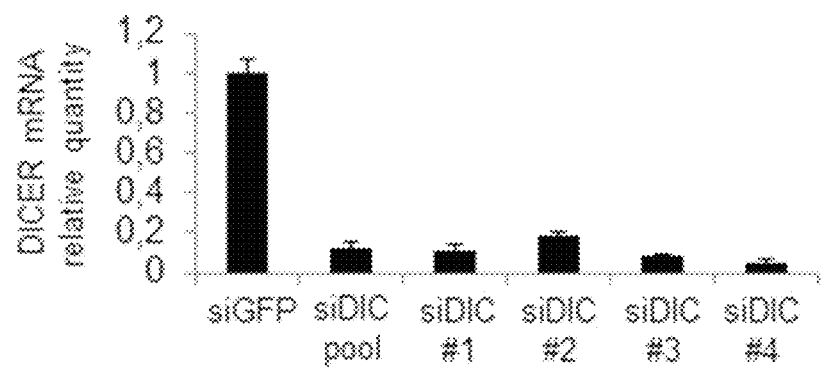
Figure 12G:
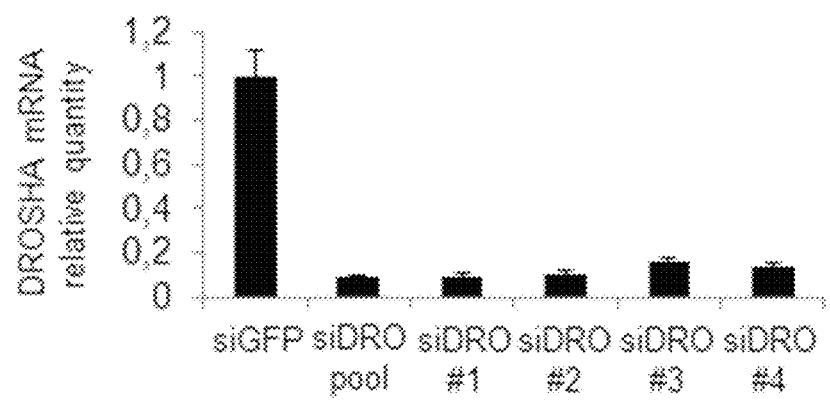
Figure 13A:
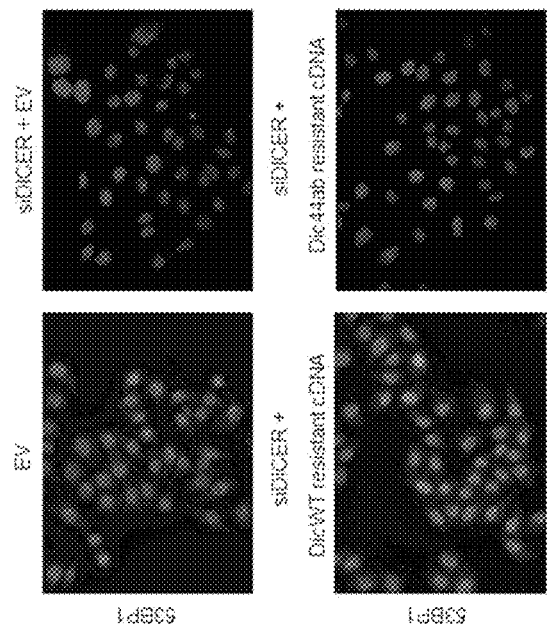
FIGS. 13A-13D|53BP1 foci formation is delayed upon DICER or DROSHA knockdown and impaired DDR foci formation is rescued by wild type but not mutant DICER.
Figure 13B:
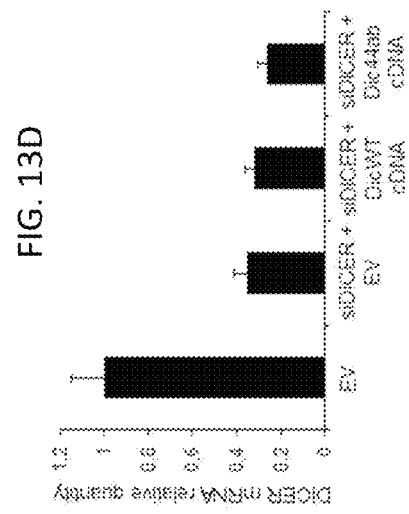
Figure 13C:
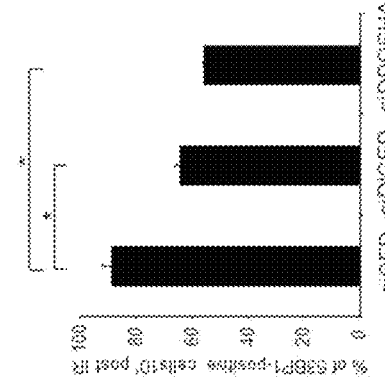
Figure 13D:
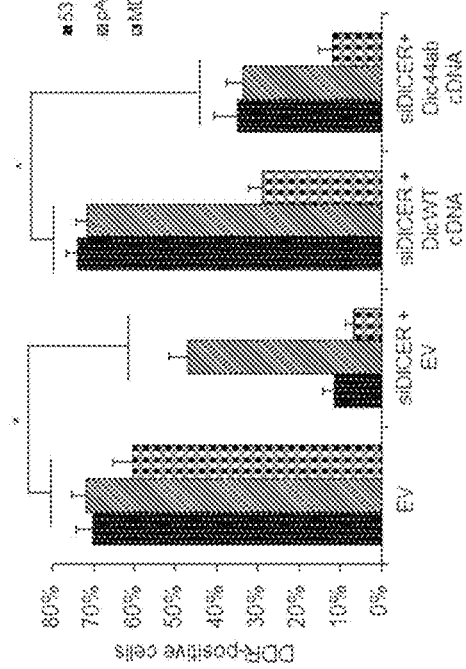

The authors next asked whether the involvement of DICER and DROSHA in DDR activation is specific for the senescence condition or whether DICER or DROSHA inactivation has also an impact on ionizing radiation (IR)-induced DDR activation in proliferating non-senescent cells. Therefore, the authors transiently inactivated DICER or DROSHA by a pool of siRNA in human normal fibroblasts (HNF-WI38; FIGS. 12A and 12B), exposed them to IR and a few hours later the authors stained them for markers of activated DDR. The authors observed that, despite not reduced levels of protein expression (FIG. 12C), formation of pATM, pS/TQ, MDC1, but not γH2AX, foci are impaired in DICER- or DROSHA-inactivated HNF (FIGS. 1C and 1D). These observations can be reproduced by using four individual siRNAs (FIGS. 12D-12G) and in a different HNF cell line (BJ, data not shown). Under these conditions (DICER- or DROSHA-knocked down HNF analyzed 7 hours post IR), the authors did not observe the dramatic impairment of 53BP1 foci previously observed in OIS cells. However, an analysis performed at earlier time points (10' after IR) showed a significant reduction of 53BP1 foci formation in DICER- or DROSHA-inactivated HNF (FIG. 13A), suggesting that DICER or DROSHA inactivation delays 53BP1 foci formation.

In order to exclude off target effects, the authors expressed an RNAi-resistant form of DICER in DICER-knocked down HeLa cells. The authors observed that re-expression of wild-type DICER, but of not a mutant allele (DICER44ab) previously shown to abolish its RNA endonuclease activity[24], allows DDR foci formation to an extent similar to wild type cells, thus confirming DICER-dependency of the effects observed (Figure S 7b-d). Finally, the effects observed are independent of mRNA translational control, as GW182 knockdown has no significant impact on DDR foci formation (FIGS. 14A-14C), consistent with the results in OIS cells (FIGS. 10A and 10B). As an additional control, the simultaneous inactivation of TNRC6A, B and C or DICER in Hela cells expressing a reporter mRNA encoding for Red Fluorescent Protein (RFP) carrying three binding sites for miR-126, used as a sensor for microRNA-dependent translational repression, showed that both GW-like proteins and DICER inactivation result in comparable RFP up-regulation, due to the abolished miR-126-dependent RFP translational repression (FIGS. 15A, 15B, and 15D); nevertheless, only DICER inactivation affects DDR foci stability (FIG. 15C).

Figure 1E:
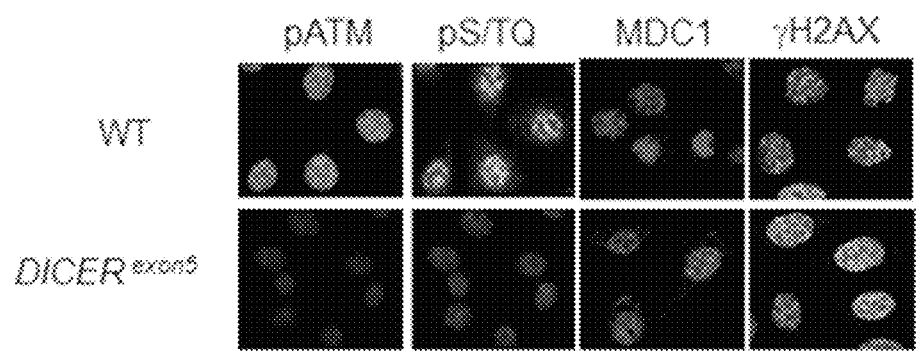
Figure 1F:
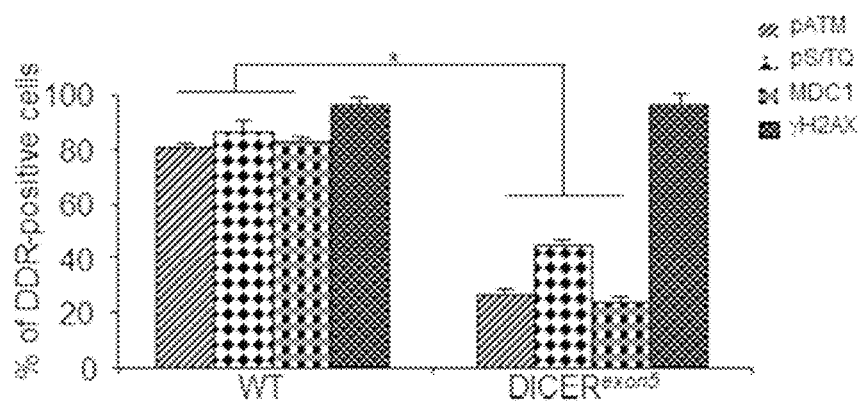
Figure 16A:
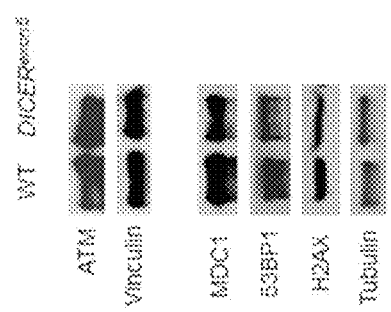
FIGS. 16A-16C|DDR factors are expressed but 53BP1 foci formation is delayed in DICER$^{exon5}$-hypomorphic RKO cells.
Figure 16B:
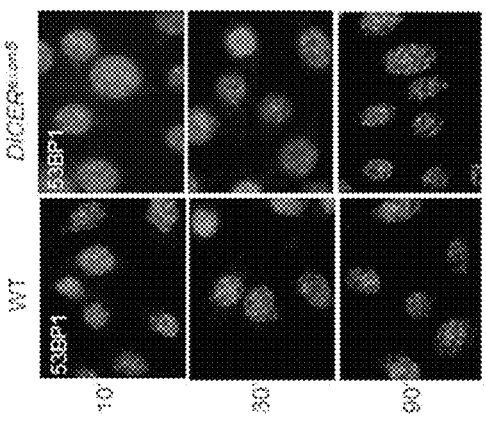
Figure 16C:
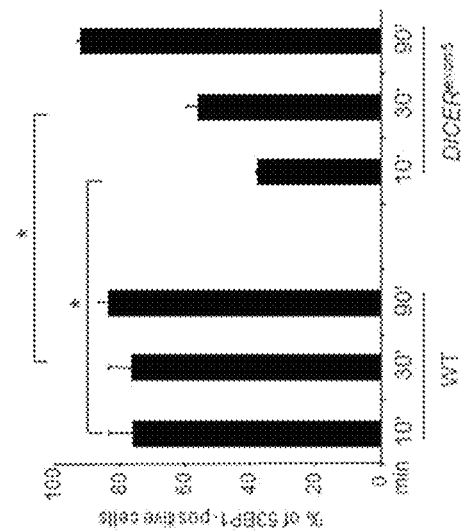
Figure 17A:
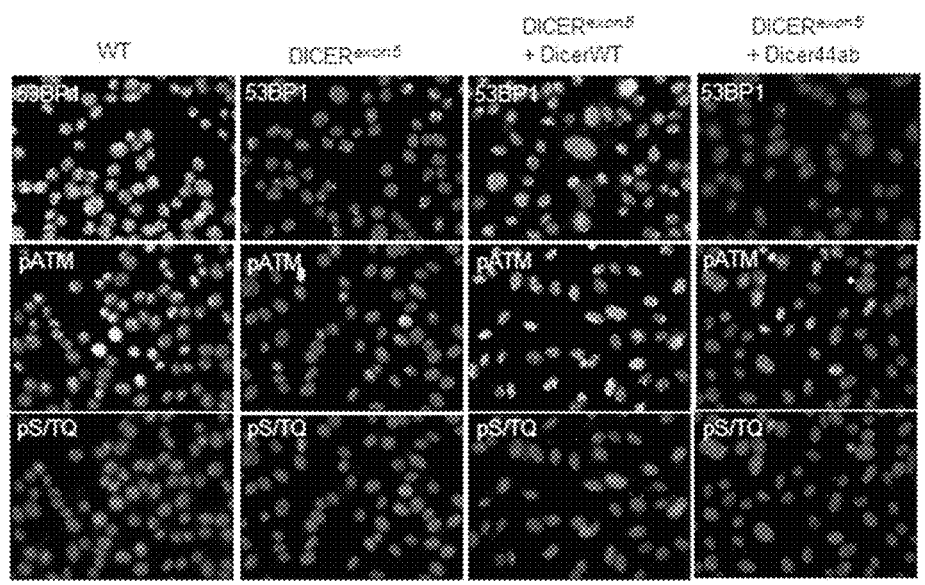
FIGS. 17A and 17B|Impaired DDR foci formation in DICER$^{exon5}$-hypomorphic cells is rescued by wild type but not mutant DICER.
Figure 17B:
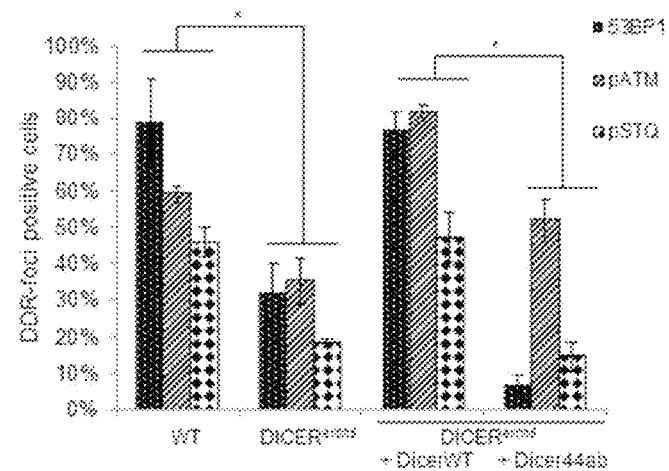

To further confirm the involvement of DICER in DDR activation, the authors used a colon cancer cell line (RKO) carrying a homozygotic genetic deletion of exon 5 in DICER gene and therefore expressing a hypomorphic allele of DICER (DICER$^{exon5}$); this cell line is defective in microRNAs maturation[25]. In DICER$^{exon5}$-hypomorphic cells, the level of expression of ATM, MDC1, 53BP1 or H2AX proteins is not reduced (FIG. 16A). However, while in wild-type (WT) cells IR induces pATM, pS/TQ, MDC1 and γH2AX foci, in DICER$^{exon5}$-hypomorphic cells DDR foci formation is impaired (FIGS. 1E and 1F). In a time-course experiment, the authors observed that 53BP1 foci formation is delayed in DICER$^{exon5}$-hypomorphic cells (FIGS. 16B and 16C). Also in this system, the authors observed that γH2AX foci are only mildly affected (FIGS. 1E and 1F). The defects observed in DICER$^{exon5}$-hypomorphic cells could be reversed by the re-introduction of wild-type but not of an endonuclease mutant allele of DICER (DICER44ab) (FIGS. 17A and 17B). Similar conclusions were reached in an additional cell line (HCT116) carrying the same DICER deletion (data not shown).

Figure 18B:
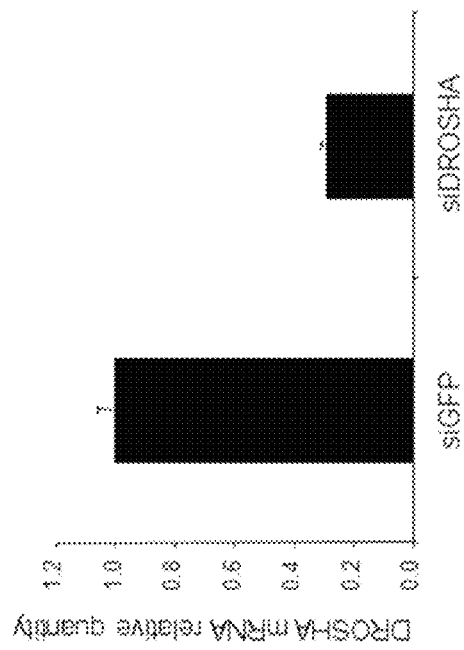
FIGS. 18A-18C|ATM activation by autophosphorylation is impaired in DICER and DROSHA-inactivated cells.
Figure 18A:
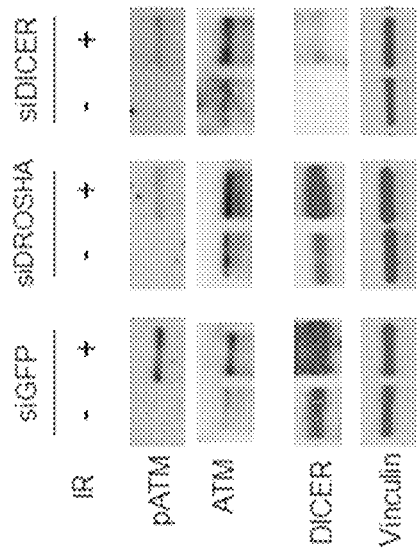
Figure 18C:
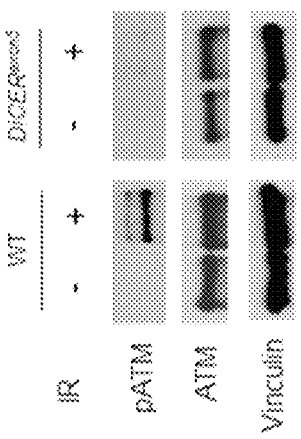

Next, the authors tested if the absence of DDR foci observed in DICER- or DROSHA-inactivated cells was due to a defect in actual DDR activation or DDR foci assembly. Therefore, the authors performed a set of immunoblot analyses both in DICER- or DROSHA-interfered HNF and in DICER$^{exon5}$-hypomorphyc cell lines. The authors' analyses revealed that IR-induced ATM autophosphorylation is impaired in DICER- or DROSHA-inactivated fibroblasts (FIGS. 18A and 18B) and in irradiated RKO DICER$^{exon5}$-hypomorphic cells, compared to wild-type cells (FIG. 18C). This indicates that DICER and DROSHA control ATM activation and not just its accumulation in foci. Combined, these results reveal that DICER or DROSHA inactivation impairs DDR activation induced by exogenous sources of DNA damage in manner independent from canonical RNAi translational repressors (GW-like proteins).

DICER or DROSHA Inactivation Impairs G1/S and G2/M DNA Damage Checkpoints.

Figure 19A:
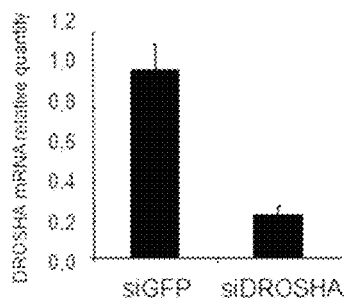
FIGS. 19A-19G|DICER or DROSHA knockdown impairs G1/S checkpoint. DICER, DROSHA and 53BP1 knockdowns in WI38 cells were monitored by siRNA pools in WI38 cells were monitored by QRT-PCR FIG. 19A, immunoblot FIG. 19B and immunofluorescence FIG. 19C, respectively.
Figure 19B:
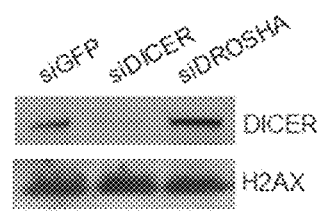
Figure 19C:
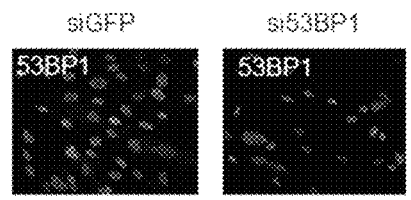
Figure 19D:
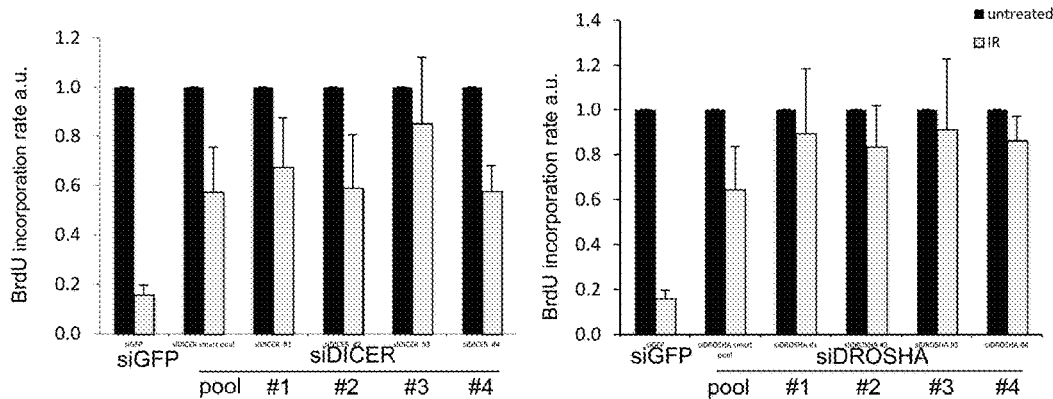
Figure 19E:
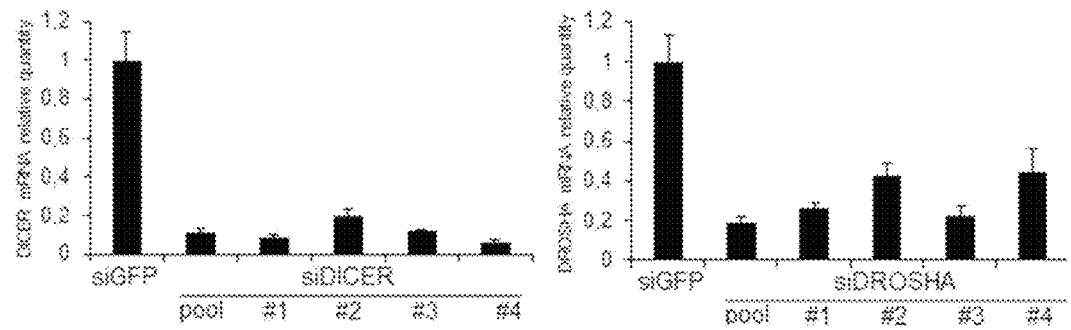
Figure 19F:
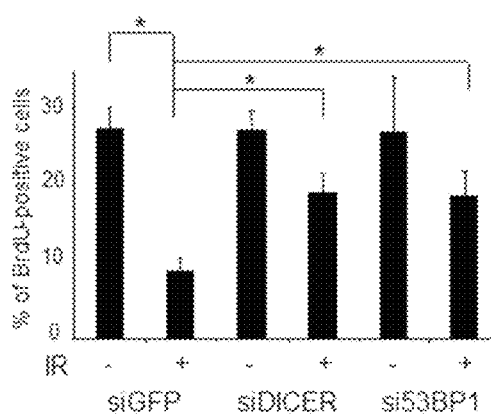
Figure 19G:
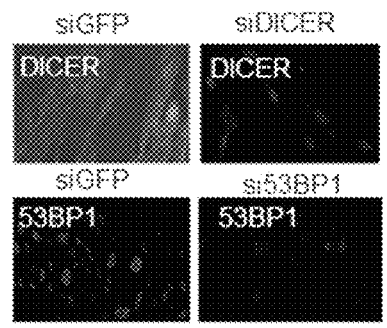
Figure 20A:
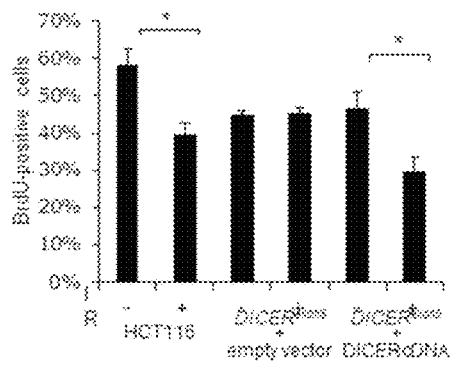
FIGS. 20A-20G|Loss of G1/S and G2/M checkpoint activation in DICER knocked-down cells.
Figure 20B:
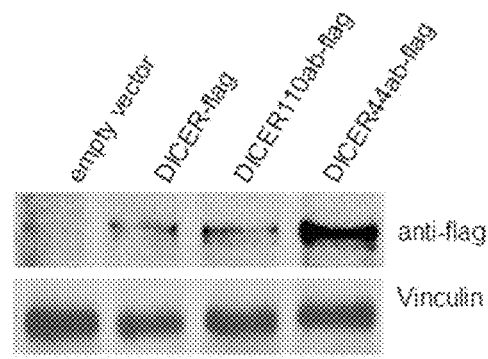

DNA damage elicits DDR signal transduction leading to checkpoint-dependent cell-cycle arrest at two critical transition steps: the G1/S checkpoint and the G2/M checkpoint'. The authors tested whether impaired DDR activation in DICER- or DROSHA-inactivated cells has an impact on G1/S and G2/M checkpoints. To test the G1/S checkpoint-dependent arrest, cells were irradiated and pulse-labeled with BrdU. The authors observed that DICER- and DROSHA-inactivated HNF (WI38; FIGS. 19A and 19B) have an impaired irradiation-induced G1/S-phase arrest compared to control cells (FIG. 2a) and that the extent of checkpoint deficiency is comparable to that of 53BP1-interfered cells, used as a positive control[26] (FIGS. 2A and 19C). G1/S checkpoint impairment was confirmed with four individual siRNA oligonucleotides (FIGS. 19D and 19E) and in two additional HNF cell lines (MRC-5 and BJ) in separate sets of experiments (FIGS. 19F and 19G, and data not shown). Consistent with the results in HNF, DICER$^{exon5}$-hypomorphic cells, from two distinct cell lines (RKO and HCT116; FIGS. 2B and 20A, respectively), also show an impaired G1/S transition arrest. To confirm the dependency of the checkpoint on DICER in these cell lines, the authors re-expressed wild-type DICER-cDNA in DICER$^{exon5}$-hypomorphic cells. Indeed, DICER cDNA expression restored the G1/S checkpoint in both DICER$^{exon5}$-hypomorphic cell lines (FIGS. 2B and 20A). Next, the authors asked if the RNA-endonuclease activity of DICER is required for the DNA damage-induced checkpoint activation. With this aim, the authors complemented DICER$^{exon5}$-hypomorphic cells with two distinct DICER mutants carrying the amino acid substitution Asp44 to Ala44 (DICER44ab) or Glu110 to Ala110 (DICER110ab) known to abolish DICER RNA endonuclease activity[24]. While wild-type DICER expression rescued the G1/S checkpoint defect of DICER$^{exon5}$-hypomorphic cells, both DICER mutants failed to do so (FIG. 2B), despite similar levels of DICER expression (FIG. 20B). The authors conclude that the RNA processing activity of DICER is necessary to enforce the G1/S checkpoint.

Figure 20C:
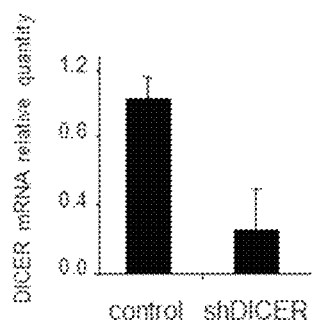
Figure 20D:
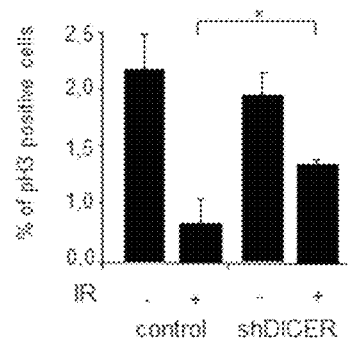
Figure 20E:
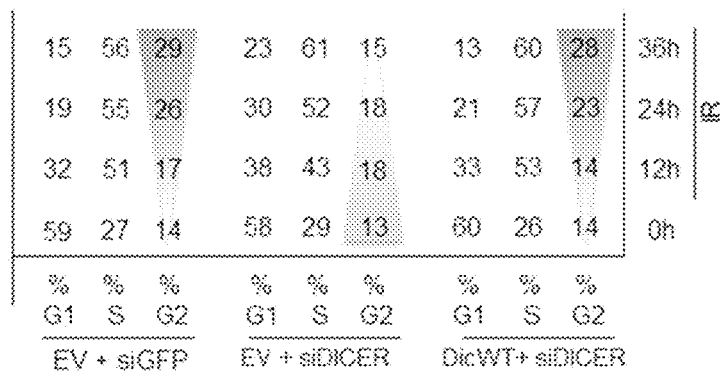
Figures 20F, 20G:
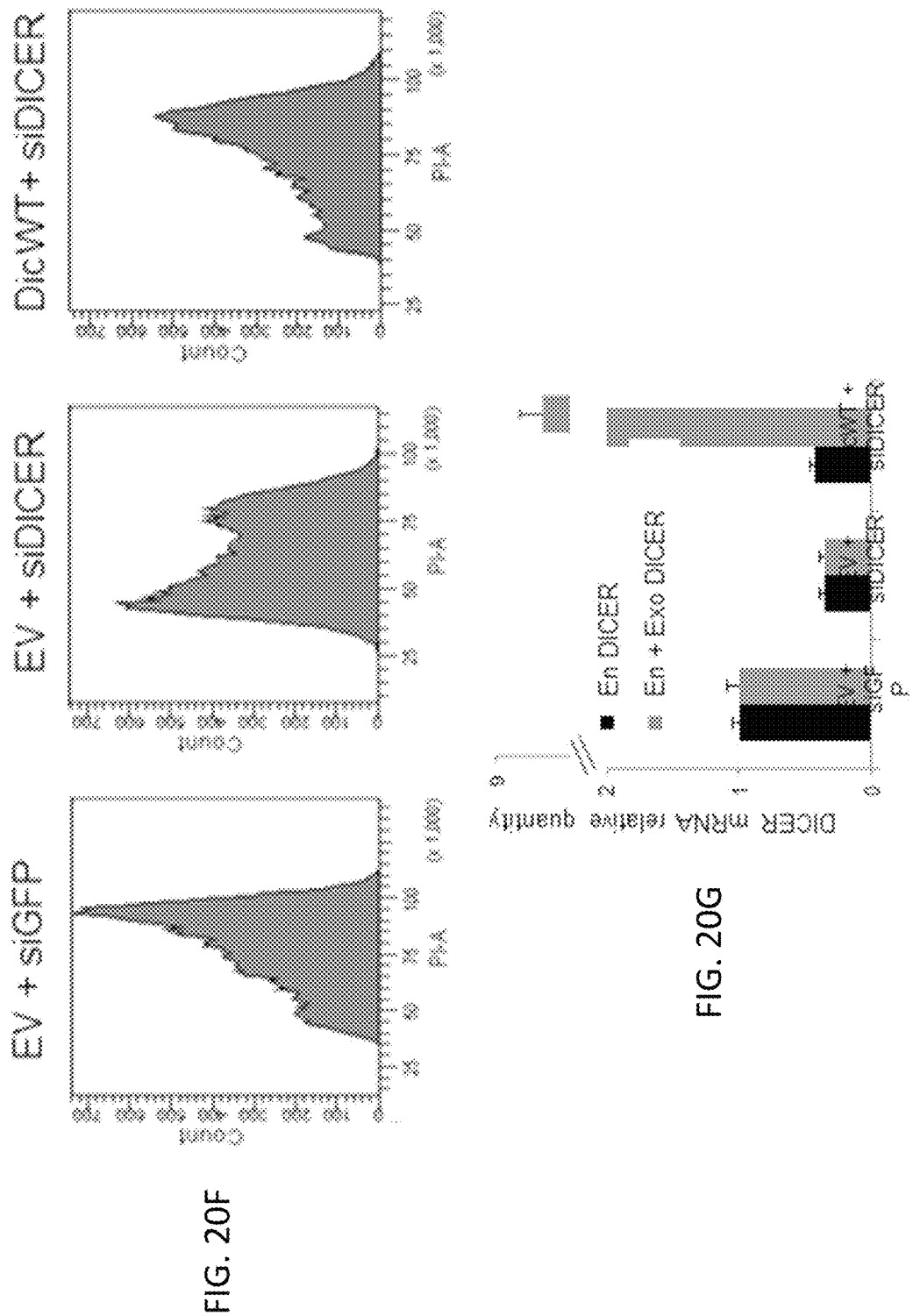

The authors also tested whether DICER is required to arrest cell-cycle progression at the G2/M boundary following DNA-damage. Thus, the authors suppressed DICER, or p53 as positive control, in HEK293 cells and the authors tested G2/M checkpoint activation by monitoring the cell-cycle progression profile over time through Fluorescence-Activated Cell Sorting (FACS). As expected, irradiated empty-vector (EV) transfected cells progressively accumulate in the G2 phase of the cell cycle, as a consequence of the checkpoint enforcement. Differently, DICER, as well as p53 knocked-down cells, did not arrest upon DNA damage and passed through the G2/M transition (FIGS. 2C and 2D). This result was further confirmed by monitoring the percentage of mitotic cells in control and DICER-inactivated cells following IR, based on histone H3 phosphorylation (pH3) (FIGS. 20C and 20D)[27]. Furthermore, the defect in G2/M checkpoint activation in DICER-knocked down cells could be rescued by the expression of a siRNA-resistant DICER expressing construct (FIGS. 20E-20G).

These results indicate that DICER-inactivated cells are deficient in the activation of both G1/S and G2/M checkpoints and that DICER's RNA processing activity is necessary to enforce the checkpoint after DNA damage.

DICER Inactivation in Zebrafish Impairs DDR Activation in Vivo.

To study if DICER is required for DDR activation upon irradiation in a living organism, the authors tested the impact of DICER inactivation in *Danio rerio* (zebrafish) larvae, as a model system. Zebrafish embryos were injected with morpholino oligonucleotides against Dicer1. Efficiency of Dicer1 inactivation was assessed by the ability of the morpholino oligonucleotide to block microRNA maturation and therefore impede the suppression of the co-injected reporter RFP-miR-126[28]. In addition, the authors investigated the levels of six different mature microRNAs using QPCR to confirm inactivation of Dicer1. Larvae originated from embryos injected with morpholino oligonucleotides against Dicer1 displayed upregulated RFP expression and the developmental defects previously reported for Dicer1-inactivated larvae[29] (FIGS. 21A and 21B) together with reduced levels of microRNAs (FIGS. 21C and 21D). Irradiated larvae were stained with antibodies against pATM and γH2AX. Not irradiated larvae showed no or weak staining (FIGS. 3A-3C). Irradiation induced a strong pATM and γH2AX activation in all the cells throughout the sections of wild-type larvae head. Differently, irradiated Dicer1 morpholino-injected larvae showed a dramatic impairment both in pATM and γH2AX signal (FIG. 3A). The observed impact on γH2AX suggests a stronger dependency of γH2AX on Dicer1 in zebrafish in vivo, compared with cultured mammalian cells. An immunoblot analysis of protein extracts from wild-type and Dicer1 morpholino-injected larvae treated in parallel showed that the impairment in pATM and γH2AX accumulation is present in the whole animal (FIG. 3B). The differential response to irradiation of cells with reduced Dicer1 activity due to morpholino injection versus Dicer1 proficient cells was further confirmed in reciprocal cell transplantation experiments. Briefly, cells from embryos injected with Dicer1 morpholino and mRNA encoding for GFP were transplanted at blastula stage into control uninjected embryos. Chimaeric larvae were irradiated at 3 days post fertilization (dpf) and stained with antibodies against γH2AX (FIG. 3C). In the reciprocal experiment, control cells from embryos injected with mRNA encoding for GFP were transplanted into Dicer1 morpholino injected embryos. Chimaeric larvae were irradiated as above and stained with antibodies against γH2AX. In both cases, cells with reduced Dicer1 activity displayed reduced γH2AX signals compared to their neighboring, Dicer1-proficient cells. (FIG. 3C). The authors conclude that Dicer1 is required for DDR activation in vivo in living zebrafish larvae.

In an in Vitro Cell System DDR Foci are Sensitive to RNase A and DICER and DROSHA RNA Products Allow DDR Foci Reformation.

Figure 4A:
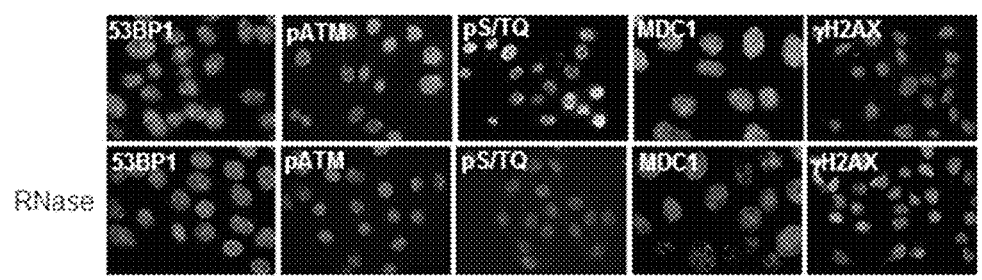
FIGS. 4A-4E|Irradiation-induced DDR foci are sensitive to RNase A treatment and are restored by short and DICER RNA products.
Figure 4B:
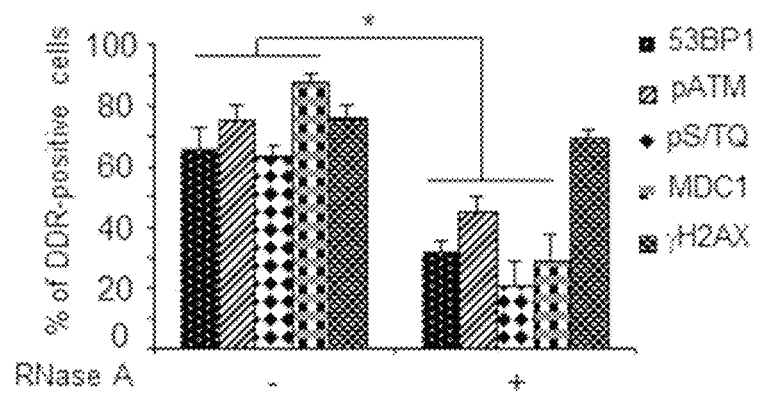

The authors then sought an experimental system amenable for the study of the potential direct contribution of DICER and DROSHA RNA products in DDR activation. It has been previously shown that mammalian cells can withstand a transient membrane permeabilization and RNase treatment. This approach allowed the study of the contribution of RNA to heterochromatin structure and protein association with chromatin[30,31]. The authors therefore utilised this technique to address the contribution of RNA in DDR activation. IR-exposed human cells (HeLa) were permeabilized by a mild detergent and treated with the broad-specificity RNA nuclease RNase A. This treatment leads to the degradation of both messenger RNAs and miRNAs including the mRNAs of DDR genes (FIGS. 22A and 22B), without significantly affecting DDR protein levels (FIG. 22C). Untreated and RNase A-treated irradiated cells were stained for markers of DDR activation. The authors observed that RNA degradation strongly impairs 53BP1, pATM, pS/TQ and MDC1 foci formation (FIGS. 4A and 4B). This result is consistent with the reported sensitivity of 53BP1-GFP to ribonuclease treatment[31]. Similar to the authors' observations in DICER- and DROSHA-inactivated cells, γH2AX accumulation is only slightly affected by RNase A (FIGS. 4A and 4B). Noteworthy, unperturbed γH2AX signals indicate that RNase A treatment does not dramatically alter chromatin structure or nuclear integrity. Intriguingly, 53BP1, MDC1 and γH2AX triple staining shows that RNase A reduces 53BP1 and MDC1 accumulation at individual γH2AX-foci, which are instead maintained (FIG. 22D), thus suggesting that RNA molecules act to favor MDC1 and 53BP1 focus formation once H2AX has been phosphorylated.

Figure 23A:
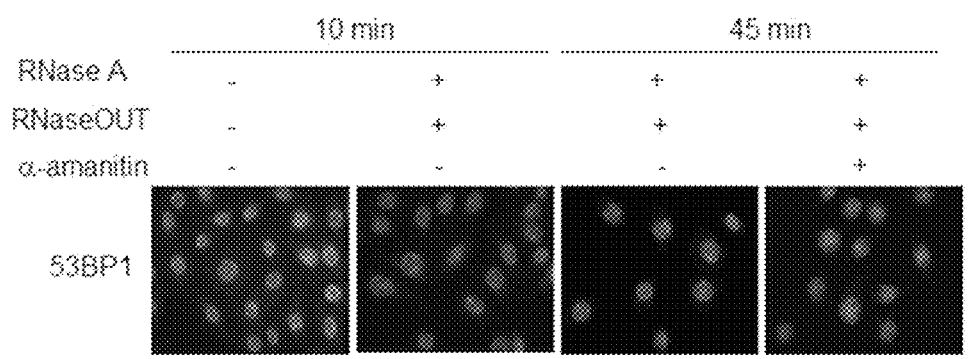
FIGS. 23A and 23B|α-amanitin inhibits spontaneous DDR foci reformation following RNase A treatment.
Figure 23B:
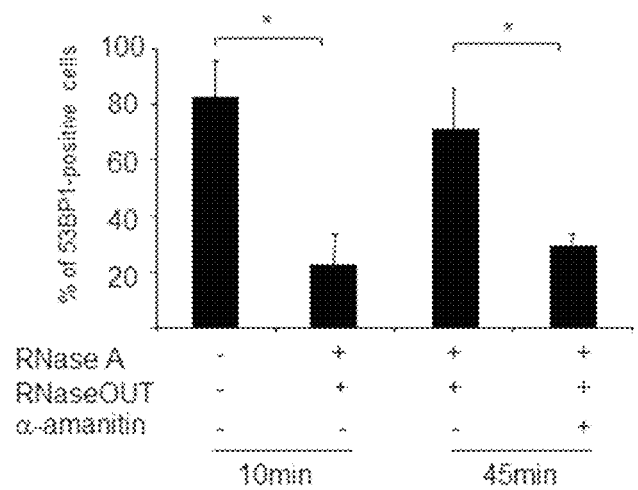

The authors also noticed that when RNase A is inactivated by an RNase A inhibitor (RNaseOUT, a small protein inhibitor), DDR foci progressively reappear within minutes. In addition, the authors also observed that foci reformation can be prevented by the RNA polymerase II-specific inhibitor α-amanitin (FIGS. 23A and 23B). This suggests that that DDR foci formation is dependent on RNA polymerase II RNA products.

Next, the authors tested if DDR foci that are lost after RNase A treatment can reform following the addition of purified RNA to RNase A-treated cells. Therefore, irradiated RNase A-treated cells were washed, incubated with RNaseOUT and α-amanitin and incubated with HeLa-purified total RNA. Strikingly, the authors observed that the addition of total RNA, but not tRNA used as control, robustly restores focal accumulation of all DDR factors tested (FIGS. 4D and 4E) within a relatively short time (15 minutes) at room temperature.

Figure 24A:
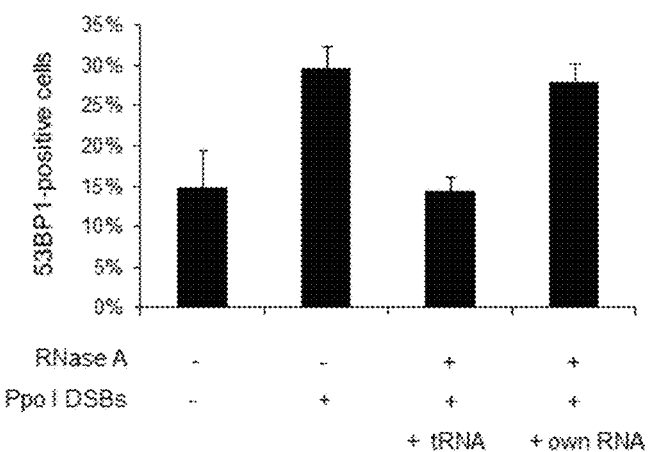
FIGS. 24A-24C|Ppo I-induced DDR foci are RNase A sensitive and reform upon RNA addition. HeLa cells were transfected with the active form of Ppo I, a restriction enzyme, treated with RNase A and incubated with tRNA, as a control, or their own RNA. Histograms show the percentage of cells positive for the indicated DDR markers. Error bars indicate s.e.m. (n=3). Differences (*) are statistically significant (p-value<0.005).
Figure 24B:
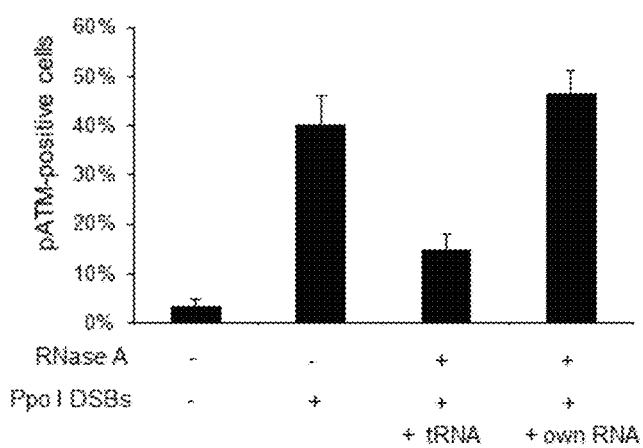
Figure 24C:
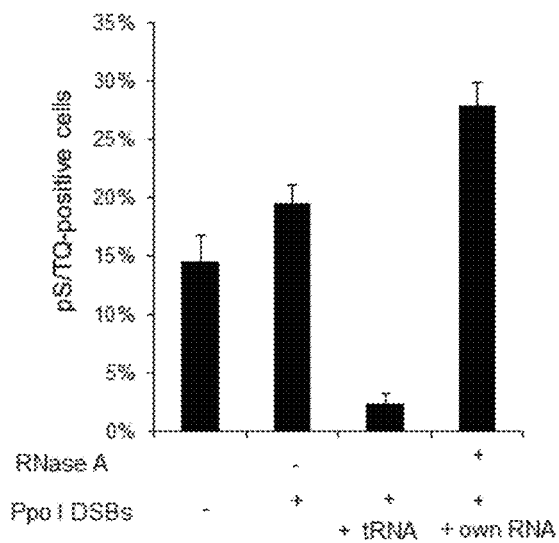

As IR may induce different kinds of DNA lesions, the authors expressed the site-specific endonuclease PpoI[32, 33] which generates several genomic DSBs. Also in this system, the authors could demonstrate that 53BP1, pATM and pS/TQ signals assemble in DDR foci that are sensitive to RNase A treatment and that their reformation can be induced by the addition of RNA extracted from the same cells (FIGS. 24A-24C). Similar conclusions were reached when using an inducible form of the restriction enzyme AsiSI[34] (data not shown).

Figure 4C:
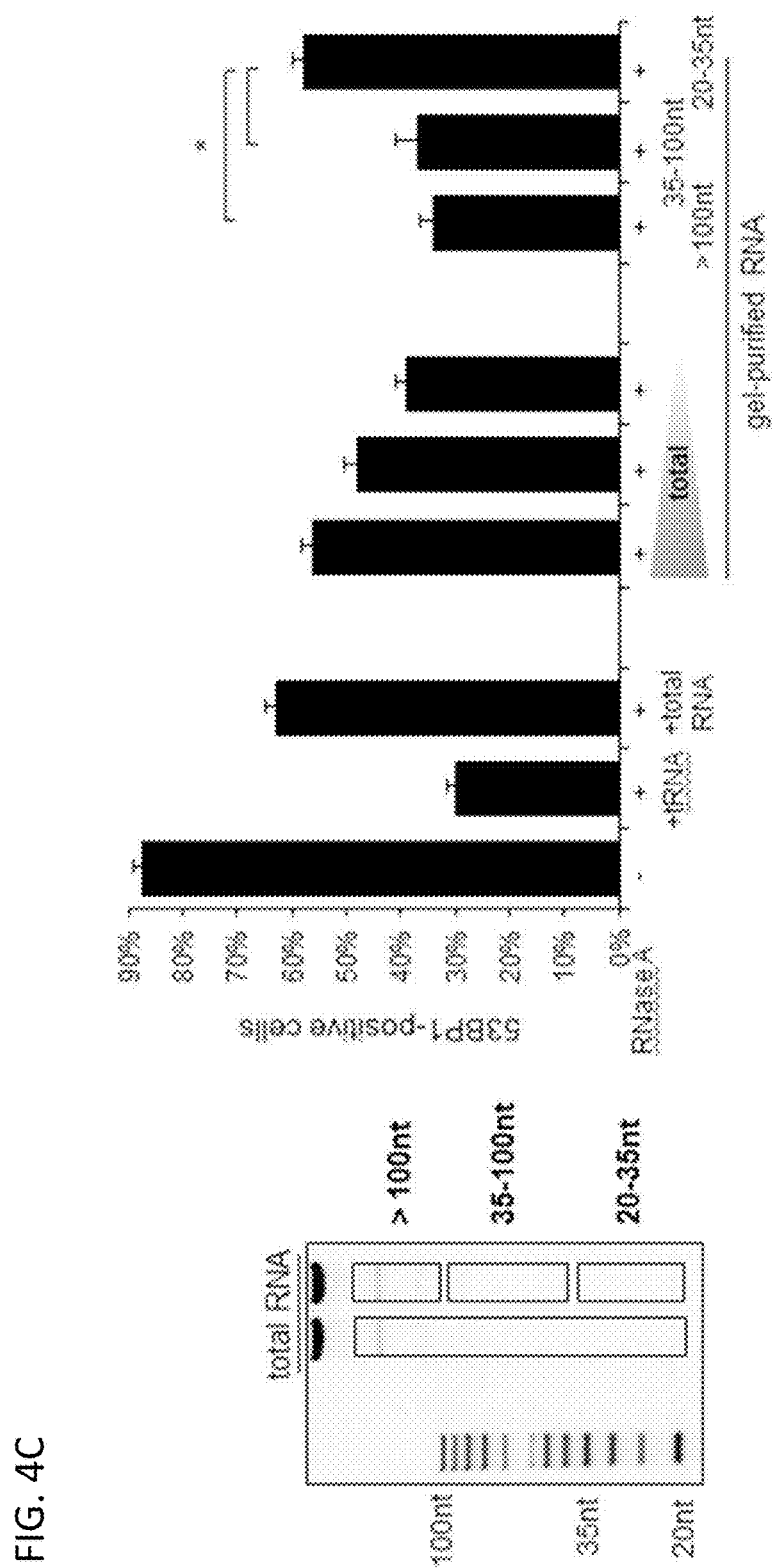

Next, the authors attempted to characterize the RNA species involved in DDR-foci reformation by incubating RNase A-treated cells with different RNA populations. To gauge the length of the RNA molecules involved in DDR focus reformation, the authors enriched total HeLa RNA for short RNAs by chromatography (<200 nt; FIG. 25A) and the authors used proportional volumes of total and short RNA to restore DDR foci in RNase A treated cells. The authors observed that the short RNAs-enriched fraction was sufficient to restore pATM, pS/TQ and 53BP1 foci indicating that this fraction contains the active RNA molecules (FIGS. 25B and 25C) To attain better RNA size separation, the authors resolved total RNA on a polyacrylamide gel and recovered RNAs of different lengths: longer than 100 nt, between 100 nt and 35 nt and between 35 nt and 20 nt (FIGS. 4C, 26A, and 26B). Using equal amounts of RNA from each fraction, the authors observed that only RNAs in the 20-35 nt size range are active in restoring DDR foci formation (FIG. 4C). Thus, two different separation approaches indicate that RNA components required for DDR foci assembly are short and in the size range of the RNA products generated by DICER and DROSHA.

Figure 4D:
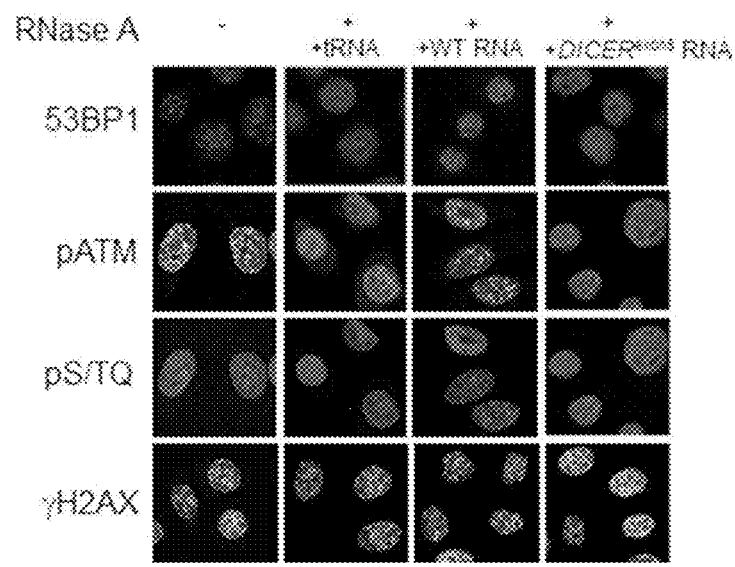
Figure 4E:
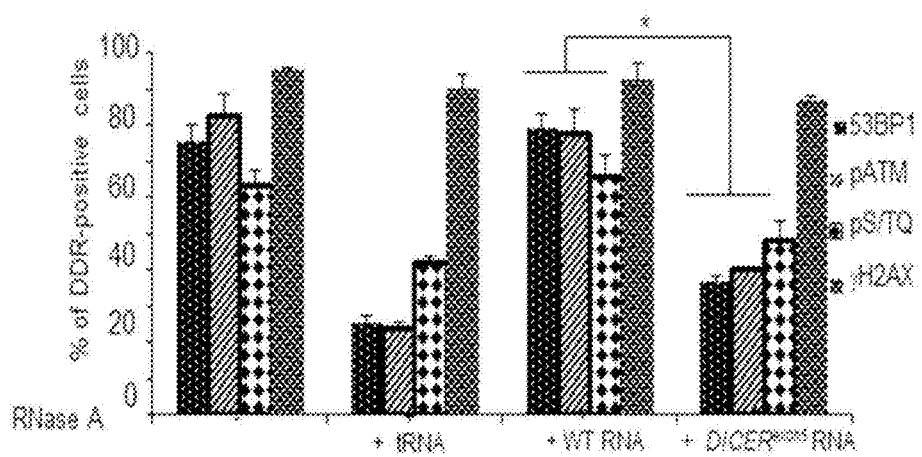
Figure 27A:
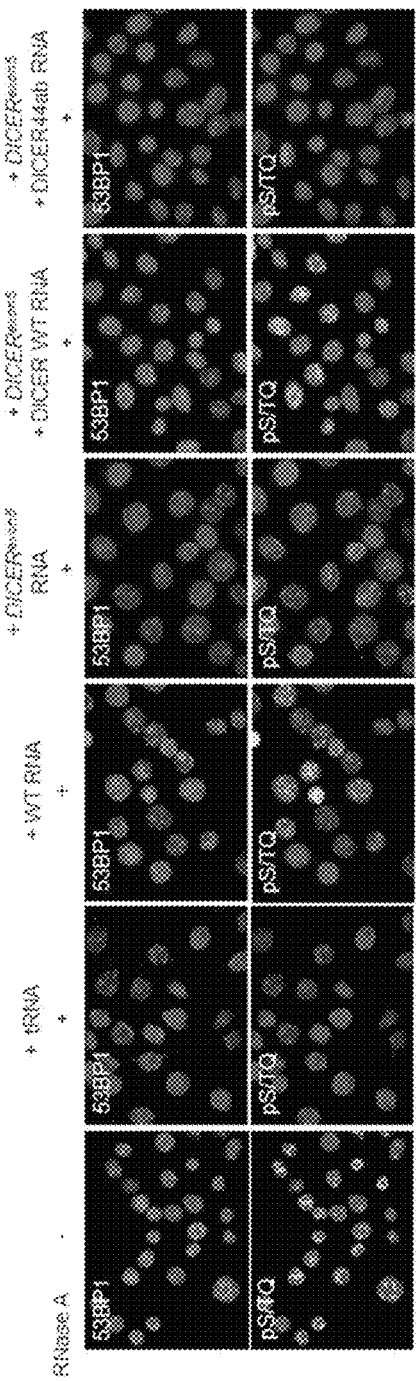
FIGS. 27A and 27B|RNA extracted from DICER$^{exon5}$-hypomorphic cells transfected with wild type but not mutant DICER allows DDR foci reformation in RNase A-treated cells.
Figure 27B:
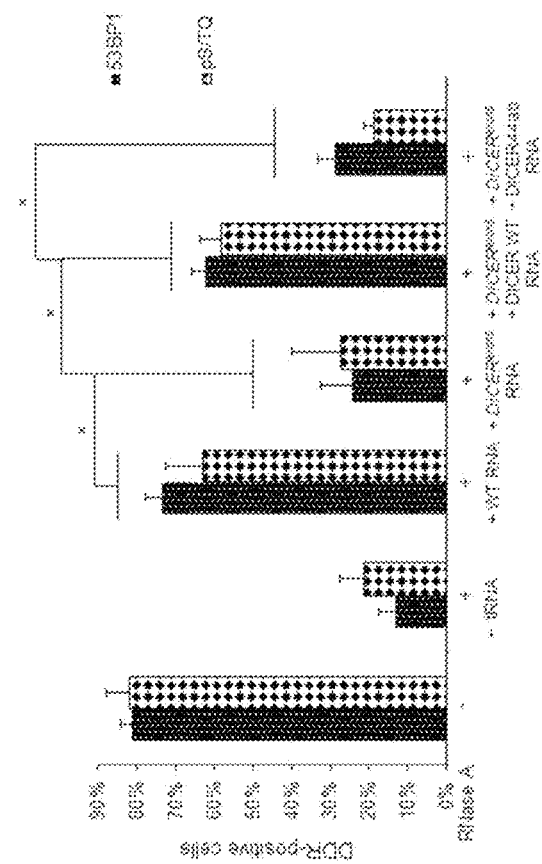

Since the authors observed that inactivation of DICER and DROSHA affects DDR foci formation in living cells and organisms, the authors reasoned that its small RNA products could indeed be responsible for DDR foci restoration in this in vitro cell system. Thus, the authors investigated if DICER RNA products directly contribute to DDR foci formation. To do so, the authors extracted total RNA from wild-type and DICER$^{exon5}$-hypomorphic cells and the authors used these two RNA preparations to restore DDR foci in RNase A-treated irradiated cells. Total RNA preparations from the two cell lines are expected to have the same composition apart from the population of DICER RNA products[25]. Strikingly, while RNA extracted from wild-type cells does restore pATM, pS/TQ or 53BP1 foci, RNA extracted from DICER-$^{exon5}$ hypomorphic cells does not (FIGS. 4D and 4E). Importantly, RNA from DICER$^{exon5}$ hypomorphic cells transfected with a vector expressing wild-type but not mutant DICER allows DDR foci reformation (FIGS. 27A and 27B). These results can be quantitatively reproduced using RNA preparations from two additional cell lines (HCT116 and DLD1) carrying the same hypomorphic DICER mutation[25] (FIG. 28A) and by the use of RNA extracted from cells transiently knocked-down for DICER (FIGS. 28B-28D). To test if also RNA purified from DROSHA-inactivated cells is unable to restore DDR foci, the authors knocked-down DROSHA, and GFP as control, by siRNA in HeLa cells, purified RNA and used these RNA preparations to attempt to restore DDR foci. The authors' experiments revealed that total RNA from siGFP control cells restores DDR foci, while RNA purified from DROSHA-inactivated cells does not (FIG. 28E).

Overall, these observations are consistent with a model in which small RNA molecules generated by DICER and DROSHA are necessary to form IR-induced DDR foci. One conceivable mechanism is that small RNA products from DICER and DROSHA activity suppress the translation of a hypothetical DDR inhibitor. However, the observation that after RNase A treatment (which degrades both mRNAs and microRNAs) (FIGS. 22A and 22B) and α-amanitin treatment (which inhibits transcription), gel-purified 20-35 nt short RNA promote DDR foci reformation, strongly indicates that DICER and DROSHA RNA products control DDR directly and independently from potential mRNA targets and translational modulation. Moreover, the translation inhibitor cyclohexamide has no impact on DDR foci formation in this system (data not shown). These conclusions are consistent with the observation that inactivation of DICER or DROSHA, but not GW-like proteins involved in translational inhibition, impacts on DDR activation in living cells.

DDR Focus Formation at a Defined Damaged Genomic Site Requires Damage Site-Specific RNAs.

Figure 5B:
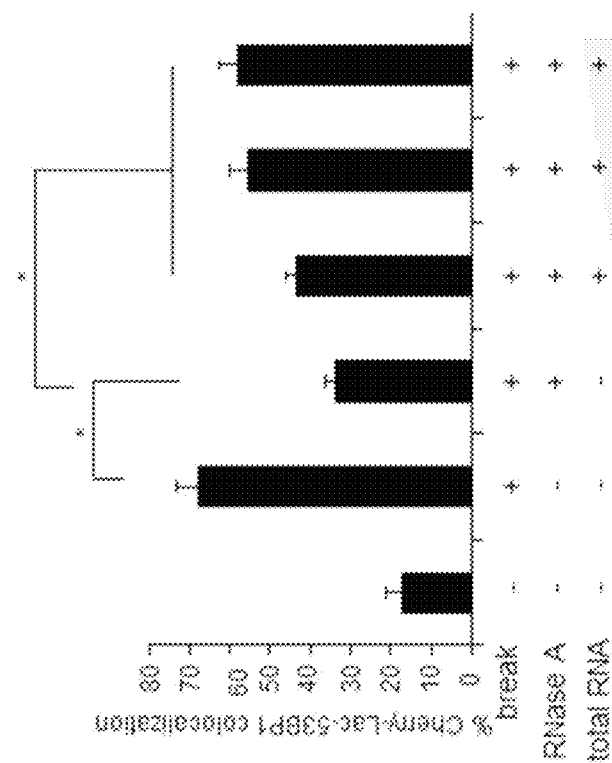
Figure 5A:
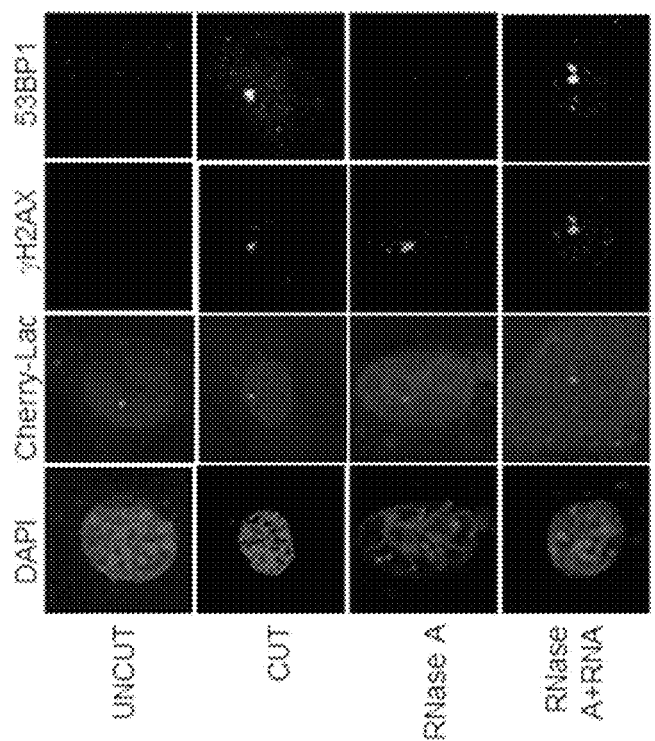

Ionizing radiations induce the formation of DNA lesions that are heterogeneous in nature and random in their location. To reduce this diversity, the authors studied a single DSB at a unique, defined and traceable genomic locus. The authors therefore took advantage of NIH2/4 mouse cells carrying an integrated copy of the I-Sce I restriction site flanked by an array of Lac-repressor (Lac) binding sites and Tet repeats[35]. In this system, the expression of the I-Sce I restriction enzyme together with the fluorescent protein Cherry-Lac-repressor (Cherry-Lac) allows the visualization in the nucleus of the site-specific DSB generated by the nuclease. Indeed, co-expression of I-Sce I and Cherry-Lac-repressor in NIH2/4 cells induces a 53BP1 and γH2AX focus that overlaps with a focal Cherry-Lac signal (FIG. 5A). The authors observed that, also in this system, RNase-A treatment causes the disappearance of the 53BP1 focus from I-Sce I-induced DSB (FIGS. 5A and 5B) and α-amanitin prevents 53BP1 focus reformation at the same site (data not shown). Next, the authors tested if total RNA re-addition, following RNase A treatment, restores DDR focus at the I-Sce I-induced DNA lesion. Therefore, RNase A-treated NIH2/4 cells were incubated with increasing amounts of total RNA extracted from cells treated in parallel. When RNA was added to the RNase A-treated samples, NIH2/4 cells re-acquired a bright 53BP1 focus co-localizing with the Cherry-Lac-repressor in a manner dependent on the RNA amount used (FIGS. 5A and 5B). Therefore, the very same DDR focus generated on a defined DSB can disassemble and reassemble in a manner dependent on RNA.

Collectively, the results described so far demonstrate that DICER and DROSHA short RNA products control DDR foci formation. However, as such, they do not allow to discriminate whether RNAs are generated in cis using the damaged genomic locus as a template or in trans from a distinct locus. To discriminate between these two possibilities, the authors took advantage of the fact that the I-Sce I-induced DSB is generated within an exogenous sequence, which is not present in the parental cell line. The authors therefore transfected I-Sce I and the Cherry-Lac-repressor in NIH2/4 cells and in the NIH3T3 parental cell line and the authors used RNA extracted from either cell lines to attempt to restore 53BP1 focus formation in RNase A-treated NIH2/4 cells that had experienced the I-Sce I-induced DSB: the two RNA preparations are expected to differ only in the potential presence of RNA transcripts generated from the exogenous integrated construct carrying the Lac and Tet repeats and the I-Sce I site. Excitingly, the 53BP1 focus assembly on the I-Sce I-induced DSB, as labeled by Cherry-Lac-repressor, was efficiently recovered only by the addition of RNA purified from NIH2/4 cells and not by RNA extracted from the NIH3T3 parental cell line (FIG. 5C). This result indicates that DDR-focus formation requires an RNA component, which originates from the damaged genomic locus.

The MRE11/RAD50/NBS1 (MRN) complex is a key DNA damage sensor and a necessary cofactor of the apical DDR regulator ATM[1]. Also MRE11 focus formation upon I-Sce I induction is sensitive to RNase A-treatment (FIG. 29A). To probe the molecular mechanisms of action of RNAs at sites of DNA damage, the authors used mirin, a specific small molecule inhibitor of MRN[36] which, as expected, prevents ATM activation also following I-Sce I induction (FIG. 29B). The authors therefore tested whether RNAs involved in DDR modulation engage MRN. The authors observed that in the presence of mirin, NIH2/4 RNA is unable to induce 53BP1 or pATM focus reformation (FIGS. 5D and 5E). This result demonstrates that RNAs at sites of DNA damage modulate DDR in a MRN-dependent manner.

To detect potential short RNAs originating from the integrated locus, the authors isolated nuclear RNA from parental NIH 3T3 cells transfected with the I-Sce I (mock), NIH 2/4 cells transfected with Cherry-Lac-repressor (uncut) and from NIH 2/4 cells transfected with the I-Sce I (cut) and further selected them for length (<200 nt)—this procedure enriches for RNAs active in DDR foci reformation 40 folds (data not shown). Libraries prepared from these samples were sequenced by Illumina GAII-X to obtain 15-32 bp cDNA reads (FIGS. 30A-30D). Their analyses revealed transcripts arising from the exogenous locus which were absent in the parental NIH 3T3 cells which had a length distribution of mapped tags peaking around 22 nt, the length of canonical miRNAs (FIG. 29E). Thus, even an exogenous integrated locus lacking mammalian transcriptional regulatory elements is transcribed and generates short RNA transcripts.

Figures 6A, 6B, 6C, 6D:
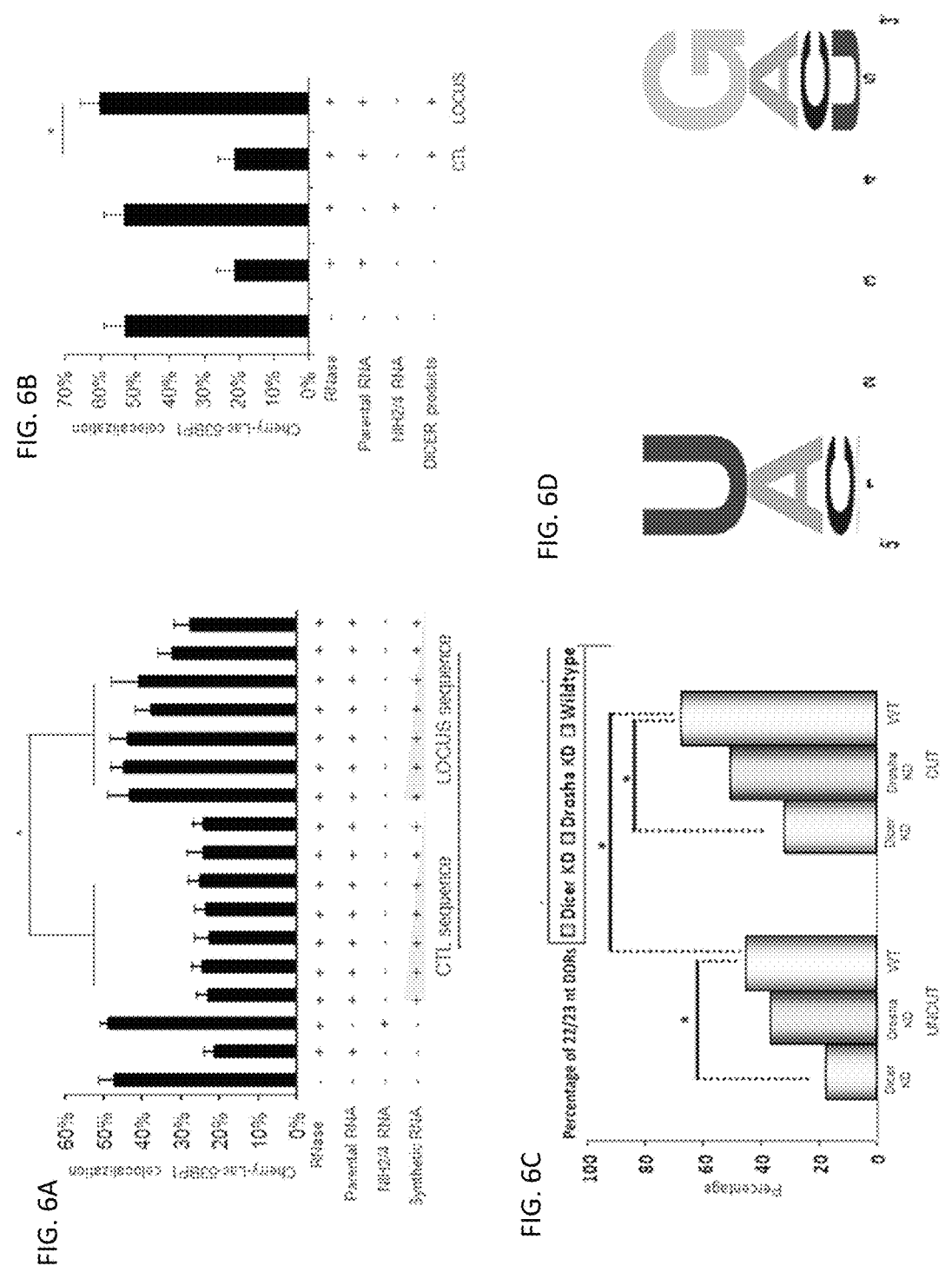

In order to test whether the short RNAs identified at the damaged locus are biologically active in DDR activation, the authors chemically synthesized four potential pairs of short RNAs as identified at the cut genomic locus by short RNA sequencing as described above and the authors used them to attempt DDR focus reformation in RNase A-treated cells carrying a DSB at the locus. By testing them over a large range of concentrations, the authors could demonstrate that the addition of these RNAs, but not equal amounts of control ones, promote site-specific DDR activation at the damaged site (FIG. 6A). These chemically-synthesized short RNAs are biologically active both when added to the cells together with total RNA from parental cells (cells not carrying the integrated endogenous locus; FIG. 6A) or with yeast tRNA (FIG. 30F), thus in the absence of any additional mammalian RNA.

Figure 30A:
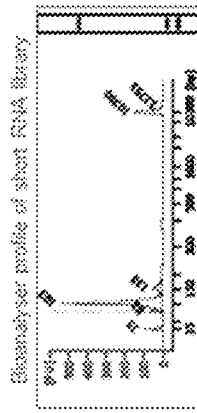
FIGS. 30A-30H|Identification of biologically active locus-specific molecules. Chemically synthesized locus-specific RNAs and in vitro generated DICER RNA products promote DDR focus formation at the DNA damage site in RNase A-treated cells.
Figure 30B:
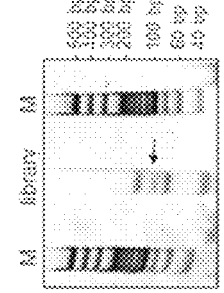
Figure 30C:
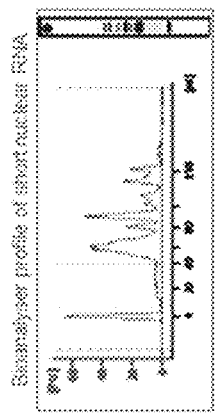
Figure 30D:
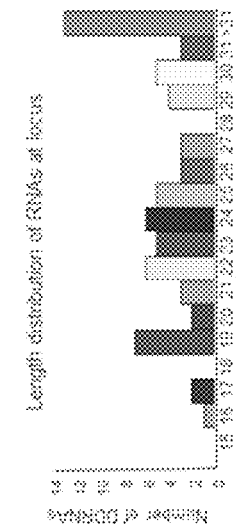
Figure 30E:
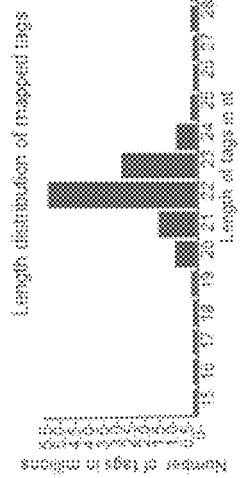
Figure 30F:
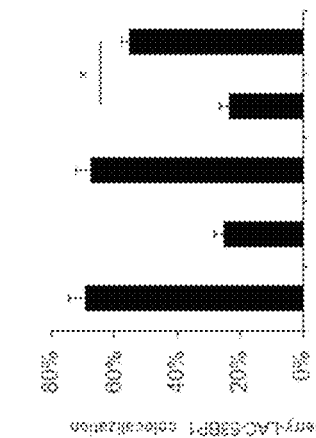
Figure 30G:
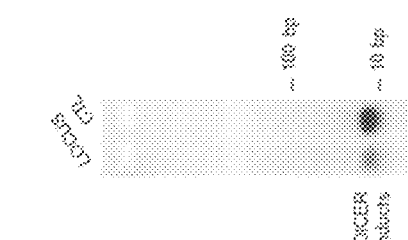
Figure 30H:
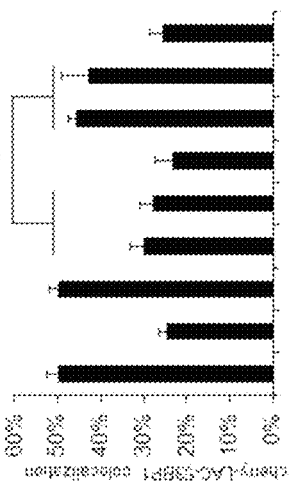
Figure 31A:
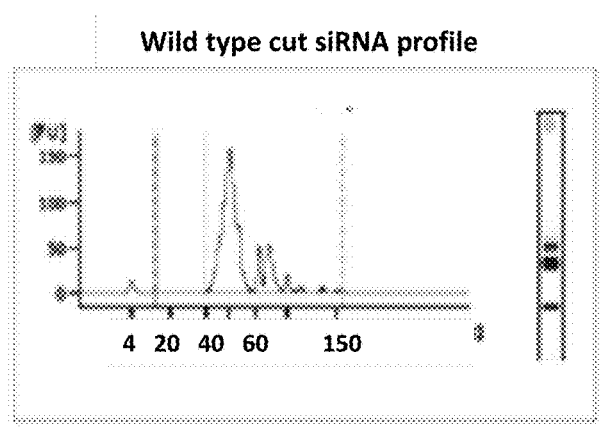
FIGS. 31A-31I|Library profile and length distribution of selected sequenced samples.
Figure 31B:
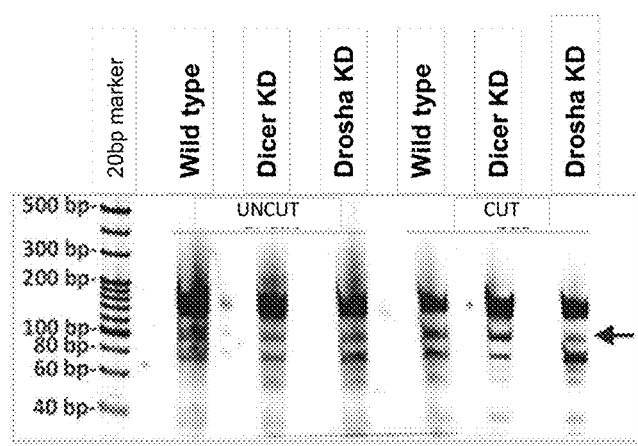
Figure 31C:
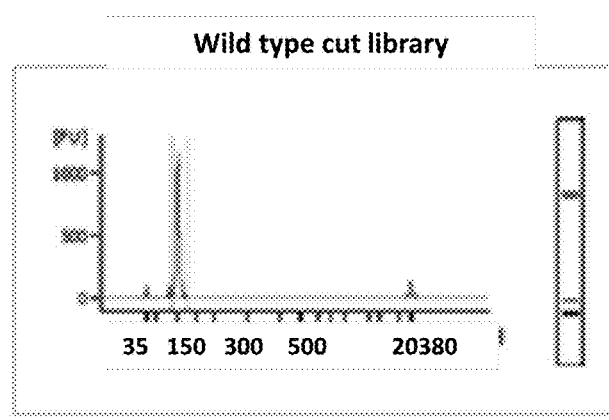
Figure 31D:
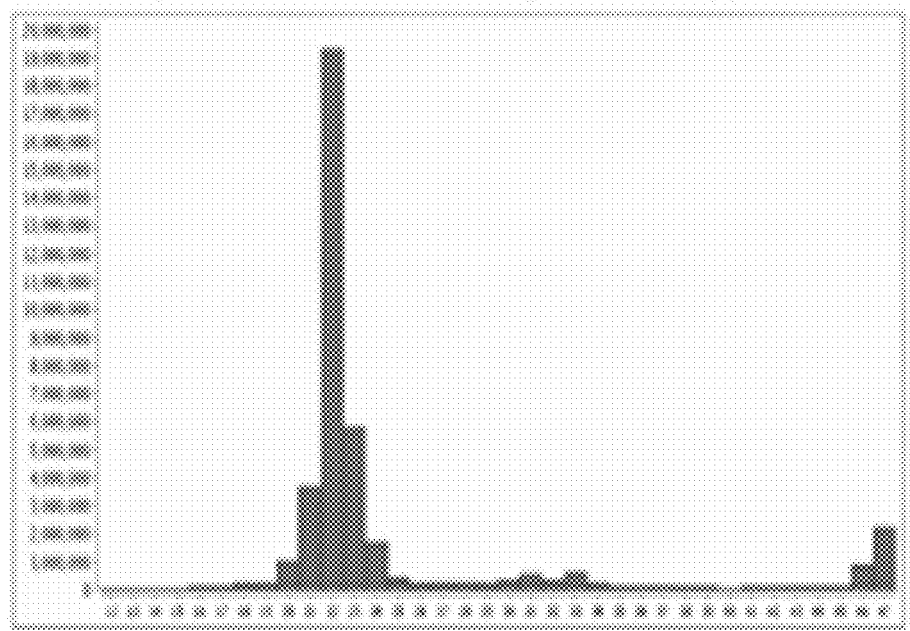
Figure 31E:
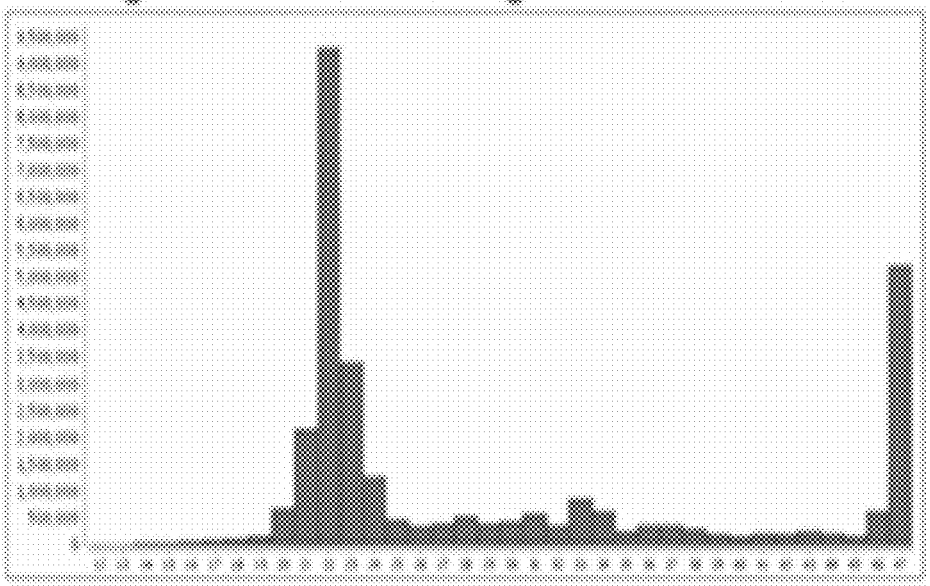
Figure 31F:
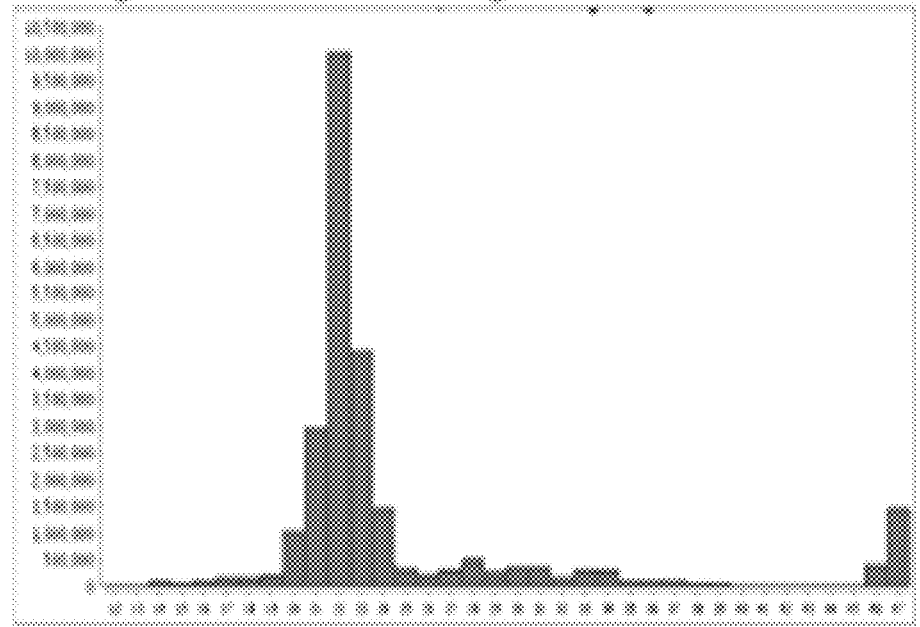
Figure 31G:
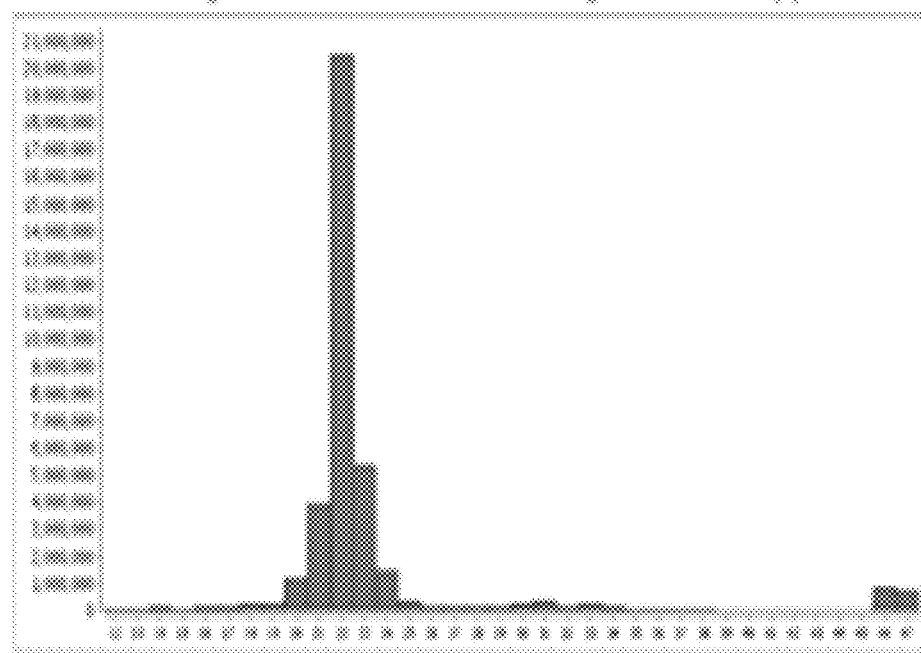
Figure 31H:
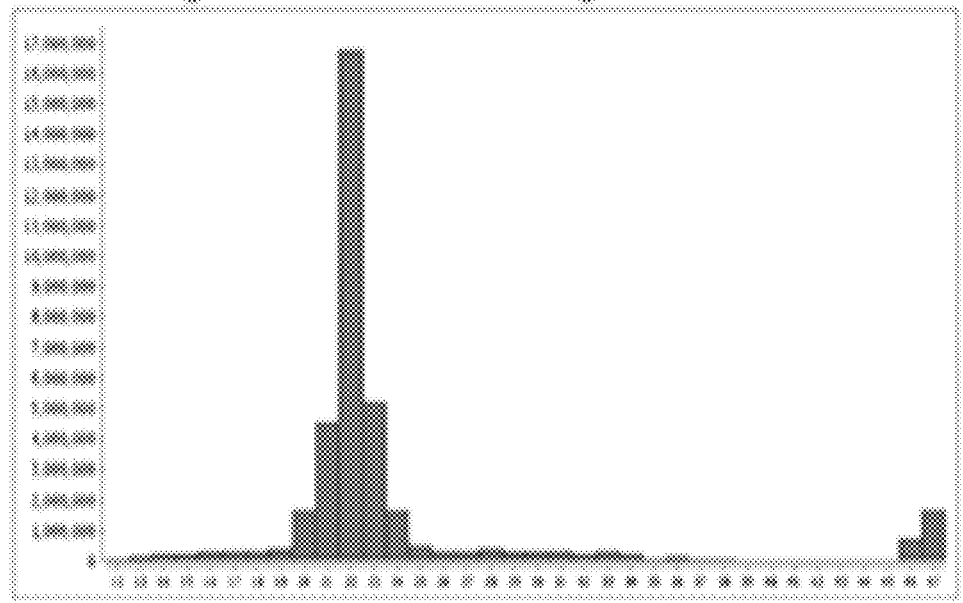
Figure 31I:
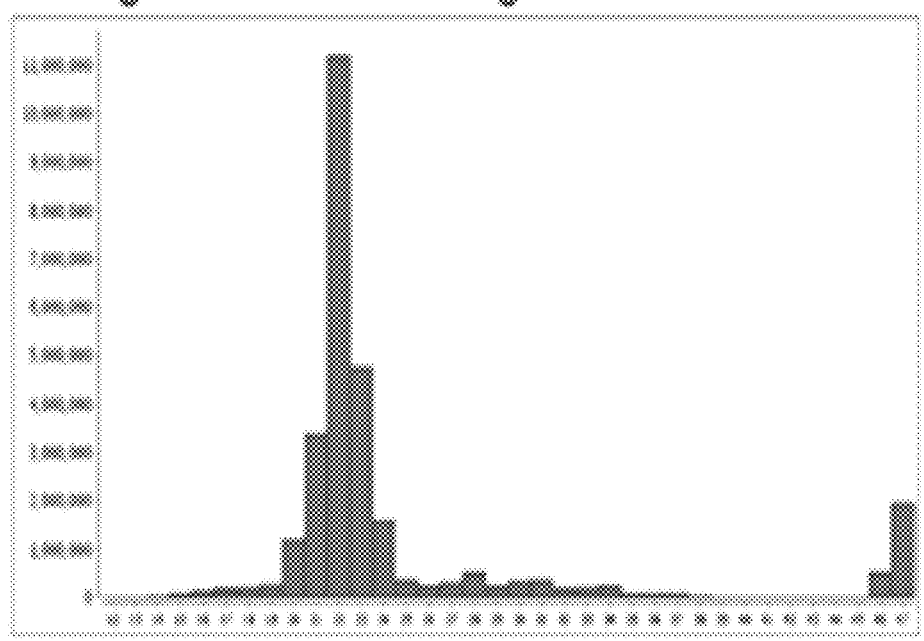

In addition, to prove the biological activity of locally generated DICER RNA products, the authors cloned the locus, and an unrelated control DNA, in a plasmid to allow its transcription in vitro by T7 polymerase and the authors processed the resulting RNAs with recombinant DICER protein in vitro. The resulting short RNAs (FIG. 30G) were purified and tested in RNase A-treated cells. The authors observed that also these locus-specific DICER-generated RNAs, but not equal amounts of control RNAs, allow DDR focus reformation both when mixed with RNA from parental cells (FIG. 6B) and when mixed with yeast tRNA (FIG. 30H). Thus, in vitro generated DICER RNA products promote DDR focus reformation at the DNA damaged site in a sequence-specific manner.

Overall, these results indicate that short RNAs with the sequence of the damaged locus play a direct role in DDR activation at the damaged site.

Figure 32A:
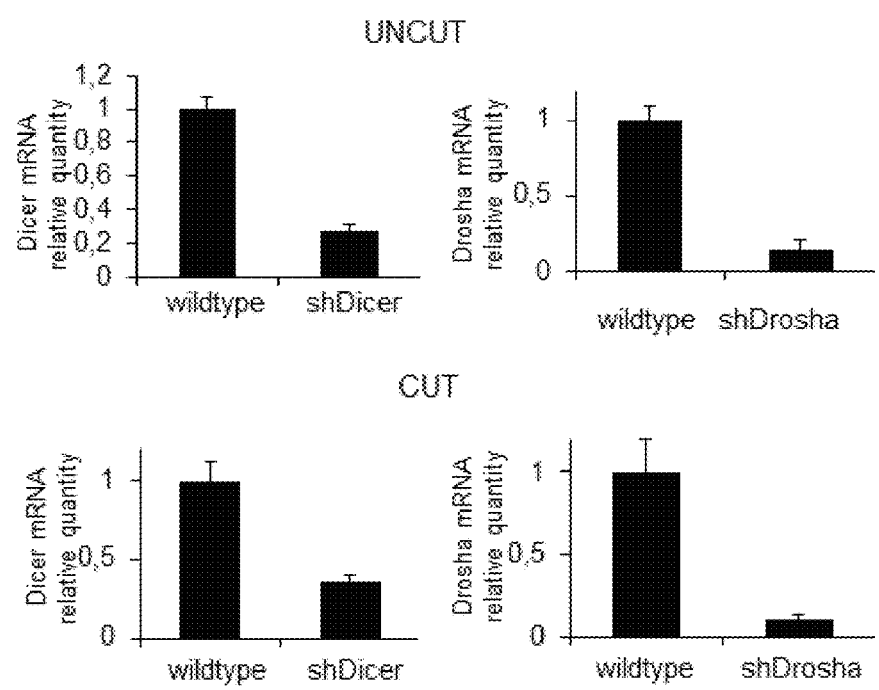
FIGS. 32A and 32B|Dicer and Drosha knockdown down-regulates miRNAs.
Figure 32B:
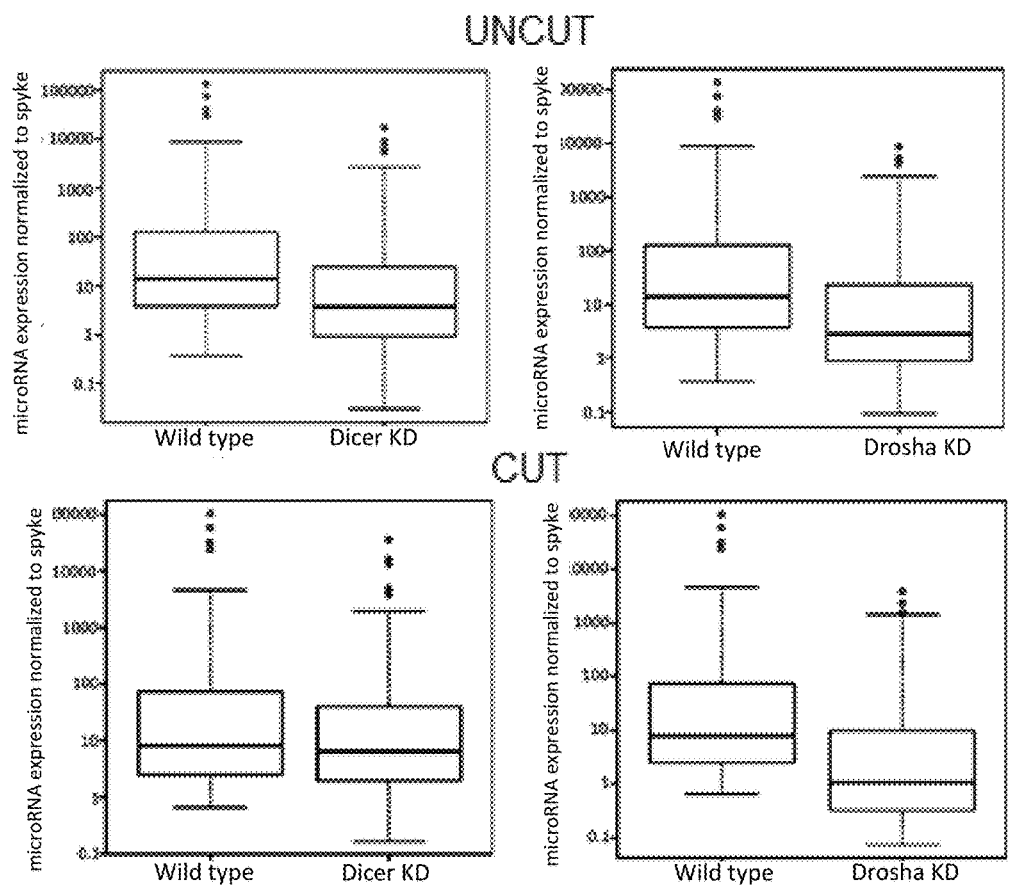

In order to further investigate the nature of the RNAs generated at the locus, the authors performed deeper sequencing experiments of nuclear RNAs<200 nt from wildtype NIH 2/4 samples before and after cut using the Illumina Hi seq Version3 (FIGS. 31A-31I). To study the biogenesis of these RNAs, the authors also sequenced <200 nt nuclear RNAs from NIH 2/4 cells following Dicer or Drosha knockdown (WT uncut, Dicer KD uncut, Drosha KD uncut, WT cut, Dicer KD cut, Drosha KD cut) (FIG. 32A). To ease normalization, each RNA preparation was spiked with a short RNA "spike" before library preparation. Reads were mapped to miRBase 18 and, after spike normalization, were demonstrated to be significantly reduced after Dicer or Drosha knockdown in uncut and cut samples when compared with wildtype uncut and cut samples respectively (FIG. 32B). This validates the functional efficacy of the knockdowns performed.

Figure 33A:
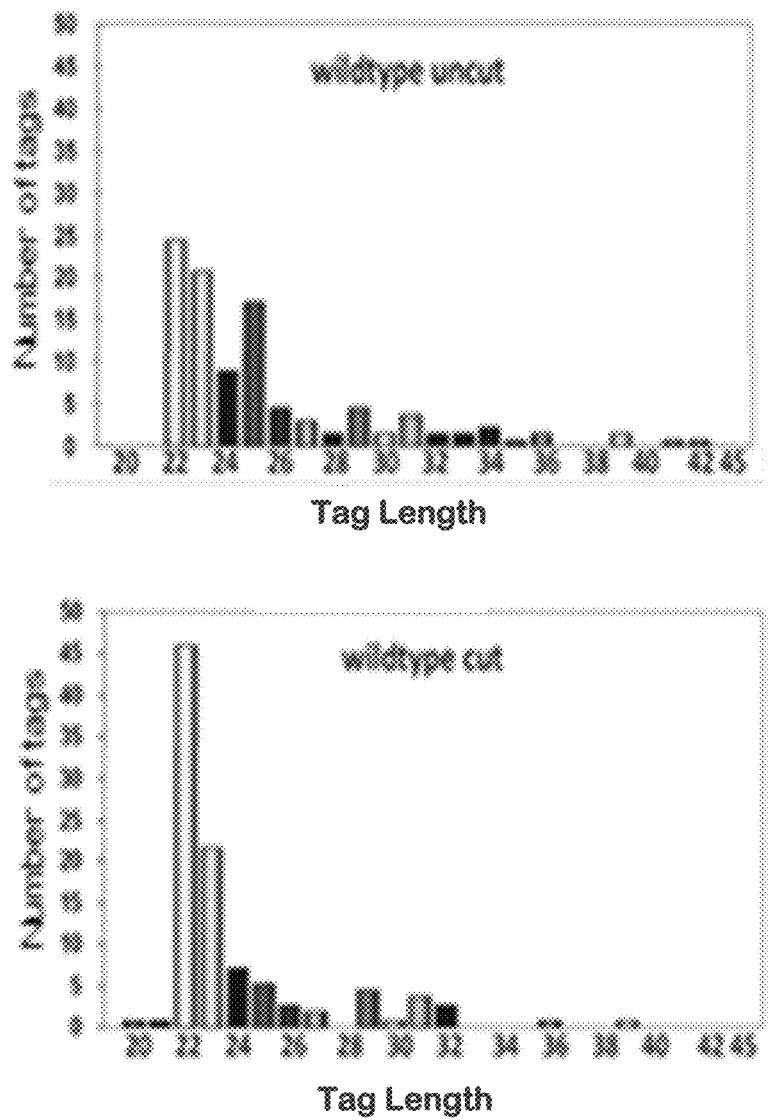
FIGS. 33A-33D|Features of short RNAs arising from the locus. Length of tags arising from the locus before and after cut. Y-axis shows number of tags from the locus and X-axis depicts tag lengths in nucleotides. The bulk of short RNAs in wildtype samples before and after cut are in the 22-23 nt size range. Among knockdown samples, Dicer knockdown shows a broader tag length distribution.

By analyzing the locus, the authors found that in wildtype samples the bulk of RNAs from the locus were in the 22-23 nt size range (45.2% in WT uncut and 67.6% in the wildtype cut, FIGS. 6C and 33A). Fitting a negative binomial model to the sequence count data and application of the likelihood ratio test showed that this increase in the fraction of 22-23 nt vs total short RNAs in wildtype cut sample is statistically significant respect to the uncut sample (p=0.020) (FIG. 6C). Further, the authors found that the fraction of 22-23 nt vs total short RNAs at the locus decreases upon Dicer knockdown, both in the uncut (p=4.8e-7) and cut (p=0.029) conditions, suggesting that the 22-23 nt RNAs at the locus are indeed Dicer dependent (FIG. 6C). The fraction of 22-23 nt vs total short RNAs at the locus also decreases upon Drosha knockdown.

Figure 33B:
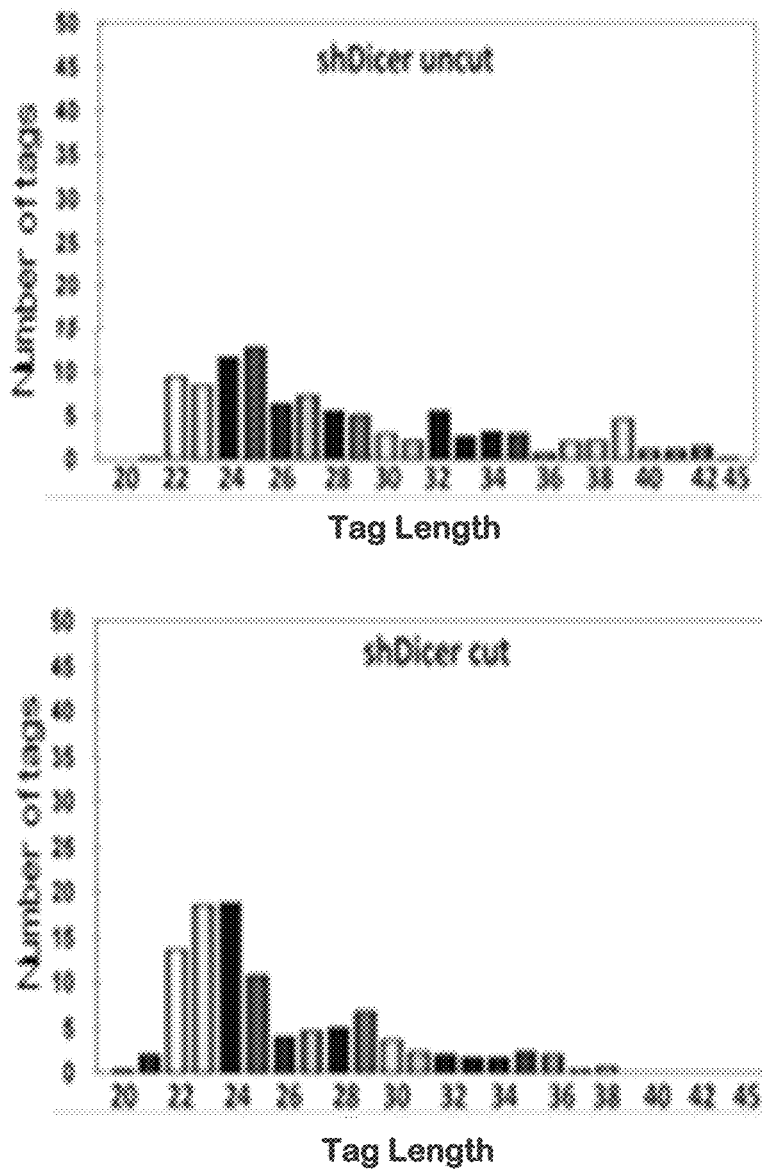
Figure 33C:
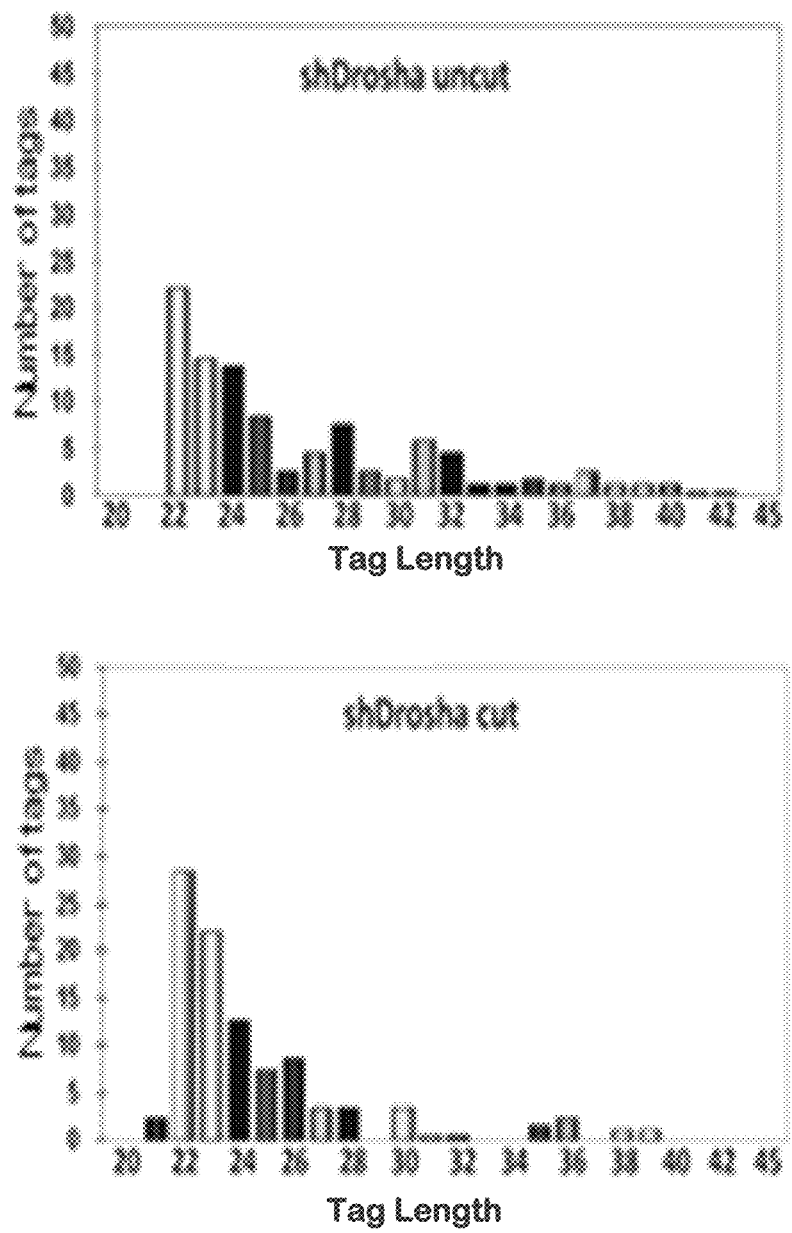
Figure 33D:
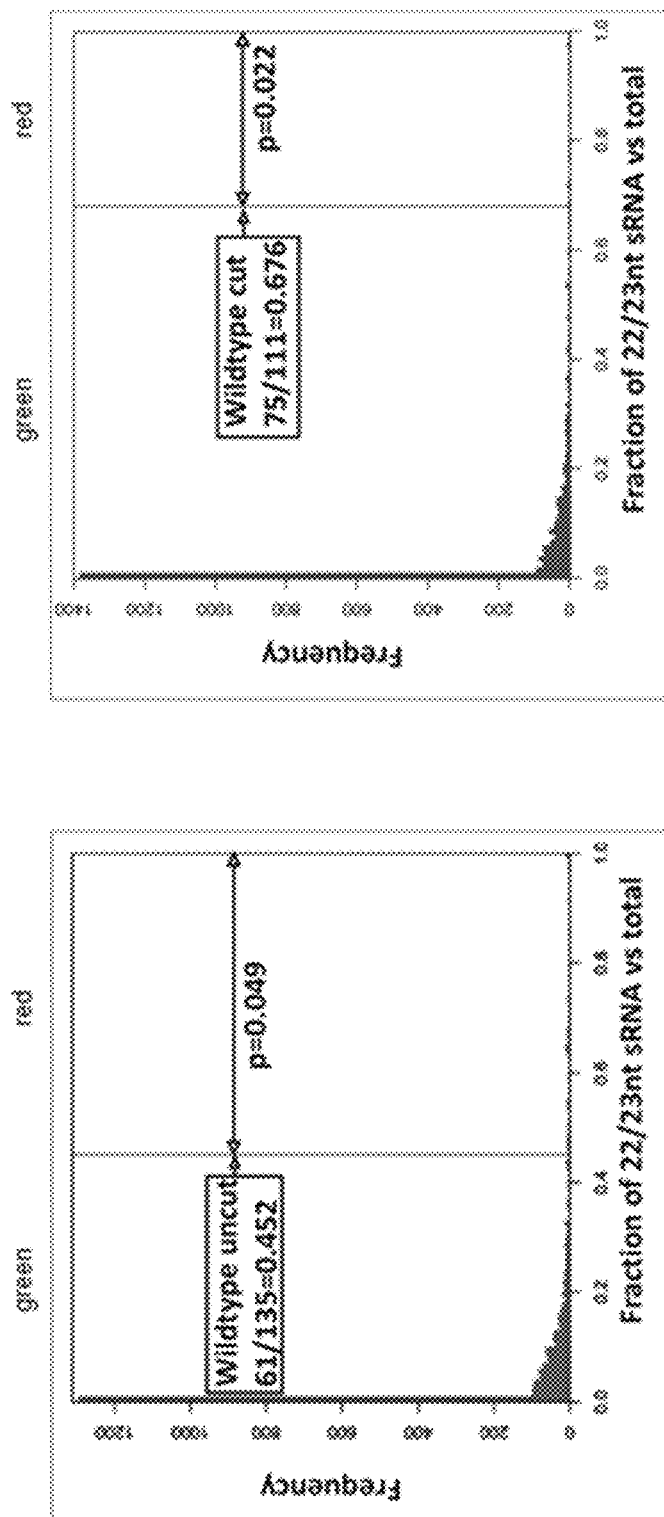

To further exclude that the majority of tags arising from the locus were products of random degradation, the authors compared the fraction of 22-23 nt vs total RNAs at the locus to the same fraction at non-miRNA genomic loci—at such loci, any 22-23 nt RNAs are most likely products of random degradation or Dicer/Drosha independent enzymatic processing. The authors found that the fraction of 22-23 nt vs total short RNAs is significantly larger than the fraction found in non-miRNA genomic loci before cut (p=0.049) and after cut (p=0.022, FIG. 33B).

Finally, the authors observed that the distribution of nucleotides at the 5' and the 3' end of RNA sequences from the locus is significantly different from both the genomic background nucleotide distribution (p=0.012 at the 5' end and 0.008 at the 3' end) as well as the background nucleotide distribution at the locus (p=0.014 at the 5' end and 1.2e-6 at the 3' end). Specifically, 82.9% sequences start with an A/U and 48.6% sequences end with a G (FIG. 6D).

By these analyses the authors therefore conclude that 22-23 nt RNAs are the bulk of the RNA species detected at the locus, they depend on Dicer and, to an extent, on Drosha, and their proportion increases upon DNA damage. Their unlikelihood to be random degradation products is further indicated by their differential abundance compared to the rest of non-miRNA loci and the observed 5' and 3' base bias.

Sequence-Specific Inhibitory Oligonuncleotides (LNAs) Reduce DDR Activation at a Specific Genetic Locus.

The authors previously showed that DDRNAs identified by deep sequencing are biologically active and have a causative role in sequence-specific DDR focus reformation at the damaged site, following removal of all cellular RNAs by RNaseA treatment (FIG. 6a; FIG. 30f).

The authors next aimed to test whether DDRNA functions could be inactivated in living cells by sequence-specific Locked Nucleic Acids (LNA, modified DNA oligonucleotides avidly binding and inactivating complementary RNA species) (Jepsen et al., Oligonucleotides, 2004; Machlin et al., Curr Gene Ther., 2012).

The authors thus got 4 LNA molecules synthesized (Exiqon) with their sequence fully complementary to the individual DDRNAs they previously showed to be biologically active and able to restore DDR signaling and focus formation in RNaseA-treated cells (FIG. 6a; FIG. 30f). Given the repetitive DNA sequence structure of the locus, these are likely to anneal also to other DDRNAs generated at the locus (FIG. 34a).

Figure 34C:
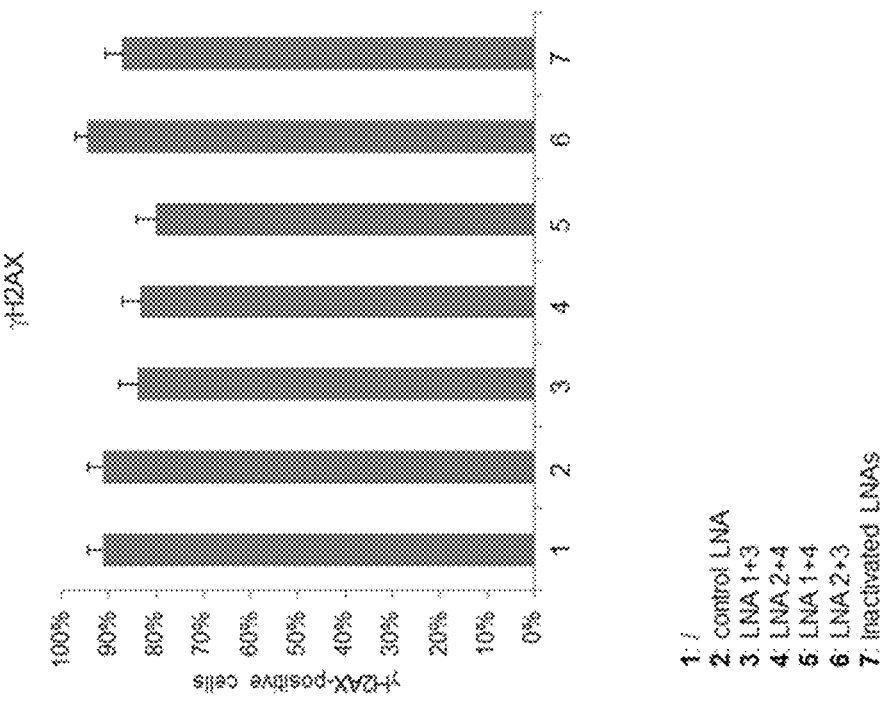

Cells carrying the integrated locus were co-transfected with Cherry-Lac and I-Sce I-restriction endonuclease-expressing vectors and with either no LNA (sample 1), control LNA carrying an unrelated sequence which is not part of the locus (sample 2) or different sets of LNA (samples 3-7) (FIG. 34b). 24 hours post transfection, cells were fixed and stained for DDR markers. The authors analyzed the samples at the confocal microscope and scored as positive those cells that showed a DDR signal at the locus. As shown in FIG. 34B, the portion of cells showing a specific γH2AX focus co-localizing with the Cherry-Lac signal was not significantly affected by the transfection of any LNA. This is consistent with the authors' data showing that any impairment of the biogenesis of DDRNAs or removal of RNAs by RNaseA treatment makes no significant impact on γH2AX (FIG. 1; FIGS. 4A, 4B, 4D, and 4E; FIG. 5A). Differently, 53BP1 accumulation at the locus, a marker of activated DDR, is significantly reduced upon transfection of LNA with the sequence matching the DDRNAs (samples 3-6), compared to control LNA (sample 2) or to the same LNA inactivated (sample 7; FIG. 34C). LNA were inactivated by annealing them to each other in vitro before transfection, thus becoming unable to bind and interfere with the action of other complementary nucleic acids. The decrease in 53BP1 accumulation was observed, to different extents, for all LNA sets tested (samples 3-6). In summary, these results demonstrate that sequence-specific LNAs can specifically inactivate the known biological functions of DDRNAs.

Sequence-Specific Inhibitory Oligonucleotides (i.e. LNAs) with a Telomeric Sequence Reduce DDR Activation at Dysfunctional Telomeres.

The authors previously showed that short RNAs with the sequence of a damaged locus (named DDRNAs) are necessary for DDR activation and maintenance specifically at that locus, upon ionizing radiations or endonuclease cleavage (FIGS. 4,5). However, nothing is known about the role of DDRNAs at telomeres. Telomeres are the end of linear chromosomes, and they are protected by a protein complex named shelterin (de Lange, Genes Dev. 2005). Removal of this protection causes telomere uncapping, so telomeres are recognized as DNA DSBs. This may lead to DDR activation, cellular senescence, chromosomal fusions and genome instability (Sfeir and de Lange, Science 2012).

In order to investigate the role of DDRNA at dysfunctional telomeres, the authors used CRE-ER TRF2$^{flox/flox}$ mouse embryonic fibroblasts (MEFs) (Lazzerini Denchi and de Lange, Nature 2007). Cells were grown in presence of 4-hydroxytamoxifen to induce cre recombinase localization into the nucleus, thus generating a TRF2-knockout (TRF2$^{-/-}$) cell line. TRF2 is one of the shelterin component and its removal induces a strong DDR activation at telomeres (Lazzerini Denchi and de Lange, Nature 2007). To test the role of DDRNA at the telomeres, we treated MEFs TRF2$^{-/-}$ with RNase A or BSA as a control. Consistent with the authors' previous results, they observed that γH2AX foci resist, while 53BP1 foci are sensitive to RNase A treatment (FIG. 35a-b). This suggests that, like all other DSB lesions, also at uncapped telomeres, DDRNAs with telomeric sequence are generated and they are necessary for DDR cascade activation.

Figure 36A:
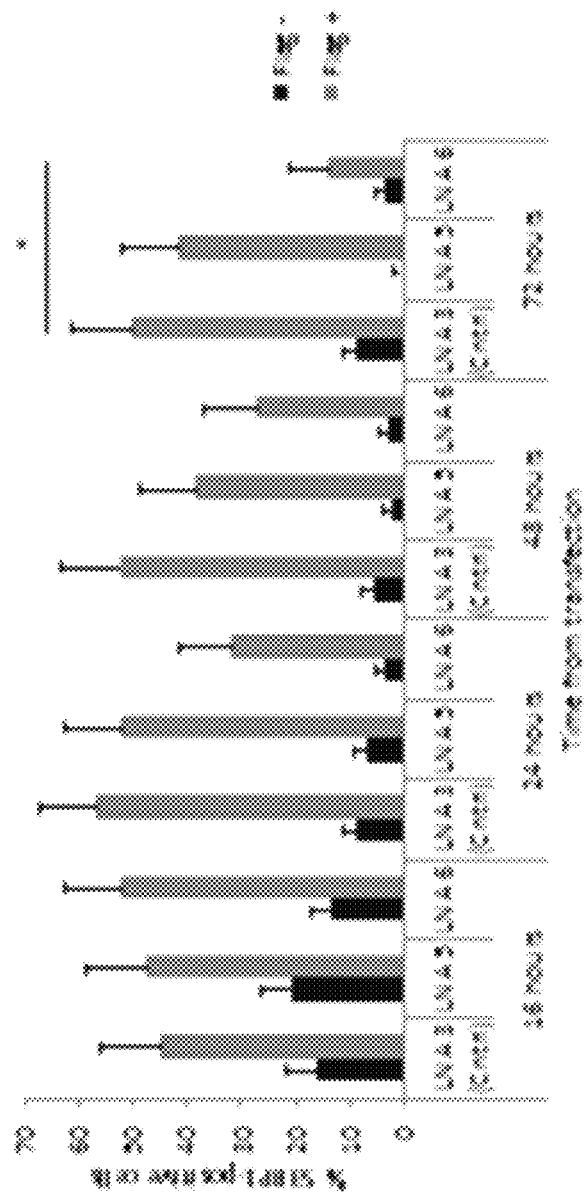
FIGS. 36A-36C|Sequence-specific inhibitory oligonucleotides (i.e. LNAs) transfection suppresses DDR and prevents BrdU reduction following telomere-uncapping. T19 fibrosarcoma cell line (van Steensel, Cell 1998) was cultured in absence of doxycycline to induce expression of a dominant negative allele of TRF2 fused to flag. Induced cells are visualized by Flag immunostaining. Induced (Flag+) and uninduced (Flag−) cells were transfected with LNA molecules (200 nM) matching the sense (LNA 6), the antisense (LNA 5) telomeric sequence, and an unrelated (LNA 3, Cntrl) sequence at day 13 from induction.
Figure 36C:
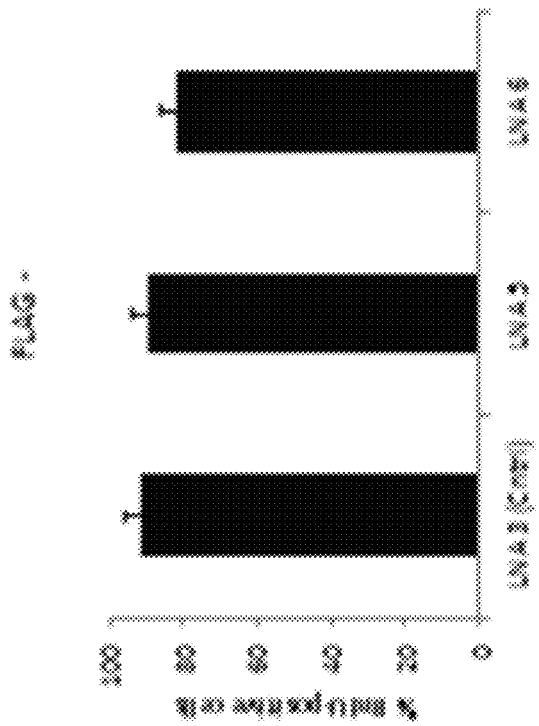
Figure 36B:
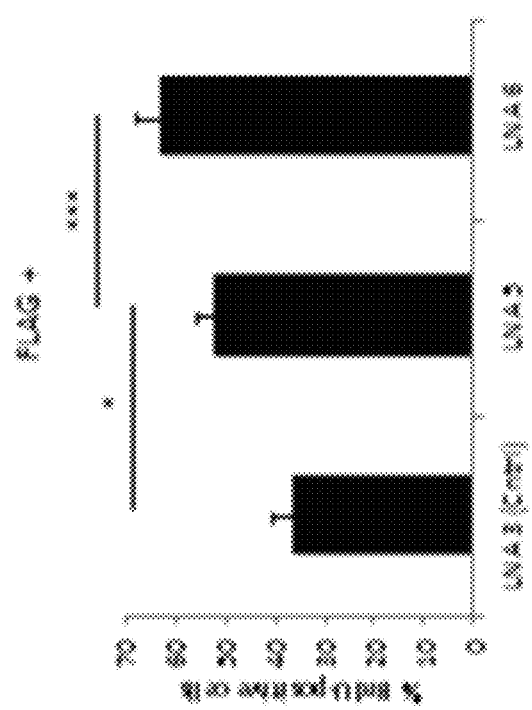

Cells can accumulate damaged telomeres during ageing, due to telomeric shortening (Harley, Nature 1990; Herbig, Mol Cell 2004; d'Adda di Fagagna, Nature 2003) or to endogenous or exogenous DNA damage occurred at telomeres. DNA damage accumulate and DDR signaling persists at telomeres as they are not repairable (Fumagalli, Nat Cell Biol 2012). In both cases this persistent DDR activation at telomeres leads to cellular senescence. If DDRNAs are necessary for DDR at damaged telomeres, inhibiting their action could suppress DDR activation and potentially prevent or revert the senescence phenotype. To test this hypothesis, the authors used a human cell line, T19 fibrosarcoma cells, that express an inducible dominant negative (DN) allele of flag-tagged TRF2 (van Steensel, Cell 1998). The expression of this allele is induced culturing cells in the absence of doxycycline. After 7-8 days of DN TRF2 expression, telomeres are dysfunctional and cells show a strong DDR activation at telomeres (data not shown and van Steensel, Cell 1998). Induced cells, in which Flag-DN TRF2 was expressed, are positive for Flag immunostaining (Flag+). At day 13 from induction, the authors transfected T19 cells with LNA molecules with sequences complementary to either strands of telomeric DNA repeats (LNA 5 and 6) or an unrelated sequence as control (LNA 3, Cntrl). The authors observed that, with time, in Flag+ cells, both LNAs transfected individually with telomeric sequence decrease the percentage of 53BP1-positive cells, to a different extent, while control LNA had no effect (FIG. 36a). Importantly, in uninduced undamaged cells (Flag−), LNA molecules are not inducing any DNA damage, excluding that they can be genotoxic per se. Furthermore, the authors monitored the passage through S phase of cell cycle, looking at BrdU incorporation in induced T19 cells, three days after LNA transfection. The authors observed that Flag+ cells, transfected with telomeric LNAs, proliferate significantly more than control cells (FIG. 36b), suggesting that LNA, by inactivating DDR at telomeres, can promote cell cycle reentry of cells otherwise activating a DNA-damage checkpoint and reducing BrdU incorporation. In contrast there is no significant difference in Flag− cells (FIG. 36c).

Here the authors show that different sources of DNA damage, including oncogenic stress, ionizing irradiation and PpoI or I-Sce I endonucleases engage the DDR in a manner dependent on DICER and DROSHA RNA products. These DDR-regulating RNAs (DDRNAs) control DDR-foci formation and maintenance, checkpoint enforcement and cellular senescence. This occurs both in cultured human and mouse cells and in different cell types in living zebrafish embryos.

Oncogene activation can trigger DDR and DDR-induced cellular senescence acts as tumor suppressive mechanism[2,37]. DICER inactivation enhances tumor development in a K-Ras-induced mouse model of lung cancer[38,39] and inactivation of various components of DICER and DROSHA complexes stimulate cell transformation and tumorigenesis[38]. More recently, mutations of DICER and TARBP2, a DICER cofactor affecting its stability, have been described in human carcinomas[40,41]. However, individual microRNAs have been reported both to promote and to reduce cell proliferation by regulating stability and translation of mRNAs encoding proteins with different roles in cell proliferation[18]: it is therefore presently unclear how RNAi apparatus inactivation favors tumorigenesis. In the light of the authors' novel findings pointing to a role of DDRNAs in DDR control, a known tumor suppressive mechanism[37], it is tempting to suggest that, in addition to their well-characterized functions in the modulation of gene expression, DICER and DROSHA RNA products may curb cancerous cell proliferation by sustaining DDR activation and this generates the selective pressure for the inactivation of factors involved in their biogenesis. The authors also report that in an in vitro cellular system, DDR foci are lost in irradiated cells following RNase A treatment and that site-specific DDRNAs, even if generated by chemical synthesis or upon in vitro cleavage by recombinant DICER, are required to restore them. This suggests that DDRNAs are locally generated and favor the assembly of DDR factors in the shape of detectable DDR foci at the DNA damaged site. Indeed RNA sequencing confirmed the presence of short RNAs arising from the integrated exogenous locus which are induced upon cut. Comparison with short RNAs generated at other non miRNA genomic loci indicates that they are distinct from products of RNA degradation and their nucleotide bias at 5' end and 3' end indicates that these RNAs are processed at preferential RNA precursors sites.

Although at present how DDRNAs act to control DDR activation has not been elucidated in full, the observation that they act in a manner dependent on the MRN complex place them upstream of the canonical DDR signaling cascade.

Although novel and unanticipated, the authors' results are consistent with the emerging evidence supporting a role for RNA molecules in DDR. Indeed, an epistasis map generated in fission yeast has recently shown that DDR components display genetic interactions with the RNAi machinery[56] and components of the large DROSHA complex have been identified in a ATM-dependent phosphoproteome screen[57]. In Drosophila, repeated DNA integrity is dependent on RNAi pathway[58]. In Saccharomyces cerevisiae and in Oxytricha Trifallax RNA orchestrates recombination and RNA can function as a template for DNA repair events in S. cerevisiae[59,60,61]. It is also intriguing to observe that like several DDR factors, that are inactivated early in apoptosis in order to prevent DDR activation[62], also DICER is specifically cleaved by caspases during apoptosis[63]. Recently, ATM has been shown to directly modulate the biogenesis of DICER and DROSHA RNA products by phosphorylating KSRP[64].

Finally, it is worth noticing that the here-described novel functions of components of the RNAi machinery in the modulation of the response to DNA damage are consistent with its well-established and evolutionary-conserved role of preserving genome integrity from viral invaders, transposons and retroelements[65].

REFERENCES

1 Jackson, S. P. & Bartek, J. Nature 461, 1071-1078 (2009).
2 d'Adda di Fagagna, F. Nat Rev Cancer 8, 512-522 (2008).
3 Clark, M. B. et al. PLoS biology 9, e1000625; discussion e1001102, doi:10.1371/journal.pbio.1000625 (2011).
4 Wilusz, J. E., Sunwoo, H. & Spector, D. L. Genes Dev 23, 1494-1504 (2009).
5 Guttman, M. et al. Nature 458, 223-227 (2009).
6 Drinnenberg, I. A. et al. Science 326, 544-550 (2009).
7 Clemson, C. M. et al. Mol Cell 33, 717-726 (2009).
8 Wutz, A. Bioessays 25, 434-442 (2003).
9 Orom, U. A. et al. Cell 143, 46-58 (2010).
10 Wang, X. et al. Nature 454, 126-130 (2008).
11 Zhao, J., et al. Science 322, 750-756 (2008).

12 Calabrese, J. M., et al. *Proc Natl Acad Sci USA* 104, 18097-18102 (2007).
13 Sun, B. K., Deaton, A. M. & Lee, J. T. *Mol Cell* 21, 617-628 (2006).
14 Berezikov, E. Nature reviews. *Genetics* 12, 846-860 (2011).
15 Farazi, T. A., Juranek, S. A. & Tuschl, T. *Development* 135, 1201-1214 (2008).
16 Lee, H. C. et al. *Nature* 459, 274-277 (2009).
17 Kim, V. N., Han, J. & Siomi, M. C. *Nat Rev Mol Cell Biol* 10, 126-139 (2009).
18 Esquela-Kerscher, A. & Slack, F. J. *Nat Rev Cancer* 6, 259-269 (2006).
19 He, L., He, X., Lowe, S. W. & Hannon, G. J. *Nat Rev Cancer* 7, 819-822 (2007).
20 Di Micco, R. et al. *Nature* 444, 638-642 (2006).
21 Bartkova, J. et al. *Nature* 444, 633-637 (2006).
22 Narita, M. et al. *Cell* 113, 703-716 (2003).
23 White, S. A. & Allshire, R. C. *Curr Top Microbiol Immunol* 320, 157-183 (2008).
24 Zhang, H., et al. *Cell* 118, 57-68 (2004).
25 Cummins, J. M. et al. *Proc Natl Acad Sci USA* 103, 3687-3692 (2006).
26 Cescutti, R., et al. *Embo J* 29, 3723-3732 (2010).
27 Wei, Y., Yu, L., Bowen, J., Gorovsky, M. A. & Allis, C. D. *Cell* 97, 99-109 (1999).
28 Nicoli, S. et al. *Nature* 464, 1196-1200 (2010).
29 Wienholds, E., et al., *Nat Genet* 35, 217-218 (2003).
30 Maison, C. et al. *Nat Genet* 30, 329-334 (2002).
31 Pryde, F. et al. *J Cell Sci* 118, 2043-2055 (2005).
32 Flick, K. E., et al. *Nature* 394, 96-101 (1998).
33 Berkovich, E., *Nat Cell Biol* 9, 683-690 (2007).
34 Iacovoni, J. S. et al. *Embo J* 29, 1446-1457 (2010).
35 Soutoglou, E. et al. *Nat Cell Biol* 9, 675-682 (2007).
36 Dupre, A. et al. *Nat Chem Biol* 4, 119-125 (2008).
37 Halazonetis, T. D., Gorgoulis, V. G. & Bartek, J. *Science* 319, 1352-1355 (2008).
38 Kumar, M. S., et al. *Nat Genet* 39, 673-677 (2007).
39 Kumar, M. S. et al. *Genes Dev* 23, 2700-4 (2009).
40 Hill, D. A. et al. *Science* 325, 965 (2009).
41 Melo, S. A. et al. *Nat Genet* 41, 365-370 (2009).
42 Mudhasani, R. et al. *J Cell Biol* 181, 1055-1063 (2008).
43 Tang, K. F. et al. *J Cell Biol* 182, 233-239 (2008).
44 Kumar, M. S. et al. *Genes Dev* 23, 2700-2704 (2009).
50 Muchardt, C. et al. *EMBO Rep* 3, 975-981 (2002).
51 Eskeland, R., Eberharter, A. & Imhof, A. *Mol Cell Biol* 27, 453-465 (2007).
52 Ayoub, N., et al., *Nature* 453, 682-686 (2008).
53 Murga, M. et al. *J Cell Biol* 178, 1101-1108 (2007).
54 Bakkenist, C. J. & Kastan, M. B. *Nature* 421, 499-506 (2003).
55 Goodarzi, A. A. et al. *Mol Cell* 31, 167-177 (2008).
56 Roguev, A. et al. *Science* 322, 405-410 (2008).
57 Bensimon, A. et al. *Sci Signal* 3, rs3 (2010).
58 Peng, J. C. & Karpen, G. H. *Nat Cell Biol* 9, 25-35 (2007).
59 Derr, L. K. & Strathern, J. N. *Nature* 361, 170-173 (1993).
60 Nowacki, M. et al. *Nature* 451, 153-158 (2008).
61 Storici, F., et al. *Nature* 447, 338-341 (2007).
62 Smith, G. C., et al., *Mol Cell Biol* 19, 6076-6084. (1999).
63 Ghodgaonkar, M. M. et al. *Cell Death Differ* 16, 858-868 (2009).
64 Zhang, X., Wan, G., Berger, F. G., He, X. & Lu, X. *Mol Cell* 41, 371-383 (2011).
65 Hannon, G. J. RNA interference. *Nature* 418, 244-251 (2002).
66 Duchaine, T. F. et al. *Cell* 124, 343-354 (2006).
67 Sidi, S. et al. *Cell* 133, 864-877 (2008).
68 Kawano, M. et al. *Biotechniques* 49, 751-755 (2010).
69 Jepsen J S, Sorensen M D, and Wengel J. (2004). Oligonucleotides, 14(2):130-46.
70 Machlin E S, Sarnow P, and Sagan S M. (2012). Curr Gene Ther, 12(4):301-6.
71 Lazzerini Denchi, E and de Lange T (2007). Nature, 448, 1068-1071
72 van Steensel B, Smogorzewska A and de Lange T (1998). Cell, 92 (3), 401-413
73 de Lange T (2005) Gen Dev 19 (18), 2100-2110
74 Sfeir A et al, (2009) Cell 138 (1), 90-103
75 Harley C B, Futcher A B and Greider C W (1990) Nature 345, 458-460
76 Herbig U, et al. (2004) Mol Cell 14, 501-513
77 d'Adda di Fagagna F et al. (2003) Nature 426, 194-198
78 Fumagalli, M. et al. (2012) Nat Cell Biol 14, 355-365
79 Michalik, K. M. et al (2012). Nucleic Acid Res. 40: 9596-603
80 Limmer K, Aschenbrenner D, Gaub H E (2013) Nucleic Acids Res. 41(6):e69
81 Wei et al, (2012) Cell 149(1):101-12
82 Blazkova H et al (2010). J Cell Mol Med. 2010 January; 14(1-2):357-67.
83 Anglana M et al (1999). Nucleic Acids Res. 1999 Nov. 1; 27(21):4276-81
84. Serrano M et al (2007). Nat Rev Mol Cell Biol. September; 8(9):715-22.
85. Calado R T et al (2009). N. Engl J Med. 361:2353-2365

What is claimed is:

1. A method for the treatment of a condition induced by a sequence specific damaged genomic locus, wherein the damage occurs at telomeres and/or is caused by a sequence-specific DNA endonuclease, the method comprising:
   administering an inhibitor of small RNAs (DDRNAs), wherein the DDRNAs are generated in cis by processing an RNA transcript with DICER and/or DROSHA;
   wherein said RNA transcript was synthesized using the sequence specific damaged genomic locus as a template for transcription;
   wherein the DDRNAs comprise a sequence of the sequence specific damaged genomic locus; and
   wherein the inhibitor is at least one exogenous sequence specific inhibitory oligonucleotide.

2. The method according to claim 1, wherein the condition induced by a sequence specific damaged genomic locus is at least one of cancer, aging, or a viral infection.

3. The method according to claim 2, wherein aging is associated with at least one of short telomeres, damaged telomeres, or dysfunctional telomeres.

4. The method according to claim 1, wherein said sequence-specific inhibitor oligonucleotide is a locked nucleic acid (LNA) molecule.

5. The method according to claim 1, wherein the inhibitor is an inhibitor of DICER and/or DROSHA.

6. The method according to claim 5, wherein the inhibitor is a siRNA.

7. The method of claim 1, wherein the at least one exogenous sequence-specific inhibitory oligonucleotide specifically binds to a sequence comprising the sequence of the DDRNA, and wherein the specific binding inhibits the function and/or impairs the production of the DDRNAs.

8. The method of claim 1, wherein the at least one exogenous sequence specific inhibitory oligonucleotide is selected from the group consisting of: a locked nucleic acid (LNA), a 2'-O-methyl-modified oligonucleotide, or phosphorothioate modified oligonucleotide.

9. A method for the treatment of a condition induced by a sequence specific damaged genomic locus, the method comprising:
   administering an inhibitor of small RNAs (DDRNAs), wherein the DDRNAs are generated in cis by processing an RNA transcript of the damaged genomic locus with DICER and/or DROSHA;
   wherein said RNA transcript was synthesized using the sequence specific damaged genomic locus as a template for transcription;
   wherein the DDRNAs comprise the sequence of the sequence specific damaged genomic locus;
   wherein the inhibitor is at least one exogenous sequence specific inhibitory oligonucleotide; and
   wherein the condition is selected from the group consisting of senescence induced by: persistent DNA damage response activation at damaged telomeres; and oncogene-induced senescence.

10. The method according to claim 9, wherein said sequence-specific inhibitor oligonucleotide is a locked nucleic acid (LNA) molecule.

11. The method according to claim 9, wherein the inhibitor is an inhibitor of DICER and/or DROSHA.

12. The method according to claim 11, wherein the inhibitor is a siRNA.

13. The method of claim 9, wherein the at least one exogenous sequence-specific inhibitory oligonucleotide specifically binds to a sequence comprising the sequence of the DDRNA, and wherein the specific binding inhibits the function and/or impairs the production of the DDRNAs.

14. The method of claim 9, wherein the at least one exogenous sequence specific inhibitory oligonucleotide is selected from the group consisting of: a locked nucleic acid (LNA), a 2'-O-methyl-modified oligonucleotide, or phosphorothioate modified oligonucleotide.

15. A method for the treatment of a condition induced by a sequence specific damaged genomic locus wherein the damage occurs at telomeres or is caused by a sequence-specific DNA endonuclease, the method comprising:
   administering an inhibitor of small RNAs (DDRNAs), wherein the DDRNAs are generated in cis by processing an RNA transcript of the damaged genomic locus with DICER and/or DROSHA;
   wherein said RNA transcript was synthesized using the sequence specific damaged genomic locus as a template for transcription;
   wherein the DDRNAs comprise the sequence of the sequence specific damaged genomic locus;
   wherein the inhibitor is at least one exogenous sequence specific locked nucleic acid, siRNA, 2'-O-methyl-modified oligonucleotide, or phosphorothioate modified oligonucleotide; and wherein the condition is selected from the group consisting of senescence induced by: persistent DNA damage response activation at damaged telomeres; and oncogene-induced senescence.

16. The method according to claim 15, wherein the inhibitor is an inhibitor of DICER and/or DROSHA.

17. The method of claim 15, wherein the at least one exogenous sequence-specific inhibitory locked nucleic acid or siRNA specifically binds to a sequence comprising the sequence of the DDRNA, and wherein the specific binding inhibits the function and/or impairs the production of the DDRNAs.

* * * * *

UNITED STATES PATENT AND TRADEMARK OFFICE
CERTIFICATE OF CORRECTION

PATENT NO. : 10,240,154 B2
APPLICATION NO. : 15/476800
DATED : March 26, 2019
INVENTOR(S) : Fabrizio d'Adda di Fagagna et al.

It is certified that error appears in the above-identified patent and that said Letters Patent is hereby corrected as shown below:

On the Title Page

Item (56), Column 2, Line 31, Under Other Publications, change "Vvei" to --Wei--.

In the Specification

Column 3, Line 64, "Drososphila" should be --Drosophila--.

Column 5, Line 16 (approx.), "active" should be --active.--.

Column 5, Line 36 (approx.), "bleomycine" should be --bleomycin--.

Column 6, Line 42, "mya" should be --may--.

Column 8, Line 3, "machinery" should be --machinery.--.

Column 10, Line 17, "2A-2D)" should be --2A-2D--.

Column 17, Line 14, "polyacrilamide" should be --polyacrylamide--.

Column 18, Lines 2-3, "Bioanalyser" should be --Bioanalyzer--.

Column 18, Line 29, "Bioanalyser" should be --Bioanalyzer--.

Column 18, Line 34, "Bioanalyser" should be --Bioanalyzer--.

Column 20, Line 19, "ecotrophic" should be --ecotropic--.

Column 20, Line 26, "gentamicine" should be --gentamicin--.

Signed and Sealed this
Thirtieth Day of July, 2019

Andrei Iancu
*Director of the United States Patent and Trademark Office*

CERTIFICATE OF CORRECTION (continued)
U.S. Pat. No. 10,240,154 B2

Column 20, Line 59, "gentamicine" should be --gentamicin--.

Column 21, Line 7, "TRF2$^{flox/flow}$" should be --TRF2$^{flox/flox}$--.

Column 22, Line 58 (Approx.), "TNRC 6A:" should be --TNRC6A:--.

Column 23, Line 41 (Approx.), "rnul9" should be --rnu19--.

Column 24, Line 15 (Approx.), "GGCCCGAGAGCCTTTTATAG ," should be --GGCCCGAGAGCCTTTTATAG,--.

Column 25, Line 49, "7.5." should be --7.5,--.

Column 26, Line 1, "RNaseA" should be --RNase A--.

Column 26, Line 49, "acqueous" should be --aqueous--.

Column 27, Line 62, "Succesfully" should be --Successfully--.

Column 29, Line 48, "(Figure S1a)," should be --(FIG. 1A),--.

Column 30, Line 50, "(Figure S 7b-d)." should be --(FIGS. 7B-D).--.

Column 31, Line 23, "hypomorphyc" should be --hypomorphic--.

Column 31, Line 38, "checkpoint'." should be --checkpoint1.--.

Column 33, Line 51, "that that" should be --that--.

Column 34, Line 18, "25C)" should be --25C).--.

Column 35, Line 6, "cyclohexamide" should be --cycloheximide--.

Column 37, Line 58, "Oligonuncleotides" should be --Oligonucleotides--.

Column 37, Line 64, "RNaseA" should be --RNase A--.

Column 38, Line 8, "RNaseA" should be --RNase A--.

Column 38, Line 26, "RNaseA" should be --RNase A--.

Column 39, Line 1, "(FIG. 35a-b)." should be --(FIGS. 35A-B).--.

Column 41, Line 33 (Approx.), "J29," should be --J 29,--.